(12) United States Patent
Pau et al.

US012281155B1

(10) Patent No.: US 12,281,155 B1
(45) Date of Patent: Apr. 22, 2025

(54) BROADLY SARS-CoV-2 NEUTRALIZING MONOCLONAL ANTIBODIES AND USES THEREOF

(71) Applicants: INSTITUT PASTEUR, Paris (FR); SPIKIMM, Paris (FR)

(72) Inventors: Antoine Pau, Paris (FR); Hugo Mouquet, Paris (FR); Cyril Planchais, Paris (FR)

(73) Assignees: INSTITUT PASTEUR, Paris (FR); SPIKIMM, Paris (FR)

( * ) Notice: Subject to any disclaimer, the term of this patent is extended or adjusted under 35 U.S.C. 154(b) by 0 days.

(21) Appl. No.: 18/417,613

(22) Filed: Jan. 19, 2024

(51) Int. Cl.
| | | |
|---|---|---|
| *C07K 16/10* | (2006.01) | |
| *A61K 39/00* | (2006.01) | |
| *A61P 31/14* | (2006.01) | |
| *C12N 15/63* | (2006.01) | |
| *G01N 33/569* | (2006.01) | |

(52) U.S. Cl.
CPC .......... *C07K 16/1003* (2023.08); *A61P 31/14* (2018.01); *C12N 15/63* (2013.01); *G01N 33/56983* (2013.01); *A61K 2039/507* (2013.01); *C07K 2317/14* (2013.01); *C07K 2317/41* (2013.01); *C07K 2317/565* (2013.01); *C07K 2317/567* (2013.01)

(58) Field of Classification Search
CPC .......... C07K 16/1003; C07K 2317/567; A61P 31/14; C12N 15/63; G01N 33/56983; A61K 2039/507
See application file for complete search history.

(56) References Cited

PUBLICATIONS

Rudikoff S, Giusti AM, Cook WD, Scharff MD. Single amino acid substitution altering antigen-binding specificity. Proc Natl Acad Sci U S A. Mar. 1982;79(6):1979-83. (Year: 1982).*

* cited by examiner

*Primary Examiner* — Nicole Kinsey White
*Assistant Examiner* — Ruixue Wang
(74) *Attorney, Agent, or Firm* — Arrigo, Lee, Guttman & Mouta-Bellum LLP

(57) ABSTRACT

The invention relates to antibodies against Severe Acute Respiratory Syndrome-related Coronavirus 2 (SARS-CoV-2), in particular human neutralizing monoclonal antibodies against Severe Acute Respiratory Syndrome-related Coronavirus 2 (SARS-CoV-2) having a broad neutralization spectrum, and their use for the diagnosis, monitoring, prevention, and treatment of SARS-CoV-2 infection and associated disease (COVID-19).

21 Claims, 6 Drawing Sheets

Specification includes a Sequence Listing.

RBD binding

| | SPK002 | A1 | A2 | A3 | A4 | A5 | A6 | B1 | B2 | C1 | C2 | C3 |
|---|---|---|---|---|---|---|---|---|---|---|---|---|
| Wuhan | 34 | 33 | 33 | 33 | 34 | 34 | 34 | 31 | 31 | 32 | 32 | 34 |
| Delta | 34 | 31 | 31 | 31 | 31 | 33 | 34 | 33 | 32 | 32 | 32 | 33 |
| o BA.2 | 33 | 33 | 32 | 32 | 29 | 27 | 29 | 29 | 26 | 28 | 23 | 19 |
| o BA.2.75.2 | 16 | 34 | 34 | 34 | 34 | 34 | 30 | 30 | 29 | 28 | 28 | 29 |
| o BA.4/5 | 33 | 31 | 30 | 30 | 30 | 32 | 33 | 31 | 30 | 30 | 30 | 32 |
| o BQ.1.1 | 24 | 30 | 30 | 30 | 30 | 30 | 32 | 31 | 31 | 31 | 31 | 31 |
| o XBB.1.5 | 25 | 35 | 36 | 35 | 35 | 35 | 33 | 31 | 32 | 31 | 31 | 32 |
| o XBB.1.16 | 20 | 30 | 31 | 31 | 30 | 31 | 31 | 30 | 30 | 29 | 29 | 31 |
| EG.5 | 1 | 35 | 35 | 34 | 34 | 35 | 27 | 33 | 32 | 32 | 32 | 33 |
| BA.2.86 | 16 | 37 | 38 | 38 | 38 | 38 | 39 | 39 | 39 | 38 | 38 | 38 |
| JN-1 | 2 | 39 | 37 | 26 | 31 | 32 | 7 | 38 | 28 | 39 | 33 | 29 |

*Binding AUC values are shown*

Figure 3

RBD-ACE-2 blocking

| | SPK002 | A1 | A2 | A3 | A4 | A5 | A6 | B1 | B2 | C1 | C2 | C3 |
|---|---|---|---|---|---|---|---|---|---|---|---|---|
| RBD Wuhan | 88 | 92 | 92 | 94 | 88 | 89 | 93 | 87 | 90 | 94 | 88 | 88 |
| RBD δ | 93 | 94 | 95 | 95 | 93 | 93 | 93 | 91 | 88 | 94 | 90 | 95 |
| RBD BA.2 | 94 | 95 | 94 | 94 | 93 | 93 | 94 | 95 | 92 | 95 | 93 | 94 |
| RBD BA.2.75.2 | 19 | 96 | 96 | 96 | 96 | 95 | 91 | 91 | 91 | 95 | 92 | 94 |
| RBD BA.4/5 | 92 | 97 | 97 | 96 | 96 | 96 | 85 | 95 | 91 | 97 | 93 | 94 |
| RBD BQ.1.1 | 17 | 97 | 97 | 96 | 96 | 96 | 89 | 97 | 95 | 97 | 95 | 94 |
| RBD XBB.1.5 | 27 | 97 | 96 | 95 | 95 | 95 | 83 | 97 | 92 | 96 | 93 | 90 |
| RBD XBB.1.16 | 26 | 97 | 96 | 95 | 95 | 95 | 83 | 97 | 92 | 96 | 93 | 90 |
| RBD EG.5 | 0 | 90 | 88 | 79 | 80 | 83 | 33 | 95 | 70 | 96 | 89 | 81 |
| RBD BA.2.86 | 2 | 85 | 85 | 85 | 80 | 84 | 57 | 94 | 86 | 96 | 91 | 90 |
| RBD JN-1 | 0 | 71 | 1 | 0 | 2 | 2 | 0 | 66 | 0 | 83 | 28 | 0 |

*Blocking % values are shown*

Figure 4

S-Fuse neutralization assay

*IC50 values (µg/ml) are shown*

| | SPK002 | A1 | A2 | A3 | A4 | A5 | A6 | B1 | B2 | C1 | C2 | C3 |
|---|---|---|---|---|---|---|---|---|---|---|---|---|
| D614G | 0.09 | 0.08 | 0.10 | 0.11 | 0.11 | 0.09 | 0.07 | 0.11 | 0.09 | 0.08 | 0.06 | 0.08 |
| XBB.1.5 | 215.50 | 0.07 | 0.10 | 0.12 | 0.12 | 0.12 | 0.36 | 0.07 | 0.14 | 0.07 | 0.14 | 0.13 |
| XBB.1.16 | 155.90 | 0.17 | 0.33 | 0.36 | 0.36 | 0.36 | 1.34 | 0.18 | 0.32 | 0.12 | 0.21 | 0.30 |
| BA.2.86 | 100.00 | 0.02 | 0.05 | 0.05 | 0.04 | 0.08 | 0.63 | 0.03 | 0.19 | 0.03 | 0.05 | 0.33 |
| EG.5.1 | 100.00 | 0.15 | 1.65 | 5.92 | 2.80 | 2.86 | 21.05 | 0.19 | 5.53 | 0.16 | 2.16 | 6.08 |
| JN.1 | 100.00 | 1.28 | 25.26 | 76.26 | 54.57 | 50.93 | 100.00 | 4.10 | 85.85 | 1.73 | 53.83 | 60.14 |

Figure 5

| mAbs | Chain | VH | | | VL | | | | | | | Mut# |
|---|---|---|---|---|---|---|---|---|---|---|---|---|
| | Position | 26 | 29 | 51 | 71 | 28 | 29 | 30 | 31 | 32 | 61 | 86 | 91 | |
| SPK002-A1 | | G | V | I | R | S | V | S | S | S | G | I | Q | 0 |
| SPK002-A2 | | T | V | I | A | G | F | S | S | S | G | V | Q | 5 |
| SPK002-A3 | | T | V | I | A | G | V | S | S | S | G | V | Q | 4 |
| SPK002-A4 | | V | V | I | A | S | V | S | S | S | G | V | Q | 3 |
| SPK002-A5 | | V | V | I | A | S | V | S | S | S | G | V | Q | 3 |
| SPK002-A6 | | G | V | I | A | S | V | S | S | S | G | I | Q | 2 |
| SPK002-B1 | | T | V | I | Y | S | V | S | D | S | G | I | Y | 4 |
| SPK002-B2 | | T | V | I | Y | S | V | S | S | S | G | I | Q | 2 |
| SPK002-C1 | | T | V | A | T | S | V | S | D | S | G | V | Y | 6 |
| SPK002-C2 | | T | V | A | T | S | V | S | S | S | G | V | Q | 4 |
| SPK002-C3 | | T | V | I | T | S | V | S | S | S | G | V | Q | 3 |

Figure 6

BROADLY SARS-CoV-2 NEUTRALIZING MONOCLONAL ANTIBODIES AND USES THEREOF

REFERENCE TO SEQUENCE LISTING SUBMITTED ELECTRONICALLY

The instant application contains a Sequence Listing which has been submitted electronically in XML format and is hereby incorporated by reference in its entirety. Said XML copy, created on Jan. 17, 2024, is named PI024883.xml and is 101,801 bytes in size.

FIELD OF THE INVENTION

The invention relates to antibodies against Severe Acute Respiratory Syndrome-related Coronavirus 2 (SARS-CoV-2), in particular human neutralizing monoclonal antibodies against Severe Acute Respiratory Syndrome-related Coronavirus 2 (SARS-CoV-,2) and their use for the diagnosis, monitoring, prevention, and treatment of SARS-CoV-2 infection and associated disease (COVID-19).

BACKGROUND OF THE INVENTION

The pandemic caused by emerging Severe Acute Respiratory Syndrome Coronavirus 2 (SARS-CoV-2), which causes Coronavirus Disease-2019 (COVID-19) and accounts to date for nearly 470 million infection cases and 6 million deaths worldwide (https://www.who.int/), presents a serious global public health emergency in urgent need for prophylactic and therapeutic interventions.

Coronaviruses are enveloped, positive-sense, single-stranded RNA viruses that infect humans and mammals. Coronaviruses genomes encode non-structural polyprotein and structural proteins, including the homotrimeric spike(S) glycoprotein, envelope (E), membrane (M) and nucleocapsid (N) proteins. Several coronaviruses are pathogenic to human, leading to varying degrees of symptoms severity (Cui et al., Nat Rev Microbiol. 2019 March; 17 (3): 181-92). The betacoronavirus genus (Beta-CoV or B-CoV) which is divided in 4 lineages or groups (A, B, C, D) comprises the highly human-pathogenic coronaviruses in group B/C. Beta-CoV group B/C includes the severe acute respiratory syndrome coronaviruses (SARS-CoV or SARS-CoV-1) that emerged in China in 2002, the Middle East respiratory syndrome coronavirus (MERS-COV), first detected in Saudi Arabia in 2012, and the new coronavirus named SARS-CoV-2 that causes COVID-19, isolated in China in 2019 (SARS-CoV-2 isolate Wuhan-Hu-1), in association with cases of severe acute respiratory syndrome (Peiris et al., Nat Med., 2004 December; 10 (12 Suppl): S88-97; Zaki et al., N Engl J Med., 2012 Nov. 8; 367 (19): 1814-20; Lee et al., BMC Infect Dis. 2017 Jul. 14; 17 (1): 498; Zhu N et al., N Engl J Med., 2020 Jan. 24). In contrast, Beta-CoV group A includes HCoV-OC43 and HCoV-HKU1 which can cause the common cold.

Antibodies developing in response to SARS-CoV-2 infection and vaccination are essential for long-term protection against COVID-19. Human neutralizing SARS-CoV-2 antibodies appear to play a key role in the control of COVID-19 infection and represent promising immunotherapeutic tools for treating SARS-CoV-2 infected humans with mild-to-moderate disease. Decoding antibody responses in COVID-19 is fundamental in understanding the basic mechanisms of humoral immunity to the SARS-CoV-2 Spike protein (SARS-CoV-2-S), the target of neutralizing antibodies, but also to develop effective vaccine and monoclonal antibody-based immunotherapy strategies.

The Spike glycoprotein has key roles in the viral cycle, as it is involved in receptor recognition, virus attachment and entry, and is thus a crucial determinant of host tropism and transmission capacity. SARS-CoV-2 cellular entry depends on binding between the viral Spike protein receptor-binding domain (RBD) and the angiotensin converting enzyme 2 (ACE2) target receptor. Binding with ACE2 triggers a cascade of cell membrane fusion events for viral entry. Each S protomer consists of two subunits that are cleaved by proteases: a globular S1 domain and the N-terminal region, and the membrane-proximal S2 and transmembrane domains. Determinants of host range and cellular tropisms are found in the RBD within the S1 domain, while mediators of membrane fusion have been identified within the S2 domain. Anti-SARS-CoV-2 antibody neutralizing potency is determined by competition with ACE2 receptor for RBD binding.

Antibodies rapidly develop in response to SARS-CoV-2 infection, including neutralizing antibodies recognizing distinct S protein regions. The RBD is the primary target of neutralizing antibodies including potent neutralizers, but the NTD and S2 stem region also contain neutralizing epitopes. SARS-CoV-2 neutralizing IgA antibodies are detected as early as a week after onset of symptoms, contribute to seroneutralization and can be as potent as IgGs. Neutralizing antibodies are the main correlate of protection for COVID-19 vaccines. Still, SARS-CoV-2 spike-specific antibodies, including non-neutralizers, can exert antiviral Fc-dependent effector functions important for in vivo protection i.e., antibody-dependent cellular cytotoxicity (ADCC), and phagocytosis (ADCP).

Since mid-2020, emerging variants of SARS-CoV-2 with increased transmissibility and/or reduced sensitivity to neutralizing antibodies due to predicted mutations in the Spike protein, in particular its receptor-binding region (RBD), were reported in several countries and are currently spreading worldwide. The first variant reported was in UK (lineage B.1.1.7; notable mutations N501Y, 69-70del, P681H); then in South Africa (SA) (lineage B.1.351; notable mutations N501Y, E484K, K417N) and Brazil (BR) (lineage P.1; notable mutations N501Y, E484K, K417T). Some monoclonal and serum-derived antibodies are reported to be from 10 to 60 time less effective in neutralizing virus bearing the E484K mutation (SARS-CoV-2 variants SA and BR). Some vaccines might see their efficacy reduced against these variants.

Since then, new emerging variants of SARS-CoV-2 are spreading worldwide, including lineages of Variants of Concerns (VOCs) such as the ones cited below, or VOCs comprising the same mutations in the spike proteins responsible for increased affinity to hACE2 and potential immune escape:

Alpha (B.1.1.7) N501Y; A570D; P681H; T716I; S982A; D1118H

Beta (B.1.351) D80A; D215G; K417N; E484K; N501Y; A701V

Gamma (P.1) L18F; T20 N; P26S; D138Y; R190S; K417T; E484K; N501Y; H655Y; T1027I

Delta (B.1.617.2) T19R; L452R; T478K; P681R; D950N

Omicron (BA.1 sublineage) (B. 1.1.529) A67V, H69-, V70-, T95I, G142-, V143-, Y144-, Y145D, N211-, L212I, G339D, S371L, S373P, S375F, K417N, N440K, G446S, S477N, T478K, E484A, Q493R, G496S, Q498R, N501Y, T547K, D614G, H655Y, N679K, P681H, N764K, D796Y, N856K, Q954H, N969K, L981F Omicron (BA.2 sublineage) G339D; F367V; S371F; S373P; S375F; T376A; D405N; R408S; K417N; N440K; S477N; T478K; E484A; Q493R; Q498R; N501Y; Y505H Omicron (BA.2.75 sublineage) W152R, F157L, I210V, G257S, D339H, G446S, N460K, Q493

Omicron BA.2.86 sublineage)

Omicron (XBB1.5 sublineage) N460K, S486P, F490S

Omicron (XBB.1.16 sublineage) E180V, T478R, F486P

Omicron (FE.1 sublineage) Q183E, F456I, F486P, F490S

Omicron (CH1.1 sublineage) K444T, I452R

Omicron (BA.4. and BA.5. sublineages)

Omicron (BQ.1.1. sublineage)

Omicron (XBB.1.5 sublineage)

Omicron (XBB.1.16 sublineage)

Omicron (EG.5. sublineage)

To develop prophylactic and therapeutic approaches specific to SARS-CoV-2, there is a need for neutralizing antibodies against SARS-CoV-2, in particular human neutralizing antibodies against SARS-CoV-2 including human antibodies capable of neutralizing SARS-CoV-2 variants, especially the above VOCs and variants of such VOCs and VOCs having a combination of the above mutations. The challenge is to provide monoclonal antibodies, alone or in combination, which retain efficient neutralizing properties to confer protection to individuals at risk of developing a SARS from present and future VOCs. While it cannot be expected that a universal SARS-CoV2 Spike monoclonal antibody (mAb) would be such that it would keep sufficient efficacy against most VOCs and future VOCs, it is a goal to provide mAbs that are consistent in neutralizing the majority of these VOCs and VOCs comprising different combinations of these mutations; so that it remains useful overtime to prevent or treat SARS.

Immunotherapies based on SARS-CoV-2 neutralizing antibodies have been rapidly explored, and this led to the clinical use of several mAbs alone or in bi-therapies. Highly potent human SARS-CoV-2 neutralizing antibodies isolated so far, including those tested or used in clinics, all target the RBD and can prevent or protect animals from infection in preclinical models. However, viral variants with spike mutations conferring resistance to antibody neutralization emerged during the pandemics and annihilated some of these therapies. The search for broadly neutralizing mAbs is pursued. Antibodies against a significant spectrum of SARS-CoV-2 variants have been described in the art, such as those disclosed in the PCT application published under n° WO 2022/228827.

There remains a need in the art for novel antibodies active against all VOCs, including the currently prevalent omicron lineage, while being active against previously prevalent but still circulating SARS-CoV-2 variants.

This challenge of providing mAbs that are consistent in neutralizing the majority of these VOCs and VOCs comprising different combinations of these mutations is enormous considering the results presented herein which shows the loss of potency of most of the currently FDA/EMEA approved therapeutic mAbs. The present invention fulfills this need and provides specific mAbs with retained potency across majors VOCs displaying such mutations.

BRIEF SUMMARY OF THE INVENTION

The invention provides antibodies against Severe Acute Respiratory Syndrome-related Coronavirus 2 (SARS-CoV-2) and fragments thereof, including antigen-binding fragments thereof, in particular human neutralizing antibodies against Severe Acute Respiratory Syndrome-related Coronavirus 2 (SARS-CoV-2), nucleic acids, vectors encoding the antibodies, compositions, reagents, medical devices, and kits comprising the antibodies, nucleic acids, vectors according to the present disclosure.

The invention encompasses methods of making and using, as well as uses of the antibodies, nucleic acids, vectors, according to the present disclosure, in particular for the detection, diagnosis, monitoring, prevention and treatment of SARS-CoV-2 infection and associated disease (COVID-19).

An antibody, preferably of any isotype or species, directed against the viral Spike protein receptor binding-domain (RBD) of Severe Acute Respiratory Syndrome-related Coronavirus 2 (SARS-CoV-2), or antigen-binding fragment thereof, comprising:
(i) a heavy chain variable domain, or fragment thereof, comprising:
    a HCDR1 of SEQ ID NO. 1,
    a HCDR2 selected from SEQ ID NO. 2 and SEQ ID NO. 20,
    a HCDR3 of SEQ ID NO. 3,
    or variants thereof comprising up to 1 amino acid mutation in the sequence of 1, 2 or 3 CDRs,
and/or
(ii) a light chain variable domain, or fragment thereof, comprising:
    a LCDR1 selected from SEQ ID NO. 9, SEQ ID NO. 23, SEQ ID NO. 24 and SEQ ID NO. 25,
    a LCDR2 of SEQ ID NO. 10,
    a LCDR3 selected from SEQ ID NO. 11, SEQ ID NO. 27,
    or variants thereof comprising up to 1 amino acid mutation in the sequence of 1, 2 or 3 CDRs,
and
(iii) a HFR3 of the amino acid sequence RFTISXDNSKNTLYLQMNSLRAEDTAVYYCAR (SEQ ID NO. 28) wherein X means an amino acid selected from Alanine, Tyrosine and Threonine.

In some embodiments of the said antibody, or antigen-binding fragment thereof, HFR3 is selected from SEQ ID NO. 6, SEQ ID NO. 21, and SEQ ID NO. 22.

In some embodiments, the said antibody, is selected from:
an antibody comprising:
    (i) a heavy chain variable domain, or fragment thereof, comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 6, and
    (ii) a light chain variable domain, or fragment thereof, comprising (a) a LCDR1 of SEQ ID NO. 9, (b) a LCDR2 of SEQ ID NO. 10 and (c) a LCDR3 of SEQ ID NO. 11,
an antibody comprising:
    (i) a heavy chain variable domain, or fragment thereof, comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 6, and
    (ii) a light chain variable domain, or fragment thereof, comprising (a) a LCDR1 of SEQ ID NO. 23, (b) a LCDR2 of SEQ ID NO. 10 and (c) a LCDR3 of SEQ ID NO. 11,
an antibody comprising:
    (i) a heavy chain variable domain, or fragment thereof, comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 6, and
  (ii) a light chain variable domain, or fragment thereof, comprising (a) a LCDR1 of SEQ ID NO. 24, (b) a LCDR2 of SEQ ID NO. 10 and (c) a LCDR3 of SEQ ID NO. 11,
an antibody comprising:
  (i) a heavy chain variable domain, or fragment thereof, comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 21, and
  (ii) a light chain variable domain, or fragment thereof, comprising (a) a LCDR1 of SEQ ID NO. 25, (b) a LCDR2 of SEQ ID NO. 10 and (c) a LCDR3 of SEQ ID NO. 27,
an antibody comprising:
  (i) a heavy chain variable domain, or fragment thereof, comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 21, and
  (ii) a light chain variable domain, or fragment thereof, comprising (a) a LCDR1 of SEQ ID NO. 24, (b) a LCDR2 of SEQ ID NO. 10 and (c) a LCDR3 of SEQ ID NO. 11,
an antibody comprising:
  (i) a heavy chain variable domain, or fragment thereof, comprising (a) a HCDR1 of SEQ ID NO. 1, (b) a HCDR2 of SEQ ID NO. 20, (c) a HCDR3 of SEQ ID NO. 3 and (d) a HFR3 of SEQ ID NO. 22, and
  (ii) a light chain variable domain, or fragment thereof, comprising (a) a LCDR1 of SEQ ID NO. 25, (b) a LCDR2 of SEQ ID NO. 10 and (c) a LCDR3 of SEQ ID NO. 27,
an antibody comprising:
  (i) a heavy chain variable domain, or fragment thereof, comprising (a) a HCDR1 of SEQ ID NO. 1, (b) a HCDR2 of SEQ ID NO. 20, (c) a HCDR3 of SEQ ID NO. 3 and (d) a HFR3 of SEQ ID NO. 22, and
  (ii) a light chain variable domain, or fragment thereof, comprising (a) a LCDR1 of SEQ ID NO. 24, (b) a LCDR2 of SEQ ID NO. 10 and (c) a LCDR3 of SEQ ID NO. 11, and
an antibody comprising:
  (i) a heavy chain variable domain, or fragment thereof, comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 22, and
  (ii) a light chain variable domain, or fragment thereof, comprising (a) a LCDR1 of SEQ ID NO. 24, (b) a LCDR2 of SEQ ID NO. 10 and (c) a LCDR3 of SEQ ID NO. 11,
or an antigen-binding fragment of the selected antibody.

In some embodiments, the said antibody is selected from:
an antibody comprising (i) a heavy chain variable domain having 90% or more amino acid identity with SEQ ID NO. 8 and comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 6 and a light chain variable domain having 90% or more amino acid identity with SEQ ID NO. 16 and comprising (a) a LCDR1 of SEQ ID NO. 9, (b) a LCDR2 of SEQ ID NO. 10 and (c) a LCDR3 of SEQ ID of SEQ ID NO. 11,
an antibody comprising (i) a heavy chain variable domain having 90% or more amino acid identity with SEQ ID NO. 29 and comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 6, and
  (ii) a light chain variable domain having 90% or more amino acid identity with SEQ ID NO. 30 and comprising (a) a LCDR1 of SEQ ID NO. 23, (b) a LCDR2 of SEQ ID NO. 10 and (c) a LCDR3 of SEQ ID of SEQ ID NO. 11,
an antibody comprising (i) a heavy chain variable domain having 90% or more amino acid identity with SEQ ID NO. 31 and comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 6 and (ii) a light chain variable domain having 90% amino acid identity with SEQ ID NO. 32 and comprising (a) a LCDR1 of SEQ ID NO. 24, (b) a LCDR2 of SEQ ID NO. 10 and (c) a LCDR3 of SEQ ID of SEQ ID NO. 11,
an antibody comprising (i) a heavy chain variable domain having 90% or more amino acid identity with SEQ ID NO. 33 and comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 6, and (ii) a light chain variable domain having 90% or more amino acid identity with SEQ ID NO. 34 and comprising (a) a LCDR1 of SEQ ID NO. 24, (b) a LCDR2 of SEQ ID NO. 10 and (c) a LCDR3 of SEQ ID of SEQ ID NO. 11,
an antibody comprising (i) a heavy chain variable domain having 90% or more amino acid identity with SEQ ID NO. 35 and comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 6, and (ii) a light chain variable domain having 90% or more amino acid identity with SEQ ID NO. 36 and comprising (a) a LCDR1 of SEQ ID NO. 24, (b) a LCDR2 of SEQ ID NO. 10 and (c) a LCDR3 of SEQ ID of SEQ ID NO. 11,
an antibody comprising (i) a heavy chain variable domain having 90% or more amino acid identity with SEQ ID NO. 37 and comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 6, and (ii) a light chain variable domain having 90% or more amino acid identity with SEQ ID NO. 38 and comprising (a) a LCDR1 of SEQ ID NO. 24, (b) a LCDR2 of SEQ ID NO. 10 and (c) a LCDR3 of SEQ ID of SEQ ID NO. 11,
an antibody comprising (i) a heavy chain variable domain having 90% or more amino acid identity with SEQ ID NO 39 and comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 21, and (ii) a light chain variable domain of SEQ ID NO. 40 and comprising (a) a LCDR1 of SEQ ID NO. 25, (b) a LCDR2 of SEQ ID NO. 10 and (c) a LCDR3 of SEQ ID of SEQ ID NO. 27,
an antibody comprising (i) a heavy chain variable domain having 90% or more amino acid identity with SEQ ID NO 41 and comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 21, and (ii) a light chain variable domain having 90% or more amino acid identity with SEQ ID NO. 42 and comprising (a) a LCDR1 of SEQ ID NO. 24, (b) a LCDR2 of SEQ ID NO. 10 and (c) a LCDR3 of SEQ ID of SEQ ID NO. 11,
an antibody comprising (i) a heavy chain variable domain having 90% or more amino acid identity with SEQ ID NO 43 and comprising (a) a HCDR1 of SEQ ID NO. 1, (b) a HCDR2 of SEQ ID NO. 20, (c) a HCDR3 of SEQ ID NO. 3 and (d) a HFR3 of SEQ ID NO. 22, and (ii) a light chain variable domain having 90% or more amino acid identity with SEQ ID NO. 44 and comprising (a) a LCDR1 of SEQ ID NO. 25, (b) a LCDR2 of SEQ ID NO. 10 and (c) a LCDR3 of SEQ ID of SEQ ID NO. 27, an antibody comprising (i) a heavy chain variable domain having 90% or more amino acid identity with SEQ ID NO 45 and comprising (a) a HCDR1 of SEQ ID NO. 1, (b) a HCDR2 of SEQ ID NO. 20, (c) a HCDR3 of SEQ ID NO. 3 and (d) a HFR3 of SEQ ID NO. 22, and (ii) a light chain variable domain having 90% or more amino acid identity with SEQ ID NO. 46 and comprising (a) a LCDR1 of SEQ ID NO. 24, (b) a LCDR2 of SEQ ID NO. 10 and (c) a LCDR3 of SEQ ID of SEQ ID NO. 11, and an antibody comprising (i) a heavy chain variable domain having 90% or more amino acid identity with SEQ ID NO 47 and comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 22, and (ii) a light chain variable domain having 90% or more amino acid identity with SEQ ID NO. 48 and comprising (a) a LCDR1 of SEQ ID NO. 24, (b) a LCDR2 of SEQ ID NO. 10 and (c) a LCDR3 of SEQ ID of SEQ ID NO. 11.

In some embodiments, the said antibody is selected from:

an antibody comprising (i) a heavy chain variable domain of SEQ ID NO. 8 and (ii) a light chain variable domain of SEQ ID NO. 16, an antibody comprising (i) a heavy chain variable domain of SEQ ID NO. 29 and (ii) a light chain variable domain of SEQ ID NO. 30, an antibody comprising (i) a heavy chain variable domain of SEQ ID NO. 31 and (ii) a light chain variable domain of SEQ ID NO. 32, an antibody comprising (i) a heavy chain variable domain of SEQ ID NO. 33 and (ii) a light chain variable domain of SEQ ID NO. 34, an antibody comprising (i) a heavy chain variable domain of SEQ ID NO. 35 and (ii) a light chain variable domain of SEQ ID NO. 36, an antibody comprising (i) a heavy chain variable domain of SEQ ID NO. 37 and (ii) a light chain variable domain of SEQ ID NO. 38, an antibody comprising (i) a heavy chain variable domain of SEQ ID NO. 39 and (ii) a light chain variable domain of SEQ ID NO. 40, an antibody comprising (i) a heavy chain variable domain of SEQ ID NO. 41 and (ii) a light chain variable domain of SEQ ID NO. 42, an antibody comprising (i) a heavy chain variable domain of SEQ ID NO. 43 and (ii) a light chain variable domain of SEQ ID NO. 44 an antibody comprising (i) a heavy chain variable domain of SEQ ID NO. 45 and (ii) a light chain variable domain of SEQ ID NO. 46, an antibody comprising (i) a heavy chain variable domain of SEQ ID NO. 47 and (ii) a light chain variable domain of SEQ ID NO. 48, or antigen-binding fragment of the selected antibody In some embodiments, the said antibody, or antigen-binding fragment thereof, comprises a constant heavy chain region. According to some of these embodiments, the constant heavy chain region is of SEQ ID NO. 49.

In some embodiments, the said antibody, or antigen-binding fragment thereof, comprises a constant light chain region. According to some of these embodiments, the constant light chain region is of SEQ ID NO. 50.

In some embodiments, the said antibody, or antigen-binding fragment thereof, comprises only natural amino acids.

In some other embodiments, the said antibody, or antigen-binding fragment thereof, comprises one or more non-natural amino acids.

In some embodiments, the said antibody, or antigen-binding fragment thereof, is a secretory antibody, preferably a secretory IgA.

In some embodiments of the said antibody, or of the antigen-binding fragment thereof, the said heavy chain variable domain is associated with IgG, including but not limited to IgG1 or IgA constant region, preferably, wherein the antibody, when associated with IgA constant region may further comprises a J chain and/or secretory component.

In some embodiments of the said antibody, or of the antigen-binding fragment thereof, the constant region comprises mutation(s) and/or modification(s) that silence antibody effector functions and/or modulate antibody half-life in vivo or an antibody function in vivo.

In some embodiments the said antibody, or the antigen-binding fragment thereof, comprises an IgA natural or mutated constant region.

In some embodiments the said antibody, or the antigen-binding fragment thereof, comprises a IgG1 natural or mutated constant region or with natural or a modified glycosylation.

In some embodiments, the said antibody is a recombinant human monoclonal antibody, preferably of IgG1 or IgA isotype.

In some embodiments, the said antibody is of the IgA isotype and is a polymeric or secretory IgA, preferably of any species, including human.

In some embodiments, the said antibody, or antigen-binding fragment thereof, binds to recombinant SARS-CoV-2 RBD domain of the Spike protein from the (i) Wuhan variant of SEQ ID NO. 78, (ii) Delta variant of SEQ ID NO. 79, (iii) BA.2 variant of SEQ ID NO. 80, (iv) BA.2.75.2 variant of SEQ ID NO. 81, (v) BA 4/5 variant of SEQ ID NO. 82, (vi) BQ.1.1. variant of SEQ ID NO. 83, (vii) XBB.1.5. variant of SEQ ID NO. 84, (viii) XBB.1.16 variant of SEQ ID NO. 85, (ix) EG.5 variant of SEQ ID NO. 86 (x) BA.2.66 variant of SEQ ID NO. 87 and JN-1 variant of SEQ ID NO. 88.

In some embodiments, the said antibody, or antigen-binding fragment thereof, neutralizes at least one SARS-CoV-2 selected from the isolates D614G, XBB.1.5, XBB.1.16, EG.5.1 and JN-1.

In some embodiments, the said antibody, or antigen-binding fragment thereof, neutralizes at least one SARS-CoV-2 related virus. As used herein, the term SARS-CoV-2 related virus encompasses viruses which whole genome sequence has at least 80, 81, 82, 83, 84, 85, 86, 87, 88, 89, 90, 91, 92, 93, 94, 95, 96, 97, 98, 99% identity with whole genome sequence of SARS-CoV-2. In a preferred embodiment, the term SARS-CoV-2 related virus excludes SARS-CoV-1. In some embodiments, the at least one SARS-CoV-2 related virus comprises or consists in a SARS-CoV-2-related bat coronavirus or a SARS-CoV-2-related pangolin coronavirus. In some embodiments, the at least one SARS-CoV-2 related virus comprises or consists in a SARS-CoV-2-related pangolin coronavirus, selected from the isolates pCoV- GD01 and GX_P2V. In a preferred embodiment, the at least one SARS-CoV-2 related virus comprises or consists in GX_P2V.

In some embodiments, the said antibody, or antigen-binding fragment thereof, has limited predicted reactivity to human proteins, limited self-reactivity as compared to control antibody, and/or limited polyreactivity as compared to control antibody.

In some embodiments, the said antibody, or antigen-binding fragment thereof, is produced in a prokaryotic or eukaryotic recombinant system or in a synthetic system.

In some embodiments, the said antibody, or antigen-binding fragment thereof, is produced in a prokaryotic recombinant system.

In some embodiments, the said antibody, or antigen-binding fragment thereof, is produced recombinantly and comprises a non-native human glycosylation pattern and/or a non-human glycosylation pattern.

In some embodiments, the said antibody, or antigen-binding fragment thereof, further comprises a detectable label.

In some embodiments, the said antibody, or antigen-binding fragment thereof, is comprised in an immunoconjugate, such as an immunoconjugate wherein the said antibody is conjugated with another moiety, such as another moiety selected from another antibody, including another anti-SARS-CoV-2 antibody, a cytotoxic moiety (to form an ADC), a cell-penetrating compound or a tissue-penetrating compound.

The present disclosure also relates to a nucleic acid encoding an antibody or antigen-binding fragment thereof, according to any one of the preceding claims; preferably comprising at least a nucleic acid sequence encoding the heavy and/or light chain of said antibody or antigen-binding fragment thereof. In some embodiments, the said nucleic acid is mRNA, preferably modified mRNA. In some other embodiments, the said nucleic acid is DNA.

The present disclosure further pertains to an expression vector for the recombinant production of an antibody or antigen-binding fragment as disclosed herein in a host cell, the said expression vector comprising at least one nucleic acid encoding said antibody as described herein.

The present disclosure also concerns a host cell comprising an expression vector as disclosed herein or a nucleic acid as described herein. In some embodiments, the host cell is an antibody producing cell-line stably transformed with the expression vector. In some embodiments, the host cell is a eukaryotic cell; preferably chosen from a yeast cell, an insect cell and a mammalian cell.

The present disclosure also relates to a method of production of the antibody or antigen-binding fragment as disclosed hereon, comprising: (i) culturing the host cell as described herein for expression of said antibody or antigen-binding fragment by the host cell; and optionally (ii) recovering the antibody or antigen-binding fragment; and (iii) purifying said antibody or antigen-binding fragment thereof.

The present disclosure also pertains to a pharmaceutical composition, comprising the antibody as described herein, or antigen-binding fragment thereof, or the nucleic acid or vector as disclosed herein, and at least one of a pharmaceutically acceptable carrier, an adjuvant, and a preservative. The said pharmaceutical composition may be adapted for administration by any route, which includes, without being limited to, intravenous, intramuscular, subcutaneous, and intranasal routes.

In some embodiments, the pharmaceutical composition comprises the nucleic acid or vector as disclosed herein and the nucleic acid is mRNA, in particular modified mRNA; preferably formulated in a vesicle or particle, in particular a lipid nanoparticle (LNP).

The present disclosure further concerns the pharmaceutical composition described herein for use as a medicament; in particular for use in a method for preventing and/or reducing the likelihood of occurrence and/or treating a SARS-CoV-2 infection and associated COVID-19 disease.

In some embodiments, the pharmaceutical composition is adapted for administration by any route, such as a route selected from intravenous route, intramuscular route, subcutaneous route, intranasal route, by aerosol and by infusion such as by rectal infusion, epidural infusion and intraperitoneal infusion.

The present disclosure also pertains to the antibody described herein, or antigen-binding fragment thereof, the nucleic acid or vector disclosed herein, or the pharmaceutical composition according to the disclosure, for use as a medicament; in particular for use in a method for preventing and/or reducing the likelihood of occurrence and/or treating a SARS-CoV-2 infection and associated COVID-19 disease.

This disclosure also relates to the antibody described herein, or antigen-binding fragment thereof, the nucleic acid or vector disclosed herein, or the pharmaceutical composition according to the disclosure, for use as a medicament for a human mammal.

This disclosure also concerns the antibody described herein, or antigen-binding fragment thereof, the nucleic acid or vector disclosed herein, or the pharmaceutical composition according to the disclosure, for use as a medicament in combination with a vaccine against a Coronaviridae infection, in particular of a SARS-CoV-2 infection.

This disclosure further relates to the antibody described herein, or antigen-binding fragment thereof, the nucleic acid or vector disclosed herein, or the pharmaceutical composition according to the disclosure, for use as a medicament in combination with antibodies reacting with other SARS-Cov2 epitopes, and/or with other pathogenic viruses.

This disclosure further relates to the antibody described herein, or antigen-binding fragment thereof, the nucleic acid or vector disclosed herein, or the pharmaceutical composition according to the disclosure, for use as a medicament in combination with antibodies reacting with another virus, such as a virus selected from a BK virus, a Respiratory Syncytial Virus (RSV), a Herpes Virus Simplex (HSV), an Epstein-Barr virus (EBV) a cytomegalovirus (CMV) an influenza virus, a parainfluenza virus, a metapneumovirus and a distinct coronavirus.

This disclosure further pertains to the antibody described herein, or antigen-binding fragment thereof, the nucleic acid or vector disclosed herein, or the pharmaceutical composition according to the disclosure, for use as a medicament in combination with a second antibody which specifically neutralizes the Severe Acute Respiratory Syndrome-related Coronavirus 2 (SARS-CoV-2), said second antibody being not a competitive inhibitor of binding to the RBD with the first antibody.

This disclosure further concerns the antibody described herein, or antigen-binding fragment thereof, the nucleic acid or vector disclosed herein, or the pharmaceutical composition according to the disclosure, for use as a medicament in combination with a second antibody which specifically binds to a viral Spike protein receptor-binding domain (RBD) of a Severe Acute Respiratory Syndrome-related Coronavirus 2 (SARS-CoV-2), said second antibody being not a competitive inhibitor of binding to the RBD with the first antibody.

This disclosure further relates to the antibody described herein, or antigen-binding fragment thereof, the nucleic acid or vector disclosed herein, or the pharmaceutical composition according to the disclosure, for use as a medicament in combination with a second antibody which specifically binds to a viral Spike protein receptor-binding domain (RBD) of a Severe Acute Respiratory Syndrome-related Coronavirus 2 (SARS-CoV-2), said second antibody being a class 2 or class 3 anti-SARS-CoV2 Spike protein antibody.

This disclosure further pertains to the antibody described herein, or antigen-binding fragment thereof, the nucleic acid or vector disclosed herein, or the pharmaceutical composition according to the disclosure, for use as a medicament in combination with a second antibody selected from the group of at least one of the following reference antibodies: Adintrevimab, Cilgavimab, Imdevimab, and Sotrovimab.

Adintrevimab has (i) a heavy chain variable domain of SEQ ID NO. 90 and (ii) a light chain variable domain of SEQ ID NO. 91. Cilgavimab has (i) a heavy chain variable domain of SEQ ID NO. 92 and (ii) a light chain variable domain of SEQ ID NO. 93. Indevimab has (i) a heavy chain variable domain of SEQ ID NO. 94 end (ii) a light chain variable domain of SEQ ID NO. 95. Sotrovimab has (i) a heavy chain variable domain of SEQ ID NO. 96 and (ii) a light chain variable domain of SEQ ID NO. 97.

This disclosure further pertains to the antibody described herein, or antigen-binding fragment thereof, the nucleic acid or vector disclosed herein, or the pharmaceutical composition according to the disclosure, for use as a medicament in combination with a second antibody selected from the group of at least one of the following reference antibodies: (i) antibodies directed against RBD such as Adintrevimab, VYD222 antibody (from Invivyd, Inc. Company), SA55 antibody (from Sinovac Biotech Co. Ltd company), Cilgavimab, Imdevimab, and Sotrovimab, (ii) anti-S2 directed against the fusion peptide such as C77G12 antibody (disclosed in Low et al., 2022, Science, Vol. 377 (6607): 735-742), 76E1 antibody (disclosed in Sun et al., 2022, Nat Microbiol, Vol. 7 (7): 1063-1074) or COV4462 (Dacon et al., 2022, Science, Vol. 377 (6607): 728-735), (iii) antibodies directed against the HR2 region such as Cv2.3132 (disclosed in Plachais et al., 2022, J Exp Med, Vol. 219 (7): e20220638, in EP23305528.4 and PCT/IB2022/000108) and (iv) antibodies directed against the S2 stem helix.

It is also disclosed herein a pharmaceutical composition comprising:

(i) an antibody described herein, or antigen-binding fragment thereof, the nucleic acid or vector disclosed herein, or a pharmaceutical composition according to the disclosure, and (ii) an antibody selected from the group of at least one of the following reference antibodies: Adintrevimab, Cilgavimab, Imdevimab, and Sotrovimab.

It is further disclosed herein a pharmaceutical composition comprising:

(i) an antibody described herein, or antigen-binding fragment thereof, the nucleic acid or vector disclosed herein, or a pharmaceutical composition according to the disclosure, and (ii) an antibody selected from the group of at least one of the following reference antibodies: (i) antibodies directed against RBD selected from Adintrevimab, VYD222 antibody, SA55 antibody, Cilgavimab, Imdevimab, and Sotrovimab, (ii) anti-S2 antibodies directed against the fusion peptide such as C77G12 antibody, 76E1 antibody or COV4462 antibody, (iii) antibodies directed against the HR2 region, such as Cv2.3132 and (iv) antibodies directed against the S2 stem helix.

The present disclosure also related to the use of an antibody described herein, or antigen-binding fragment thereof, the nucleic acid or vector disclosed herein, or a pharmaceutical composition according to the disclosure for the manufacture of a medicament for the prevention or treatment of SARS-CoV-2 infection and associated COVID-19 disease.

It is also disclosed herein a kit comprising an antibody described herein, or antigen-binding fragment thereof, the nucleic acid or vector disclosed herein, or a pharmaceutical composition according to the disclosure.

In some embodiments, the said kit further comprises an antibody selected from the group of at least one of the following reference antibodies: Adintrevimab, Cilgavimab, Imdevimab, and Sotrovimab.

In some embodiments, the said kit further comprises an antibody selected from the group of at least one of the following reference antibodies: (i) antibodies directed against RBD selected from Adintrevimab, VYD222 antibody, SA55 antibody, Cilgavimab, Imdevimab, and Sotrovimab, (ii) anti-S2 antibodies directed against the fusion peptide such as C77G12 antibody, 76E1 antibody or COV4462 antibody, (iii) antibodies directed against the HR2 region, such as Cv2.3132 and (iv) antibodies directed against the S2 stem helix.

This disclosure also relates to a method for the detection of a SARS-CoV-2 in a sample comprising: contacting said sample with an antibody as disclosed herein, or antigen-binding fragment thereof, and detecting the antigen-antibody complexes formed, thereby detecting the presence. absence or level of SARS-CoV-2 in the sample. In some embodiments, the sample is a biological or environmental sample. In some embodiments, the sample is from a human or non-human mammal.

In some embodiments, the sample is a biological sample from a subject suspected to be contaminated with SARS-CoV-2 and the method is for the diagnosis of SARS-CoV-2 infection and associated COVID-19 disease.

In some embodiments, the sample is a biological sample from a COVID-19 patient before or during treatment of COVID-19 disease and the method is for the monitoring of treatment of COVID-19 disease.

This disclosure also pertains to a method of reducing the risk of developing SARS-CoV-2-associated disease in a subject, comprising administering an effective amount of an antibody as disclosed herein, or antigen-binding fragment thereof, a nucleic acid or vector disclosed herein, or a pharmaceutical composition according to the disclosure, to the subject. According to some embodiments of the said method, the risk of hospitalization is reduced. According to some embodiments of the said method, the risk of death is reduced. According to some embodiments of the said method, the risk of graft rejection is reduced.

The present disclosure further concerns the antibody described herein, or antigen-binding fragment thereof, the nucleic acid or vector disclosed herein, or the pharmaceutical composition according to the disclosure, for use in a method for preventing and/or reducing the likelihood of occurrence of a Coronaviridae infection; in particular a SARS-CoV-2 infection.

Is also disclosed herein the antibody described herein, or antigen-binding fragment thereof, the nucleic acid or vector disclosed herein, or the pharmaceutical composition according to the disclosure, for use in a method for preventing and/or reducing the likelihood of occurrence of a complication of a Coronaviridae infection, in particular of a respiratory, nervous, gastrointestinal or cardiovascular complication of a Coronaviridae infection; in particular of a SARS-CoV-2 infection.

Is further disclosed herein the antibody described herein, or antigen-binding fragment thereof, the nucleic acid or vector disclosed herein, or the pharmaceutical composition according to the disclosure, for use in a method for preventing and/or reducing the likelihood of occurrence of a severe acute respiratory complication of a Coronaviridae infection; in particular of a SARS-CoV-2 infection.

This disclosure also relates to the antibody described herein, or antigen-binding fragment thereof, the nucleic acid or vector disclosed herein, or the pharmaceutical composition according to the disclosure, for use in a method for preventing and/or reducing the likelihood of occurrence of a severe acute respiratory complication of a Coronaviridae infection; in particular of a SARS-CoV-2 infection.

This disclosure also pertains to the antibody described herein, or antigen-binding fragment thereof, the nucleic acid or vector disclosed herein, or the pharmaceutical composition according to the disclosure, for use in a method for preventing and/or reducing the likelihood of occurrence of a Coronaviridae infection in an individual, said individual being characterized in that
- the individual has not been administered a vaccine against the said Coronaviridae infection; or
- the individual is not responding to the said vaccine; or
- the individual's level of antibodies directed against the Coronaviridae infection is at or below a protecting threshold level.

Is further disclosed herein the antibody described herein, or antigen-binding fragment thereof, the nucleic acid or vector disclosed herein, or the pharmaceutical composition according to the disclosure, for use in a method for improving an immune response against a Coronaviridae virus; in particular of a SARS-CoV-2 infection.

This disclosure also concerns the antibody described herein, or antigen-binding fragment thereof, the nucleic acid or vector disclosed herein, or the pharmaceutical composition according to the disclosure, for use in a method for improving an immune response against a viral Spike protein receptor-binding domain (RBD) of a Coronaviridae virus; or a fragment thereof.

The present disclosure also pertains to a method of treating a SARS-CoV-2-associated disease in a subject, comprising administering an effective amount of the antibody according to the disclosure, or antigen-binding fragment thereof, to the subject. In some embodiments, the risk of developing severe disease is reduced by the treatment. In some embodiments, the subject is hospitalized.

The present disclosure also pertains to a method of treating a SARS-CoV-2-associated disease in a subject, comprising administering an effective amount of the antibody according to the disclosure, or antigen-binding fragment thereof, in combination with an antibody selected from Adintrevimab, Cilgavimab, Imdevimab, and Sotrovimab.

The present disclosure also pertains to a method of treating a SARS-CoV-2-associated disease in a subject, comprising administering an effective amount of the antibody according to the disclosure, or antigen-binding fragment thereof, in combination with an antibody selected from (i) antibodies directed against RBD selected from Adintrevimab, VYD222 antibody, SA55 antibody, Cilgavimab, Imdevimab, and Sotrovimab, (ii) anti-S2 antibodies directed against the fusion peptide such as C77G12 antibody, 76E1 antibody or COV4462 antibody, (iii) antibodies directed against the HR2 region, such as Cv2.3132 and (iv) antibodies directed against the S2 stem helix.

According to some embodiments of the method above, the subject is at risk of developing a SARS-CoV-2-associated disease, more particularly a subject with concurrent underlying conditions such as obesity, diabetes, cancer, under immunosuppressive therapy, primary immune deficiency or unresponsive to vaccines.

The present disclosure also relates to a medical device, comprising the antibody described herein, or antigen-binding fragment thereof, the nucleic acid or vector disclosed herein, or the pharmaceutical composition according to the disclosure, preferably in a form suitable for administration by injection or inhalation.

Abscissa: from left to right of the figure: (i) SPK002 antibody (parental version Cv2.3194 described in WO 2022/228827), (ii) A1 antibody, (iii) A2 antibody, (iv) A3 antibody, (v) A4 antibody, (vi) A5 antibody, (vii) A6 antibody, (viii) B1 antibody, (ix) B2 antibody, (x) C1 antibody, (xi) C2 antibody, (x) C3 antibody, (xi) positive control highly polyreactive ED38 antibody and (xii) negative control mG053 antibody.

Figure 2:
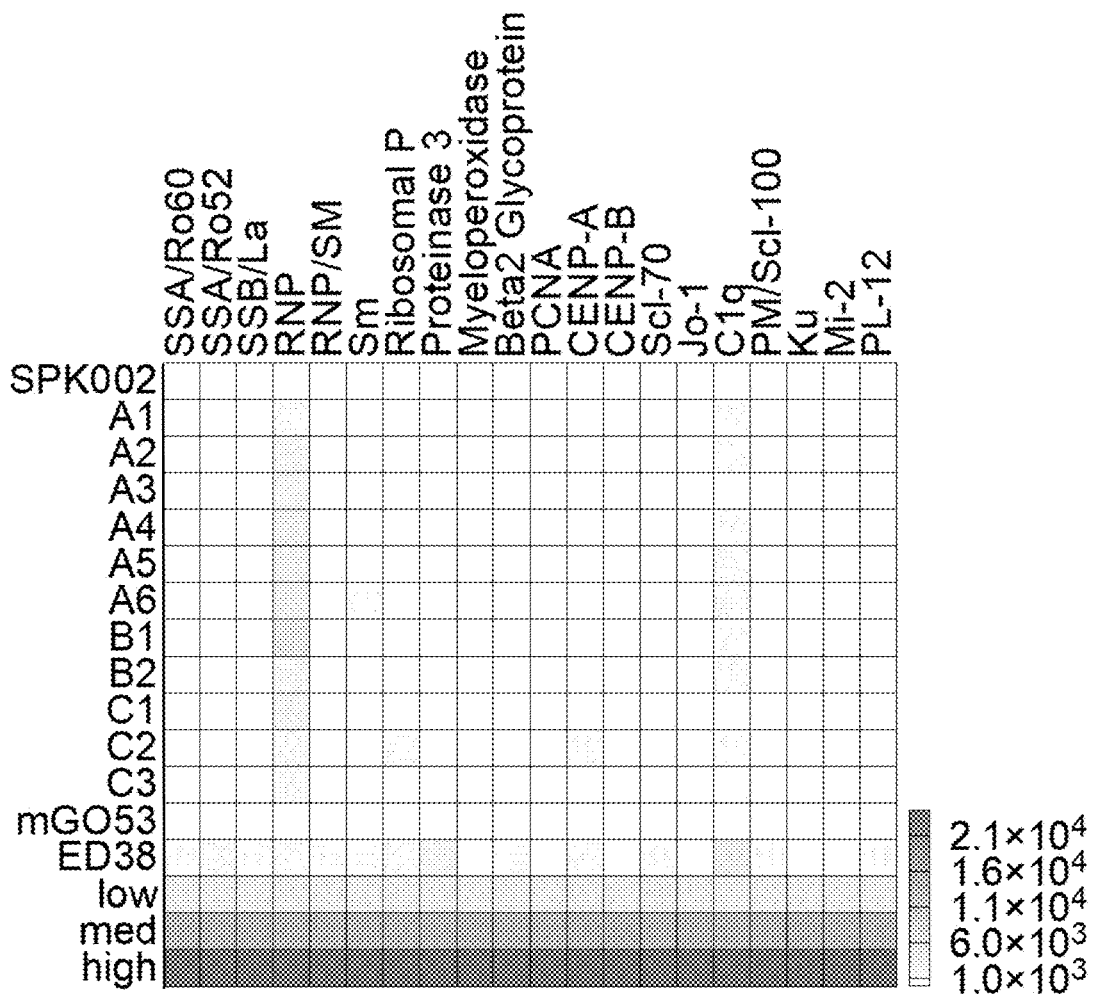

FIG. 2. Multiplex ELISA assay (Milliplex® Human autoimmune autoantibody panel kit) with a variety of the antibodies described herein.

Ordinate: from the top to the bottom: (i) PK002 antibody (parental version Cv2.3194 described in WO 2022/228827), (ii) A1 antibody, (iii) A2 antibody, (iv) A3 antibody, (v) A4 antibody, (vi) A5 antibody, (vii) A6 antibody, (viii) B1 antibody, (ix) B2 antibody, (x) C1 antibody, (xi) C2 antibody, (x) C3 antibody, (xi) negative control mG053 antibody, (xii) positive control highly polyreactive ED38 antibody, (xiii) low positive control of the kit, (xiv) medium positive control of the kit and (xv) high positive control of the kit.

Abscissa: tested antigens, from the left to the right: (i) SSA/Ro60, (ii) SSA/Ro52, (iii) SSB/La, (iv) RNP, (v) RNP/SM, (vi) Sm, (vii) Ribosomal P, (viii) Proteinase 3, (ix) Myeloperoxidase, (x) Beta2 Glycoprotein, (xi) PCNA, (xii) CENP-A, (xiii) CENP-B, (xiv) Scl-70, (xv) Jo-1, (xvi) C1q, (xvii) PM/Scl-100, (xviii) Ku, (xix) Mi-2 and (xx) PL-12.

FIG. 3. RBD binding of a variety of antibodies described herein.

FIG. 3 illustrates a heatmap comparing the ELISA binding of a plurality of antibodies disclosed herein to the RBD of selected SARS-CoV-2 variants. Darker colors indicate lower binding values while lighter colors indicate higher binding values. The numerical values are the area under the curve (AUC) values determined from the ELISA binding analyses.

On the left part of the figure, the SARS-CoV-2 variants tested are indicated, respectively, from the top line to the bottom line, (i) Wuhan, (ii) Delta, (iii) BA.2., (iv) BA.2.75.2, (v) BA.4/5, (vi) BQ.1.1, (vii) XBB.1.5, (viii) XBB.1.16, (ix) EG.5, (x) BA.2.86 and (xi) JN-1.

On the top of the figure, the various antibodies tested are indicated, respectively from the left to the right, (i) SPK002 antibody (parental version Cv2.3194 described in WO 2022/228827), (ii) A1 antibody, (iii) A2 antibody, (iv) A3 antibody, (v) A4 antibody, (vi) A5 antibody, (vii) A6 antibody, (viii) B1 antibody, (ix) B2 antibody, (x) C1 antibody, (xi) C2 antibody and (xii) C3 antibody.

The numerical values indicated in each square are the Area Under the Curve (AUC) binding values.

FIG. 4. RBD-ACE-2 blocking assay.

FIG. 4 illustrates a heatmap comparing the RBD-ACE2 blocking capacity of a plurality of RBD-specific monoclonal antibodies for the RBD proteins originating from various SARS-CoV-2 variants. Darker colors indicate lower blocking values while lighter colors indicate higher blocking values. The numerical values are percent blocking values determined from the ELISA binding analyses On the left part of the figure, the SARS-CoV-2 variants tested are indicated, respectively, from the top line to the bottom line, (i) Wuhan, (ii) Delta, (iii) BA.2., (iv) BA.2.75.2, (v) BA.4/5, (vi) BQ.1.1, (vii) XBB.1.5, (viii) XBB.1.16, (ix) EG.5, (x) BA.2.86 and (xi) JN.1.

On the top of the figure, the various antibodies tested are indicated, respectively from the left to the right, (i) SPK002 antibody (parental version Cv2.3194 described in WO 2022/228827), (ii) A1 antibody, (iii) A2 antibody, (iv) A3 antibody, (v) A4 antibody, (vi) A5 antibody, (vii) A6 antibody, (viii) B1 antibody, (ix) B2 antibody, (x) C1 antibody, (xi) C2 antibody and (xii) C3 antibody.

The numerical values indicated in each square are the percentage of blocking the binding of ACE2 ectodomain to the RBD of the Spike protein.

FIG. 5. S-Fuse neutralization assay.

FIG. 6 illustrates the half maximal inhibitory concentration ($IC_{50}$) neutralization values (in µg/mL) measured for a variety of anti-RBD monoclonal antibodies against a plurality of SARS-CoV-2 variants. The $IC_{50}$ values shown in FIG. 6 are calculated from the neutralization curves presented in the graphs illustrated in FIG. 5.

On the left of the figure, the SARS-CoV-2 variants tested are indicated, respectively from the top line to the bottom line: (i) D614G, (ii) XBB.1.5, (iii) XBB.1.16, (iv) BA.2.86, (v) EG.5.1 and (vi) JN.1.

On the top of the figure, the various anti-RBD monoclonal antibodies tested are indicated, from the left raw to the right raw, respectively: (i) SPK002 antibody (described in WO 2022/228827), (ii) A1 antibody, (iii) A2 antibody, (iv) A3 antibody, (v) A4 antibody, (vi) A5 antibody, (vii) A6 antibody, (viii) B1 antibody, (ix) B2 antibody, (x) C1 antibody, (xi) C2 antibody, (xii) C3 antibody.

The numerical values indicated in each square are the $IC_{50}$ values, as expressed in µg/mL FIG. 6 illustrates a summary of the amino acid mutations present in the heavy chain variable domain (VH) and the light chain variable domain (VL) of each of the A1, A2, A3, A4, A5, A6, B1, B2, C1, C2 and C3 antibodies, when compared to the corresponding VH and VL domains of the parent SPK002 antibody described in WO 2022/228827 (upper line). The "chain position" numbers are the respective amino acid positions in the VH and VL domains where amino acid differences with the corresponding VH and VL of the parent SPK002 antibody are located.

DETAILED DESCRIPTION OF THE INVENTION

The disclosure provides antibodies, including antigen-binding fragments thereof, against SARS-CoV-2 Spike protein, in particular recombinant human monoclonal antibodies against SARS-CoV-2 Spike protein, binding to SARS-CoV-2 spike protein of a large spectrum of SARS-CoV-2 variants, including SARS-CoV-2 variants of the BA.2.75.2., BQ.1.1., XBB.1.16, EG.5. and BA.2.86 sublineages.

The antibodies of interest disclosed herein derive from the parent antibody termed "Cv2.3194" which is described in the PCT application published under N° WO 2022/228827. Importantly, the inventors have shown herein that the identity of the amino acid located at position 71 of the heavy chain variable domain of the novel antibodies directed against the SARS-CoV-2 spike protein disclosed herein, according to the KABAT numbering, is determinant for the binding of these novel antibodies to a large spectrum of SARS-CoV-2 variants. Unexpectedly, the inventors have found that a high binding of these novel antibodies to the RBD from numerous SARS-CoV-2 variants is, at least partly, due to the replacement of an arginine residue located at position 71 of the heavy chain variable domain of the parent antibody "Cv2.3194" (also termed SPK002 herein) by an amino acid residue avoiding steric hindrance and/or electrostatic repulsion, such as an amino acid residue selected from Alanine, Tyrosine and Threonine. Antibody Cv2.3194 (also termed SPK002 herein) has (i) a heavy chain variable domain of SEQ ID NO. 73 and (ii) a light chain variable domain of SEQ ID NO. 74.

Without wishing to be bound by any particular theory, the inventors believe that, upon recognition of the RBD of the Spike protein of a SARS-CoV-2 virus by an antibody disclosed herein, the amino acid located at position 71 of the heavy chain variable domain thereof is positioned in the vicinity of the Lysine amino acid located at position 486 of the RBD protein, present on post-BA.5 variants. The inventors have found that the presence of an arginine residue at position 71 of the heavy chain variable domain led to a steric and/or electrostatic "clash" with the amino acid located at position 486 of the RBD protein, which "clash" affecting the binding of the antibody to the RBD of a plurality of SARS-CoV-2 variants, and especially affecting the binding of the antibody to the RBD of a plurality of SARS-CoV-2 recently emerging variants.

Surprisingly, the inventors have shown that the replacement of the arginine residue located at position 71 of the heavy chain variable domain of the parent "Cv2.3194" antibody (also termed SPK002 herein) by an amino acid residue having a reduced steric and/or electrostatic hindrance, the resulting variant antibody (i) is able to bind to the RBD of various SARS-CoV-2 variants that are weakly bound by the parent antibody while (ii) maintaining its binding activity to the RBD SARS-CoV-2 variants that were recognized by the parent antibody. Thus, the novel anti-RBD antibodies disclosed herein form a family of wide spectrum antibodies, that can be used for preventing a SARS-CoV-2 disease in subjects as well as for treating subjects infected with a SARS-CoV-2 virus, almost irrespective of the SARS-CoV-2 variant lineage thereof.

Further, as it is shown in the examples, the anti-RBD monoclonal antibodies disclosed herein have a reduced binding ability towards non-SARS-CoV-2 proteins and thus do not show binding to self-antigens, which ensures that these novel antibodies will not induce undesirable side effects, when used in subjects for prophylactic or therapeutic purposes.

The present disclosure relates to an antibody directed against the viral Spike protein receptor binding-domain (RBD) of Severe Acute Respiratory Syndrome-related Coronavirus 2 (SARS-CoV-2), or antigen-binding fragment thereof, comprising:

(i) a heavy chain variable domain comprising:
a HCDR1 of SEQ ID NO. 1,
a HCDR2 selected from SEQ ID NO. 2 and SEQ ID NO. 20,
a HCDR3 of SEQ ID NO. 3,
or variants thereof comprising up to 1 amino acid mutation in the sequence of 1, 2 or 3 CDRs,
(ii) a light chain variable domain comprising:
a LCDR1 selected from SEQ ID NO. 9, SEQ ID NO. 23, SEQ ID NO. 24 and SEQ ID NO. 25
a LCDR2 of SEQ ID NO. 10,
a LCDR3 selected from SEQ ID NO. 11, SEQ ID NO. 27,
or variants thereof comprising up to 1 amino acid mutation in the sequence of 1, 2 or 3
CDRs,
and
(iii) a HFR3 of the amino acid sequence RFTISXDNSKNTLYLQMNSLRAEDTAVYYCAR (SEQ ID NO. 28) wherein X means an amino acid selected from Alanine, Tyrosine and Threonine.

In preferred embodiments of the said antibody, or antigen-binding fragment thereof, the HFR3 is selected from SEQ ID NO. 6, SEQ ID NO. 21 and SEQ ID NO. 22.

Definitions

As used herein, the term "SARS-CoV-2 Spike(S) protein or glycoprotein" has its general meaning in the art and refers to a trimeric class I viral fusion protein (S trimer or tri-S) having the canonical sequence reported under accession number UniProtK P0DTC2. Based on structure predictions, signal peptide (SP) is from positions 1 to 12; ectodomain (extracellular domain) from positions 13 to 1213; transmembrane domain I from positions 1214 to 1234 and cytoplasmic domain from positions 1235 to 1273 of UniProtK P0DTC2. S1 sub-unit is from positions 13 to 685, receptor-binding domain (RBD or RBD domain) from positions 319 to 541 and S2 sub-unit from positions 686 to 1273. However, the positions of the domains or sub-units may vary slightly (+1 to +15 and −1 to −15) relative to the indicated positions. For example, the signal peptide may be from positions 1 to 15, the ectodomain from positions 13 to 1208, S1 protein from positions 16 to 681, and RBD from positions 331 to 530 of the reference sequence UniProtK P0DTC2.

As used herein, SARS-CoV-2 refers to SARS-CoV-2 isolate Wuhan-Hu-1 and any isolate, strain, lineage, sublineage or variant thereof that is neutralized by the antibodies according to the invention. SARS-CoV-2 isolate Wuhan-Hu-1, which is used as SARS-CoV-2 reference is also referred to as BetaCoV_Wuhan_WIV04_2019 (EPI_ISL_402124) or BetaCoV_Wuhan_IVDC-HB-05_2019 EPI_ISL_402121. Non-limiting examples of SARS-CoV-2 variant or lineage which may be neutralized by the antibodies according to the present invention include SARS-CoV-2 variants Omicron Delta, BA.2, BA.2.75.2, BA.4/5, BQ.1.1., XBB1.5, XBB1.16, EG.5., BA.2.86 and JIN-1. The variant may comprise other mutations in the RBD, the Spike protein or any other viral proteins, which may not prevent neutralization by the antibodies according to the present disclosure.

The term "antibody" as used herein refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies of any isotype or species.

The term "antibody", as used herein and unless stated otherwise, may thus encompass whole antibody molecules, but also antigen-binding fragments, or chain fragment thereof.

In natural antibodies of rodents and primates, two heavy chains are linked to each other by disulfide bonds, and each heavy chain is linked to a light chain by a disulfide bond. There are two types of light chains, lambda ($\lambda$) and kappa ($\kappa$). There are five main heavy chain classes (or isotypes) which determine the functional activity of an antibody molecule: IgM, IgD, IgG, IgA and IgE. In humans there are four subclasses of IgG: IgG1, IgG2. IgG3 and IgG4 (numbered in order of decreasing concentration in serum). IgA exists in two subclasses, IgA1 and IgA2. Both IgA1 and IgA2 have been found in external secretions (secretory IgA), where IgA2 is more prominent than in the blood (serum IgA). Each chain contains distinct sequence domains. In typical IgG antibodies, the light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). Secretory IgA are polymeric: 2-4 IgA monomers are linked by two additional chains: the immunoglobulin joining (J) chain(s) and secretory component (SC). The J chain binds covalently to two IgA molecules through disulfide bonds between cysteine residues. The secretory component is a proteolytic cleavage product of the extracellular part of the polymeric immunoglobulin receptor (pIgR) which binds to J-chain containing polymeric Ig. Polymeric IgA (mainly the secretory dimer) is produced by plasma cells in the lamina propria adjacent to mucosal surfaces. It binds to the polymeric immunoglobulin receptor on the basolateral surface of epithelial cells, and is taken up into the cell via endocytosis. The receptor-IgA complex passes through the cellular compartments before being secreted on the luminal surface of the epithelial cells, still attached to the receptor. Proteolysis of the receptor occurs, and the dimeric IgA molecule, along with a portion of the receptor known as the secretory component—known as sIgA, are free to diffuse throughout the lumen.

The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from non-hypervariable or framework regions (FR) can participate in the antibody binding site or influence the overall domain structure and hence the combining site.

Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, typically includes six CDRs, comprising the CDRs set from each of a heavy and a light chain V region. Framework Regions (FRs) refer to amino acid sequences interposed between CDRs. Accordingly, the variable regions of the light and heavy chains typically comprise 4 framework regions and 3 CDRs of the following sequence: FR1-CDR1-FR2-CDR2-FR3-CDR3-FR4.

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (Kabat et al., 1992, hereafter "Kabat et al."). This numbering system is used in the present specification. The Kabat residue designations do not always correspond directly with the linear numbering of the amino acid residues in SEQ ID sequences. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence. The CDRs of the heavy chain variable domain are located at residues 31-35 (H-CDR1), residues 50-65 (H-CDR2) and residues 95-102 (H-CDR3) according to the Kabat numbering system. The CDRs of the light chain variable domain are located at residues 24-34 (L-CDR1), residues 50-56 (L-CDR2) and residues 89-97 (L-CDR3) according to the Kabat numbering system. The predicted CDRs of some anti-SARS-CoV-2 antibodies, such as Cv2.3194 (which may also be termed "SPK002" herein), A1, A2, A3, A4, A5, A6, B1, B2, C1, C2 and C3 are described herein.

The term "monoclonal antibody" as used herein refers to a preparation of antibody molecules of single specificity. A monoclonal antibody displays a single binding specificity and affinity for a particular epitope. Accordingly, the term "human monoclonal antibody" refers to an antibody displaying a single binding specificity which has variable and constant regions derived from or based on human germline immunoglobulin sequences or derived from completely synthetic sequences. The method of preparing the monoclonal antibody is not relevant for the binding specificity.

As used herein, the term "recombinant antibody" refers to antibodies which are produced, expressed, generated or isolated by recombinant means, such as antibodies which are expressed using a recombinant expression vector transfected into a host cell; antibodies isolated from a recombinant combinatorial antibody library; antibodies isolated from an animal (e.g. a mouse) which is transgenic due to human immunoglobulin genes; or antibodies which are produced, expressed, generated or isolated in any other way in which particular immunoglobulin gene sequences (such as human immunoglobulin gene sequences) are assembled with other DNA sequences. Recombinant antibodies include, for example, chimeric and humanized antibodies. In some embodiments a recombinant human antibody of this invention has the same amino acid sequence as a naturally-occurring human antibody but differs structurally from the naturally occurring human antibody. For example, in some embodiments the glycosylation pattern is different as a result of the recombinant production of the recombinant human antibody. In some embodiments the recombinant human antibody is chemically modified by addition or subtraction of at least one covalent chemical bond relative to the structure of the human antibody that occurs naturally in humans.

Generally, an antibody according to the invention may contain only natural amino acids, most preferably L-amino acids. In some embodiments of an antibody according to the present disclosure, the said antibody may contain one or more non-natural amino acids.

The term "amino acid" or "any amino acid" as used here refers to any and all amino acids, including naturally occurring amino acids (e.g., a-amino acids), unnatural amino acids, modified amino acids, and non-natural amino acids. It includes both D- and L-amino acids. Natural amino acids include those found in nature, such as, e.g., the 23 amino acids that combine into peptide chains to form the building-blocks of a vast array of proteins. These are primarily L stereoisomers, although a few D-amino acids occur in bacterial envelopes and some antibiotics. The 20 "standard," natural amino acids are listed in the above tables. The "non-standard," natural amino acids are pyrrolysine (found in methanogenic organisms and other eukaryotes), selenocysteine (present in many non-eukaryotes as well as most eukaryotes), and N-formylmethionine (encoded by the start codon AUG in bacteria, mitochondria and chloroplasts). "Unnatural" or "non-natural" amino acids are non-proteinogenic amino acids (i.e., those not naturally encoded or found in the genetic code) that either occur naturally or are chemically synthesized. Over 140 natural amino acids are known and thousands of more combinations are possible. Examples of "unnatural" amino acids include β-amino acids (β3 and 2), homo-amino acids, proline and pyruvic acid derivatives, 3-substituted alanine derivatives, glycine derivatives, ring-substituted phenylalanine and tyrosine derivatives, linear core amino acids, diamino acids, D-amino acids, and N-methyl amino acids. Unnatural or non-natural amino acids also include modified amino acids. "Modified" amino acids" include amino acids (e.g., natural amino acids) that have been chemically modified to include a group, groups, or chemical moiety not naturally present on the amino acid.

As is clear to the skilled artisan, the peptide sequences disclosed herein are shown proceeding from left to right, with the left end of the sequence being the N-terminus of the peptide and the right end of the sequence being the C-terminus of the peptide.

For the most part, the names of naturally occurring and non-naturally occurring aminoacyl residues used herein follow the naming conventions suggested by the IUPAC Commission on the Nomenclature of Organic Chemistry and the IUPAC-IUB Commission on Biochemical Nomenclature as set out in "Nomenclature of α-Amino Acids (Recommendations, 1983)". To the extent that the names and abbreviations of amino acids and aminoacyl residues employed in this specification and appended claims differ from those suggestions, they will be made clear to the reader.

As used herein, the term "non-native human glycosylation pattern" refers to a glycosylation pattern (i.e. of an antibody according to the present disclosure) which is characterized in that it is produced in human cells (i.e. in vitro production; for example in vitro production in HEK cells), and which may or may not correspond to the native glycosylation pattern of a reference human antibody.

As used herein, the term "non-human glycosylation pattern" refers to a glycosylation pattern which is characterized in that it is produced in non-human cells (i.e. in vitro production in CHO cells).

The term "antigen-binding fragment" of an antibody (or simply "antibody fragment"), as used herein, refers to full length or one or more fragments of an antibody that retain the ability to specifically bind to an antigen (e.g., Spike glycoprotein of SARS-CoV-2, preferably RBD domain). It has been shown that the antigen-binding function of an antibody can be performed by fragments of a full-length antibody. Examples of binding fragments encompassed within the term "antigen-binding fragment" of an antibody include a Fab fragment, a monovalent fragment consisting of the VL, VH, CL and CH1 domains; a F(ab')₂ fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., 1989 Nature 341: 544-546), which consists of a VH domain, or any fusion proteins comprising such antigen-binding fragments. Furthermore, although the two domains of the Fv fragment, VL and VH, are coded for by separate genes, they can be joined, using recombinant methods, by a synthetic linker that enables them to be made as a single chain protein in which the VL and VH regions pair to form monovalent molecules (known as single chain Fv (scFv); see e.g., Bird et al., 1988 Science 242:423-426; and Huston et al., 1988 Proc. Natl. Acad. Sci. 85:5879-5883). Such single chain antibodies are also intended to be encompassed within the term "antigen-binding fragment" of an antibody. These antibody fragments are obtained using conventional techniques known to those of skill in the art, and the fragments are screened for utility in the same manner as are intact antibodies.

The expression "variable domain" or "variable region" of an antibody heavy or light chain are used interchangeably as the variable region of an antibody consists of a variable domain.

The phrases "an antibody recognizing an antigen (X)", "an antibody having specificity for an antigen (X)", "an anti-X antibody", "an antibody against X", and an "antibody directed against" are used interchangeably herein with the term "an antibody which binds specifically to an antigen (X)".

As used herein, "antibody" or "nucleic acid" refers to an isolated antibody or nucleic acid.

The present disclosure encompasses the therapeutic use of both the antibody or antigen-binding fragment according to the present disclosure (antibody therapy) and a nucleic acid or vector encoding said antibody or antigen-binding fragment, in particular mRNA such as modified mRNA (nucleic acid therapy).

As used herein, the term "specificity" refers to the ability of an antibody to detectably bind an epitope presented on an antigen, such as the SARS-CoV-2 Spike glycoprotein (S trimer or tri-S) which is a trimeric class I viral fusion protein, particularly the S1 subunit of S protein monomer, more particularly the SARS-CoV-2 Spike receptor-binding domain (RBD or S-RBD) while not detectably binding to (i.e., cross-reacting with) other epitopes. The specific binding of an antibody of the present disclosure to the SARS-CoV-2 Spike receptor-binding domain (RBD or S-RBD) refers to its binding to at least one of a SARS-CoV-2 Spike (S trimer or tri-S) protein, S1 subunit protein and S-RBD protein, in particular chosen from SARS-CoV-2 tri-S(SEQ ID NO: 75), S1 sub-unit (SEQ ID NO: 76), S-RBD (SEQ ID NO: 77) proteins. As the RBD is present in the Spike and S1 proteins, the specificity of an antibody for the RBD protein also implies its specificity for the Spike and S1 proteins.

Specificity can further be exhibited by, e.g., an about 10:1, about 20:1, about 50:1, about 100:1, 10.000:1 or greater ratio of affinity/avidity in binding to the specific antigen versus nonspecific binding to other irrelevant molecules (in this case the specific antigen is a SARS-CoV-2 Spike glycoprotein (tri-S), S1 sub-unit or S-RBD, particularly chosen from SARS-CoV-2 tri-S(SEQ ID NO: 75), S1 sub-unit (SEQ ID NO: 76) and S-RBD (SEQ ID NO: 77) proteins. Specificity demonstrated experimentally for at least the S-RBD protein and one non-specific antigen means that the antibody is specific to the antigen. The term "affinity", as used herein, means the strength of the binding of an antibody to an epitope.

As used herein, the term "Avidity" refers to an informative measure of the overall stability or strength of the antibody-antigen complex. It is controlled by three major factors: antibody epitope affinity; the valence of both the antigen and antibody; and the structural arrangement of the interacting parts. Ultimately these factors define the specificity of the antibody, that is, the likelihood that the particular antibody is binding to a precise antigen epitope.

For all ELISA assays, the coating step is performed overnight in PBS buffer. Washings with 0.05% Tween 20-PBS buffer are performed between each step. A blocking step of 2 h with 2% BSA, 1 mM EDTA, 0.05% Tween 20-PBS (Blocking buffer) is performed after the coating step. Antibody dilution and incubation are performed in PBS. Optical densities are measured at appropriate OD and background values given by incubation of PBS alone in coated are subtracted. OD>0.5 (cut-off value) are considered as positive.

For each of the amino acid sequences of interest, especially for each of the antibody amino acid sequences of interest, reference sequences are described herein. The present description also encompasses amino acid sequences having specific percentages of amino acid identity with a reference amino acid sequence.

As used herein, the "percentage of identity" between two amino acid sequences, or between two nucleic acid sequences, is determined by comparing both optimally aligned sequences through a comparison window.

The portion of the amino-acid sequence, or nucleic acid sequence, in the comparison window may thus include additions or deletions (for example "gaps") as compared to the reference sequence (which does not include these additions or these deletions) so as to obtain an optimal alignment between both sequences.

The terms "sequence identity" or "identity" are used interchangeably herein. For the purpose of the disclosure, it is defined here that in order to determine the percentage of sequence identity of two amino acid sequences, or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more amino acids, or nucleotides. The sequence identity is the percentage of identical matches between the two sequences over the reported aligned region. A comparison of sequences and determination of percentage of sequence identity between two sequences can be accomplished using a mathematical algorithm. The skilled person will be aware of the fact that several different computer programs are available to align two sequences and determine the identity between two sequences (Kruskal, J. B. (1983)

An overview of sequence comparison In D. Sankoff and J. B. Kruskal, (ed.), Time warps, string edits and macromolecules: the theory and practice of sequence comparison, pp. 1-44 Addison Wesley).

The percent sequence identity between two amino acid sequences, or between two nucleic acid sequences, is most preferably determined using the Needleman and Wunsch algorithm for the alignment of two sequences. (Needleman, S. B. and Wunsch, C. D. (1970) J. Mol. Biol. 48, 443-453). Both amino acid sequences, or nucleotide sequences, can be aligned by the algorithm. The Needleman-Wunsch algorithm has been implemented in the computer program NEEDLE. The NEEDLE program from the EMBOSS package can be used (version 2.8.0 or higher, EMBOSS: The European Molecular Biology Open Software Suite (2000) Rice, P. Longden, J. and Bleasby, A. Trends in Genetics 16, (6) pp 276-277, http://emboss.bioinformatics.nl/). For protein sequences EBLOSUM62 can used for the substitution matrix. For nucleotide sequence, EDNAFULL can used. The optional parameters are preferably a gap opening penalty of 10 and a gap extension penalty of 0.5. No end gap penalty is added. In the Output section, Yes has been indicated in response to the question "Brief identity and similarity" and "SRS pairwise" indicated as Output alignment format. After alignment by the program NEEDLE as described above the percentage of sequence identity between a query sequence and a sequence of the disclosure is calculated as follows: Number of corresponding positions in the alignment showing an identical amino acid, or an identical nucleotide, in both sequences divided by the total length of the alignment after subtraction of the total number of gaps in the alignment. The identity defined as herein can be obtained from NEEDLE by using the NOBRIEF option and is labeled in the output of the program as "longest-identity"

According to the present disclosure, the antibody can be selected from:

an antibody comprising:
  (i) a heavy chain variable domain, or fragment thereof, comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 6,
  (ii) a light chain variable domain, or fragment thereof, comprising (a) a LCDR1 of SEQ ID NO. 9, (b) a LCDR2 of SEQ ID NO. 10 and (c) a LCDR3 of SEQ ID NO. 11, an antibody comprising:
  (i) a heavy chain variable domain, or fragment thereof, comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 6,
  (ii) a light chain variable domain, or fragment thereof, comprising (a) a LCDR1 of SEQ ID NO. 23, (b) a LCDR2 of SEQ ID NO. 10 and (c) a LCDR3 of SEQ ID NO. 11, an antibody comprising:
  (i) a heavy chain variable domain, or fragment thereof, comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 6,
  (ii) a light chain variable domain, or fragment thereof, comprising (a) a LCDR1 of SEQ ID NO. 24, (b) a LCDR2 of SEQ ID NO. 10 and (c) a LCDR3 of SEQ ID NO. 11, an antibody comprising:
  (i) a heavy chain variable domain, or fragment thereof, comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 21,
  (ii) a light chain variable domain, fragment thereof, comprising (a) a LCDR1 of SEQ ID NO. 25, (b) a LCDR2 of SEQ ID NO. 10 and (c) a LCDR3 of SEQ ID of SEQ ID NO. 27, an antibody comprising:
  (i) a heavy chain variable domain, or fragment thereof, comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 21,
  (ii) a light chain variable domain, or fragment thereof, comprising (a) a LCDR1 of SEQ ID NO. 24, (b) a LCDR2 of SEQ ID NO. 10 and (c) a LCDR3 of SEQ ID NO. 11, and an antibody comprising:
  (i) a heavy chain variable domain, or fragment thereof, comprising (a) a HCDR1 of SEQ ID NO. 1, (b) a HCDR2 of SEQ ID NO. 20, (c) a HCDR3 of SEQ ID NO. 3 and (d) a HFR3 of SEQ ID NO. 22,
  (ii) a light chain variable domain, or fragment thereof, comprising (a) a LCDR1 of SEQ ID NO. 25, (b) a LCDR2 of SEQ ID NO. 10 and (c) a LCDR3 SEQ ID NO. 27, an antibody comprising:
  (i) a heavy chain variable domain, or fragment thereof, comprising (a) a HCDR1 of SEQ ID NO. 1, (b) a HCDR2 of SEQ ID NO. 20, (c) a HCDR3 of SEQ ID NO. 3 and (d) a HFR3 of SEQ ID NO. 22,
  (ii) a light chain variable domain, or fragment thereof, comprising (a) a LCDR1 of SEQ ID NO. 24, (b) a LCDR2 of SEQ ID NO. 10 and (c) a LCDR3 of SEQ ID NO. 11, an antibody comprising:
  (i) a heavy chain variable domain, fragment thereof, comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 22,
  (ii) a light chain variable domain, fragment thereof, comprising (a) a LCDR1 of SEQ ID NO. 24, (b) a LCDR2 of SEQ ID NO. 10 and (c) a LCDR3 of SEQ ID NO. 11, or antigen-binding fragment of the selected antibody.

In some further preferred embodiments, an antibody according to the present disclosure can be selected from:
  an antibody comprising (i) a heavy chain variable domain having 90% or more amino acid identity with SEQ ID NO. 8 and comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 6 and a light chain variable domain having 90% or more amino acid identity with SEQ ID NO. 16 and comprising (a) a LCDR1 of SEQ ID NO. 9, (b) a LCDR2 of SEQ ID NO. 10 and (c) a LCDR3 of SEQ ID NO. 11,
  an antibody comprising (i) a heavy chain variable domain having 90% or more amino acid identity with SEQ ID NO. 29 and comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 6, and (ii) a light chain variable domain having 90% or more amino acid identity with SEQ ID NO. 30 and comprising (a) a LCDR1 of SEQ ID NO. 23, (b) a LCDR2 of SEQ ID NO. 10 and (c) a LCDR3 of SEQ ID NO. 11,
  an antibody comprising (i) a heavy chain variable domain having 90% or more amino acid identity with SEQ ID NO. 31 and comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 6 and (ii) a light chain variable domain having 90% amino acid identity with SEQ ID NO. 32 and comprising (a) a LCDR1 of SEQ ID NO. 24, (b) a LCDR2 of SEQ ID NO. 10 and (c) a LCDR3 of SEQ ID NO. 11, an antibody comprising (i) a heavy chain variable domain having 90% or more amino acid identity with SEQ ID NO. 33 and comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 6, and (ii) a light chain variable domain having 90% or more amino acid identity with SEQ ID NO. 34 and comprising (a) a LCDR1 of SEQ ID NO. 24, (b) a LCDR2 of SEQ ID NO. 10 and (c) a LCDR3 of SEQ ID NO. 11, an antibody comprising (i) a heavy chain variable domain having 90% or more amino acid identity with SEQ ID NO. 35 and comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 6, and (ii) a light chain variable domain having 90% or more amino acid identity with SEQ ID NO. 36 and comprising (a) a LCDR1 of SEQ ID NO. 24, (b) a LCDR2 of SEQ ID NO. 10 and (c) a LCDR3 of SEQ ID NO. 11, an antibody comprising (i) a heavy chain variable domain having 90% or more amino acid identity with SEQ ID NO. 37 and comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 6, and (ii) a light chain variable domain having 90% or more amino acid identity with SEQ ID NO. 38 and comprising (a) a LCDR1 of SEQ ID NO. 24, (b) a LCDR2 of SEQ ID NO. 10 and (c) a LCDR3 of SEQ ID NO. 11, an antibody comprising (i) a heavy chain variable domain having 90% or more amino acid identity with SEQ ID NO 39 and comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 21, and (ii) a light chain variable domain of SEQ ID NO. 40 and comprising (a) a LCDR1 of SEQ ID NO. 25, (b) a LCDR2 of SEQ ID NO. 10 and (c) a LCDR3 of SEQ ID NO. 27, an antibody comprising (i) a heavy chain variable domain having 90% or more amino acid identity with SEQ ID NO 41 and comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 21, and (ii) a light chain variable domain having 90% or more amino acid identity with SEQ ID NO. 42 and comprising (a) a LCDR1 of SEQ ID NO. 24, (b) a LCDR2 of SEQ ID NO. 10 and (c) a LCDR3 of SEQ ID NO. 11, an antibody comprising (i) a heavy chain variable domain having 90% or more amino acid identity with SEQ ID NO 43 and comprising (a) a HCDR1 of SEQ ID NO. 1, (b) a HCDR2 of SEQ ID NO. 20, (c) a HCDR3 of SEQ ID NO. 3 and (d) a HFR3 of SEQ ID NO. 22, and (ii) a light chain variable domain having 90% or more amino acid identity with SEQ ID NO. 44 and comprising (a) a LCDR1 of SEQ ID NO. 25, (b) a LCDR2 of SEQ ID NO. 10 and (c) a LCDR3 of SEQ ID NO. 27, an antibody comprising (i) a heavy chain variable domain having 90% or more amino acid identity with SEQ ID NO 45 and comprising (a) a HCDR1 of SEQ ID NO. 1, (b) a HCDR2 of SEQ ID NO. 20, (c) a HCDR3 of SEQ ID NO. 3 and (d) a HFR3 of SEQ ID NO. 22, and (ii) a light chain variable domain having 90% or more amino acid identity with SEQ ID NO. 46 and comprising (a) a LCDR1 of SEQ ID NO. 24, (b) a LCDR2 of SEQ ID NO. 10 and (c) a LCDR3 of SEQ ID NO. 11, and an antibody comprising (i) a heavy chain variable domain having 90% or more amino acid identity with SEQ ID NO 47 and comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 22, and (ii) a light chain variable domain having 90% or more amino acid identity with SEQ ID NO. 48 and comprising (a) a LCDR1 of SEQ ID NO. 24, (b) a LCDR2 of SEQ ID NO. 10 and (c) a LCDR3 of SEQ ID NO. 11.

As used herein, an amino acid sequence having 90% or more amino acid identity with a reference sequence has at least 90%, at least 91%, at least 92%, at least 93%, at least 94%, at least 95%, at least 96%, at least 97%, at least 98% or at least 99% amino acid identity with the said reference amino acid sequence.

The above disclosed antibodies encompass the antibodies termed A1, A2, A3, A4, A5, A6, B1, B2, C1, C2 and C3 which are more precisely described elsewhere herein and which have been experimentally assayed in the examples.

Test antibodies may first be screened for their binding affinity to SARS-CoV-2 Spike (S trimer or tri-S), S1 sub-unit and S-RBD in a direct ELISA binding assay. ELISA plates are coated with 250 ng/well of purified recombinant SARS-CoV-2 tri-S(SEQ ID NO: 75), S1 (SEQ ID NO: 76), and S-RBD (SEQ ID NO: 77) and incubated with recombinant monoclonal IgG1 antibodies at 4 or 10 µg/ml, and 4 to 7 consecutive 1:4 dilutions in PBS, Antibody incubation step is for 2 h. Coating, washings, revelation and buffers are as disclosed above. An OD value >0.5 in ELISA binding assay to SARS-CoV-2 Spike (S trimer or tri-S), S1 sub-unit and S-RBD (SEQ ID NO: 64 to 66) according to the present disclosure indicates the presence of binding affinity.

Alternatively, the ability of the antibodies according to the present disclosure to bind to the RBD of SARS-CoV-2 variants including in particular Wuhan (SEQ ID NO. 78), Delta (SEQ ID NO. 79), BA.2 (SEQ ID NO. 80), BA.2.75.2 (SEQ ID NO. 81), BA.4/5 (SEQ ID NO. 82), BQ.1.1 (SEQ ID NO. 83), XBB.1.5 (SEQ ID NO. 84), XBB.1.16 (SEQ ID NO. 85), EG.5 (SEQ ID NO. 86), BA.2.86 (SEQ ID NO. 87) and JN-1 (SEQ ID NO. 88) and block RBD binding to ACE2-ectodomain is assayed in the direct and competition ELISA binding assay according to the present disclosure, using the specified S-RBD protein of SARS-CoV-2 variants.

FIG. 3 shows that, in contrast to the parent antibody SKP002, the antibodies according to the present disclosure, especially antibodies A1, A2, A3, A4, A5, A6, B1, B2, C1, C2 and C3, all bind with a high efficiency to the RBD from all the tested SARS-CoV-2 variants, and particularly to the SARS-CoV-2 variants BA.2.75.2, BQ.1.1, XBB.1.16, EG.5, BA.2.86 and to a lesser extent to JN-1.

Antibodies according to the disclosure inhibit the binding of SARS-CoV-2 Spike (S trimer or tri-S) and/or S-RBD proteins to angiotensin-converting enzyme 2 (ACE2) in a competition ELISA binding assay using a biotinylated SARS-CoV-2 tri-S(SEQ ID NO: 75) or S-RBD (SEQ ID NO: 76) protein and ACE2 ectodomain protein (SEQ ID NO: 77). Plates are coated with purified ACE2 ectodomain protein (250 ng/well) and incubated for 2 h with recombinant monoclonal antibody at 2 µg/ml and consecutive dilutions (1:2) in presence of biotinylated tri-S protein at 1 µg/ml, or recombinant monoclonal IgG1 antibodies at 10 or 100 µg/ml and consecutive dilutions (1:2) in presence of biotinylated RBD at 0.5 µg/ml. Antigen-antibody complexes are detected using streptavidin conjugate, such as streptavidin-HRP and appropriate chromogenic substrate.

Also, FIG. 4 shows that, in contrast to the parent antibody SKP002, the antibodies according to the present disclosure, especially antibodies A1, A2, A3, A4, A5, A6, B1, B2, C1, C2 and C3, all block with a high efficiency the binding of ACE2 to the RBD from all the tested SARS-CoV-2 variants, and particularly to the SARS-CoV-2 variants BA.2.75.2, BQ.1.1, XBB.1.16, EG.5 and BA.2.86. A1, B1 and C1 only block with a high efficiency the binding of ACE2 to the RBD JN.1.

Further, FIG. 5 shows that, in contrast to the parent antibody SKP002, the antibodies according to the present disclosure, especially antibodies A1, A2, A3, A4, A5, B1, B2, C1, C2 and C3 efficiently neutralize cell infection with the SARS-CoV-2 variants XBB.1.5. FIG. 6 also shows that the antibodies A1, B1, and C1 possess a high neutralization potency of the SARS-CoV-2 variants D614G, XBB.1.5, XBB.1.16, EG.5.1, BA.2.86 and JN.1.

Figure 1:
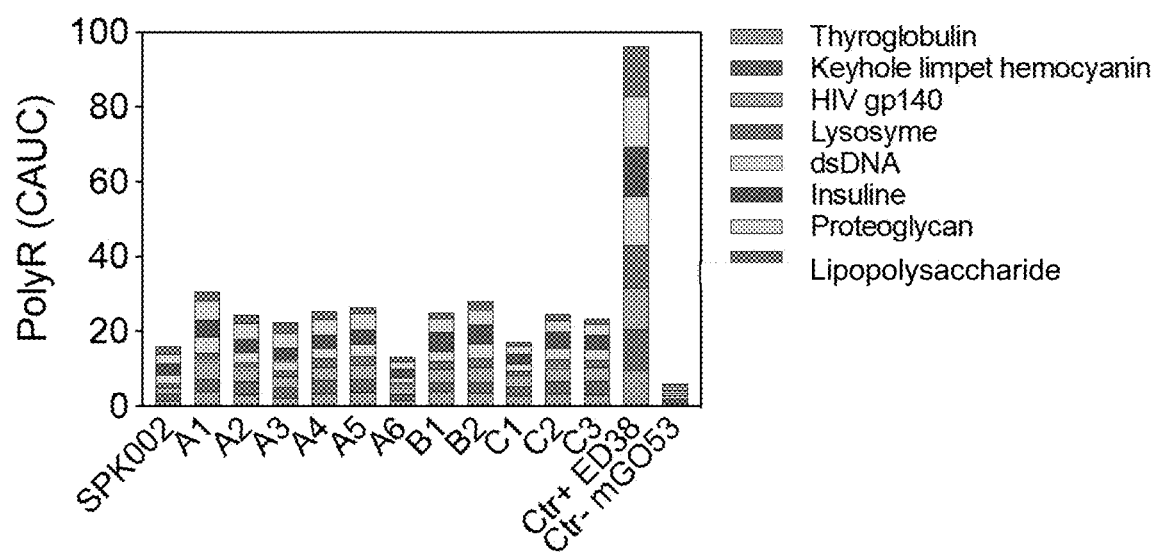
FIG. 1. Polyreactive ELISA binding of a variety of the antibodies described herein. Ordinate: polyreactive ELISA, as expressed as Cumulative Area Under the Curve (CAUC) values. Tested antigens, from the top to the bottom of each bar: (i) Lipopolysaccharide, (ii) Proteoglycan, (iii) Insulin, (iv) dsDNA, (v) Lysozyme, (vi) HIV gp140, (vii) Keyhole limpet hemocyanin and (viii) Thyroglobulin.

The absence of polyreactivity of the antibodies according to the present disclosure is determined in ELISA binding assay. ELISA plates are coated with 500 ng/well of purified double stranded (ds)-DNA, keyhole limpet hemocyanin (KLH), lipopolysaccharide (LPS), Lysozyme, Thyroglobulin, Proteoglycan from *B. subtilis,* 250 ng/well of insulin, and 125 ng/well of YU2 HIV-1 Env gp140 protein in PBS. After blocking and washing steps, recombinant monoclonal IgG antibodies are tested at 4 µg/ml and 7 consecutive 1:4 dilutions in PBS. Control antibodies, mGO53 (negative) (Wardemann H. Predominant Autoantibody Production by Early Human B Cell Precursors. *Science* (80-.). 2003; 301 (5638): 1374-1377), and ED38 (high positive) (Meffre E. et al. Surrogate Light Chain Expressing Human Peripheral B Cells Produce Self-reactive Antibodies. *J. Exp. Med.* 2004; 199 (1): 145-150) are included in each experiment. ELISA binding is developed as described above. OD>0.5 (cut-off value) are considered as positive. Results obtained with antibodies SPK002 (described in WO 2022/228827) and antibodies, A1, A2, A3, A4, A5, A6, B1, B2, C1, C2 and C3 according to the present disclosure are illustrated in FIG. 1.

The absence of self-reactivity of the antibodies according to the present disclosure is determined in indirect immuno-fluorescence assay (IFA) on HEp-2 cells. Recombinant SARS-CoV-2 S-specific and control IgG antibodies (mGO53 and ED38) at 100 µg/ml are tested in indirect immuno-fluorescence assay (IFA) on HEp-2 cells sections (AnA HEp-2 AeskuSlides®, Aesku.Diagnostics, Wendelsheim, Germany) using the kit's controls and FITC-conjugated anti-human IgG antibodies as the tracer according to the manufacturer' instructions. HEp-2 sections are examined using fluorescence microscope and pictures are taken at magnification x 40. Results obtained with antibodies SPK002 (described in WO 2022/228827) and antibodies, A1, A2, A3, A4, A5, A6, B1, B2, C1, C2 and C3 according to the present disclosure are illustrated in FIG. 2.

As used herein, the term "neutralizing antibody" refers to an antibody that inhibits virus infection, in particular that inhibits or blocks virus entry into host cells by competing with SARS-CoV-2 Spike(S) protein for binding to angiotensin-converting enzyme 2 ACE2 receptor on host cells and blocking RBD interaction with ACE2 through binding to the RBD. The neutralizing activity of the antibody is measured by SARS-CoV-2 S-Fuse Assay. SARS-CoV-2 virus (Multiplicity of infection (MOI) of 0.1) is incubated with recombinant monoclonal IgG antibodies at 100 µg/ml, and consecutive 1:2 dilutions in culture medium for 30 min at room temperature and added to S-Fuse cell culture (U2OS-ACE2 GFP1-10 and U2OS-ACE2 GFP 11; ratio 1:1; $8 \times 10^3$ per well). After 18h of incubation, cells are fixed and nuclei stained. The area displaying GFP expression and the number of nuclei are quantified by confocal microscopy. The percentage neutralization is calculated from the GFP-positive area as follows: 100×(1−(value with IgA/IgG-value in "non-infected")/(value in "no IgA/IgG"−value in "non-infected")) (FIG. 5). The neutralizing activity of each isotype is expressed as the half maximal effective concentration ($EC_{50}$). $EC_{50}$ values (ng/ml) are calculated based on a reconstructed curve of the percentage neutralization at the various concentrations indicated. A neutralizing antibody has an $EC_{50}$ of less than 10000 ng/ml and/or neutralizes at least 90% of SARS-CoV-2 in SARS-CoV-2 S-Fuse Assay.

As used herein "preventing" SARS-CoV-2 infection and/or associated disease means reducing the risk of SARS-CoV-2 infection and/or associated disease.

The antibody according to the present disclosure can be selected from:

an antibody comprising (i) a heavy chain variable domain of SEQ ID NO. 8 and (ii) a light chain variable domain of SEQ ID NO. 16, the said antibody being also termed "A1" in the present disclosure, an antibody comprising (i) a heavy chain variable domain of SEQ ID NO. 29 and (ii) a light chain variable domain of SEQ ID NO. 30, the said antibody being also termed "A2" in the present disclosure, an antibody comprising (i) a heavy chain variable domain of SEQ ID NO. 31 and (ii) a light chain variable domain of SEQ ID NO. 32, the said antibody being also termed "A3" in the present disclosure, an antibody comprising (i) a heavy chain variable domain of SEQ ID NO. 33 and (ii) a light chain variable domain of SEQ ID NO. 34, the said antibody being also termed "A4" in the present disclosure, an antibody comprising (i) a heavy chain variable domain of SEQ ID NO. 35 and (ii) a light chain variable domain of SEQ ID NO. 36, the said antibody being also termed "A5" in the present disclosure, an antibody comprising (i) a heavy chain variable domain of SEQ ID NO. 37 and (ii) a light chain variable domain of SEQ ID NO. 38, the said antibody being also termed "A6" in the present disclosure, an antibody comprising (i) a heavy chain variable domain of SEQ ID NO. 39 and (ii) a light chain variable domain of SEQ ID NO. 40, the said antibody being also termed "B1" in the present disclosure, an antibody comprising (i) a heavy chain variable domain of SEQ ID NO. 41 and (ii) a light chain variable domain of SEQ ID NO. 42, the said antibody being also termed "B2" in the present disclosure, an antibody comprising (i) a heavy chain variable domain of SEQ ID NO. 43 and (ii) a light chain variable domain of SEQ ID NO. 44, the said antibody being also termed "C1" in the present disclosure, an antibody comprising (i) a heavy chain variable domain of SEQ ID NO. 45 and (ii) a light chain variable domain of SEQ ID NO. 46, the said antibody being also termed "C2" in the present disclosure, an antibody comprising (i) a heavy chain variable domain of SEQ ID NO. 47 and (ii) a light chain variable domain of SEQ ID NO. 48, the said antibody being also termed "C3" in the present disclosure, or antigen-binding fragment of the selected antibody.

In some particular embodiments, the antibody binds to at least one recombinant SARS-CoV-2 S protein selected from a S-trimer, a S1 sub-unit, and a S-RBD domain with a KD of from 600 nM to 100 pM or less in the Biacore assay according to the present disclosure (see definitions). In some preferred embodiments, S-RBD protein comprises or consists of any one of the RBD of SARS-CoV-2 variants including in particular Wuhan (SEQ ID NO. 78), Delta (SEQ ID NO. 79), BA.2 (SEQ ID NO. 80), BA.2.75.2 (SEQ ID NO. 81), BA.4/5 (SEQ ID NO. 82), BQ.1.1 (SEQ ID NO. 83), XBB.1.5 (SEQ ID NO. 84), XBB.1.16 (SEQ ID NO. 85), EG.5 (SEQ ID NO. 86), BA.2.86 (SEQ ID NO. 87) and JN-1 (SEQ ID NO. 88).

In some particular embodiments, the antibody binds to at least one recombinant SARS-CoV-2 S protein selected from a S-trimer, a S1 subunit and a S-RBD, with a binding affinity which is higher than that of ACE2 ectodomain protein; preferably at least 5, 10, 25, 50, 100, 250, 500 or 1000 folds higher (which means that the KD of the antibody for S-trimer, S1 subunit, and/or S-RBD is at least 5, 10, 25, 50, 100, 250, 500 or 1000 folds lower than that of ACE2 ectodomain protein); preferably wherein the binding affinity of the antibody for the recombinant S-RBD protein is at least 10, 25, 50, 100, 250, 500 or 1000 folds higher compared to that of the recombinant ACE2 ectodomain protein; more preferably wherein the binding affinity of the recombinant S-trimer, S1 subunit and S-RBD proteins is at least 10, 25, 50, 100, 250, 500 or 1000 folds higher compared to that of the recombinant ACE2 ectodomain protein. Preferably, wherein the S-trimer protein comprises SEQ ID NO: 75, the S1 subunit protein comprises SEQ ID NO: 65 and/or the recombinant ACE2 ectodomain protein comprises SEQ ID NO: 89.

In some particular embodiments, the antibody has no polyreactivity in the ELISA binding assay according to the present disclosure, as compared to a control antibody (see definitions). In some particular embodiments, the antibody has no self-reactivity in the indirect immuno-fluorescence assay (IFA) on HEp-2 cells according to the present disclosure, as compared to a control antibody (see definitions). In some particular embodiments, the antibody has no predicted reactivity to human proteins in the Protein microarray binding assay according to the present disclosure (see definitions).

Full length heavy and light chains of antibodies A1, A2, A3, A4, A5, A6, B1, B2, C1, C2 and C3 according to the present disclosure are disclosed, respectively: (i) for A1 in SEQ ID NO. 51 and 52, (ii) for A2 in SEQ ID NO. 53 and 54, (iii) for A3 in SEQ ID NO. 55 and 56, (iv) for A4 in SEQ ID NO. 57 and 58, (v) for A5, in SEQ ID NO. 59 and 60, (vi) for A6 in SEQ ID NO. 61 and 62, (vii) for B1 in SEQ ID NO. 63 and 64, (viii) for B2 in SEQ ID NO. 65 and 66, (ix) for C1 in SEQ ID NO. 67 and 68, (x) for C2 in SEQ ID NO. 69 and 70 and (xi) for C3 in SEQ ID NO. 71 and 72.

Thus, in some particular embodiments, the antibody or antigen-binding fragment thereof according to the present disclosure comprises a heavy chain amino acid sequence selected from the group consisting of: SEQ ID NO: 51, 53, 55, 57, 59, 61, 63, 65, 67, 69 and 71.

Also, in some particular embodiments, the antibody or antigen-binding fragment thereof according to the present disclosure comprises a light chain amino acid sequence selected from the group consisting of: SEQ ID NO: 52, 54, 56, 58, 60, 62, 64, 66, 68, 70 and 72.

In some more particular embodiments, an antibody according to the present disclosure, or antigen-binding fragment thereof, comprises:

a) a heavy chain of SEQ ID NO. 51 and a light chain of SEQ ID NO. 52s, which antibody may be termed "A1" herein, b) a heavy chain of SEQ ID NO. 53 and a light chain of SEQ ID NO. 54, which antibody may be termed "A2" herein, c) a heavy chain of SEQ ID NO. 55 and a light chain of SEQ ID NO. 56, which antibody may be termed "A3" herein, d) a heavy chain of SEQ ID NO. 57 and a light chain of SEQ ID NO. 58, which antibody may be termed "A4" herein, e) a) a heavy chain of SEQ ID NO. 59 and a light chain of SEQ ID NO. 60, which antibody may be termed "A5" herein, f) a) a heavy chain of SEQ ID NO. 61 and a light chain of SEQ ID NO. 62, which antibody may be termed "A6" herein, g) a heavy chain of SEQ ID NO. 63 and a light chain of SEQ ID NO. 64, which antibody may be termed "B1" herein, h) a heavy chain of SEQ ID NO. 65 and a light chain of SEQ ID NO. 66, which antibody may be termed "B2" herein, i) a heavy chain of SEQ ID NO. 67 and a light chain of SEQ ID NO. 68, which antibody may be termed "C1" herein, j) a heavy chain of SEQ ID NO. 69 and a light chain of SEQ ID NO. 70, which antibody may be termed "C2" herein, and k) a heavy chain of SEQ ID NO. 71 and a light chain of SEQ ID NO. 72, which antibody may be termed "C3" herein.

In main embodiments, the said antibody, or antigen-binding fragment thereof, comprises only natural amino acids.

In some embodiments of the said antibody, or antigen-binding fragment thereof, comprises one or more non natural amino acids.

It is further contemplated that antibodies or antigen-binding fragment thereof may be further screened or optimized for their neutralizing properties as above defined. In particular, it is contemplated that monoclonal antibodies or antigen-binding fragment thereof may have 1, 2, 3, 4, 5, 6, or more alterations in the amino acid sequence of 1, 2, 3, 4, 5, or 6 CDRs of monoclonal antibodies provided herein. It is contemplated that the amino acid in position 1, 2, 3, 4, 5, 6, 7, 8, 9, or 10 of CDR1, CDR2, CDR3, CDR4, CDR5, or CDR6 of the VJ or VDJ region of the light or heavy variable region of antibodies may have an insertion, deletion, or substitution with a conserved or non-conserved amino acid. Such amino acids that can either be substituted or constitute the substitution are disclosed below. In some particular embodiments, the monoclonal antibodies or antigen-binding fragment have 1 or 2 conservative substitutions in the amino acid sequence of 1, 2, 3, 4, 5, or 6 CDRs of monoclonal antibodies provided herein.

In some embodiments, the amino acid differences are conservative substitutions, i.e., substitutions of one amino acid with another having similar chemical or physical properties (size, charge or polarity), which substitution generally does not adversely affect the biochemical, biophysical and/or biological properties of the antibody. In particular, the substitution does not disrupt the interaction of the antibody with the spike glycoprotein antigen and neutralizing properties. Said conservative substitution(s) are advantageously chosen within one of the following five groups: Group 1-small aliphatic, non-polar or slightly polar residues (A, S, T, P, G); Group 2-polar, negatively charged residues and their amides (D, N, E, Q); Group 3-polar, positively charged residues (H, R, K); Group 4-large aliphatic, nonpolar residues (M, L, I, V, C); and Group 5-large, aromatic residues (F, Y, W).

In particular, it is contemplated that monoclonal antibodies or antigen-binding fragment thereof may have 1, 2, 3, 4, 5, 6, 7, 8, 9, 10 or more alterations in the amino acid sequence of 1, 2, 3, 4, 5, 6, 7, 8 FRs of monoclonal antibodies provided herein. It is contemplated that the FR sequences have an insertion, deletion, or substitution with a conserved or non-conserved amino acid. Such amino acids that can either be substituted or constitute the substitution are disclosed above. In some particular embodiments, the monoclonal antibodies or antigen-binding fragment have 1, 2, 3, 4, 5; preferably 1 or 2 conservative substitutions in the amino acid sequence of 1, 2, 3, 4, 5, 6, 7, 8 FRs of monoclonal antibodies provided herein.

In a more particular embodiment, an antibody according to the present disclosure can be selected from:
a) an antibody, which may be termed "A1" herein, comprising:
  a1) a heavy chain variable domain comprising (i) a FR1 of SEQ ID NO. 4, (ii) a CDR1 of SEQ ID NO. 1, (iii) a FR2 of SEQ ID NO. 5, (iv) a CDR2 of SEQ ID NO. 2, (v) a FR3 of SEQ ID NO. 6, (vi) a CDR3 of SEQ ID NO. 3 and (vii) a FR4 of SEQ ID NO. 7, and
  a2) a light chain variable domain comprising (i) a FR1 of SEQ ID NO. 12, (ii) a CDR1 of SEQ ID NO. 9, (iii) a FR2 of SEQ ID NO. 13, (iv) a CDR2 of SEQ ID NO. 10, (v) a FR3 of SEQ ID NO. 14, (vi) a CDR3 of SEQ ID NO. 11 and (vii) a FR4 of SEQ ID NO. 15,
b) an antibody, which may be termed "A2" herein, comprising:
  b1) a heavy chain variable domain comprising (i) a FR1 of SEQ ID NO. 4, (ii) a CDR1 of SEQ ID NO. 1, (iii) a FR2 of SEQ ID NO. 5, (iv) a CDR2 of SEQ ID NO. 2, (v) a FR3 of SEQ ID NO. 6, (vi) a CDR3 of SEQ ID NO. 3 and (vii) a FR4 of SEQ ID NO. 7, and
  b2) a light chain variable domain comprising (i) a FR1 of SEQ ID NO. 12, (ii) a CDR1 of SEQ ID NO. 23, (iii) a FR2 of SEQ ID NO. 13, (iv) a CDR2 of SEQ ID NO. 10, (v) a FR3 of SEQ ID NO. 14, (vi) a CDR3 of SEQ ID NO. 11 and (vii) a FR4 of SEQ ID NO. 15,
c) an antibody, which may be termed "A3" herein, comprising:
  c1) a heavy chain variable domain comprising (i) a FR1 of SEQ ID NO. 4, (ii) a CDR1 of SEQ ID NO. 1, (iii) a FR2 of SEQ ID NO. 5, (iv) a CDR2 of SEQ ID NO. 2, (v) a FR3 of SEQ ID NO. 6, (vi) a CDR3 of SEQ ID NO. 3 and (vii) a FR4 of SEQ ID NO. 7, and c2) a light chain variable domain comprising (i) a FR1 of SEQ ID NO. 12, (ii) a CDR1 of SEQ ID NO. 24, (iii) a FR2 of SEQ ID NO. 13, (iv) a CDR2 of SEQ ID NO. 10, (v) a FR3 of SEQ ID NO. 14, (vi) a CDR3 of SEQ ID NO. 11 and (vii) a FR4 of SEQ ID NO. 15,
d) an antibody, which may be termed "A4" herein, comprising:
  d1) a heavy chain variable domain comprising (i) a FR1 of SEQ ID NO. 17, (ii) a CDR1 of SEQ ID NO. 1, (iii) a FR2 of SEQ ID NO. 5, (iv) a CDR2 of SEQ ID NO. 2, (v) a FR3 of SEQ ID NO. 6, (vi) a CDR3 of SEQ ID NO. 3 and (vii) a FR4 of SEQ ID NO. 7, and
  d2) a light chain variable domain comprising (i) a FR1 of SEQ ID NO. 12, (ii) a CDR1 of SEQ ID NO. 24, (iii) a FR2 of SEQ ID NO. 13, (iv) a CDR2 of SEQ ID NO. 10, (v) a FR3 of SEQ ID NO. 14, (vi) a CDR3 of SEQ ID NO. 11 and (vii) a FR4 of SEQ ID NO. 15,
e) an antibody, which may be termed "A5" herein, comprising:
  e1) a heavy chain variable domain comprising (i) a FR1 of SEQ ID NO. 17, (ii) a CDR1 of SEQ ID NO. 1, (iii) a FR2 of SEQ ID NO. 5, (iv) a CDR2 of SEQ ID NO. 2, (v) a FR3 of SEQ ID NO. 6, (vi) a CDR3 of SEQ ID NO. 3 and (vii) a FR4 of SEQ ID NO. 7, and
  e2) a light chain variable domain comprising (i) a FR1 of SEQ ID NO. 12, (ii) a CDR1 of SEQ ID NO. 24, (iii) a FR2 of SEQ ID NO. 13, (iv) a CDR2 of SEQ ID NO. 10, (v) a FR3 of SEQ ID NO. 26, (vi) a CDR3 of SEQ ID NO. 11 and (vii) a FR4 of SEQ ID NO. 15,
f) an antibody, which may be termed "A6" herein, comprising:
  f1) a heavy chain variable domain comprising (i) a FR1 of SEQ ID NO. 18, (ii) a CDR1 of SEQ ID NO. 1, (iii) a FR2 of SEQ ID NO. 5, (iv) a CDR2 of SEQ ID NO. 2, (v) a FR3 of SEQ ID NO. 6, (vi) a CDR3 of SEQ ID NO. 3 and (vii) a FR4 of SEQ ID NO. 7, and
  f2) a light chain variable domain comprising (i) a FR1 of SEQ ID NO. 12, (ii) a CDR1 of SEQ ID NO. 24, (iii) a FR2 of SEQ ID NO. 13, (iv) a CDR2 of SEQ ID NO. 10, (v) a FR3 of SEQ ID NO. 26, (vi) a CDR3 of SEQ ID NO. 11 and (vii) a FR4 of SEQ ID NO. 15,
g) an antibody, which may be termed "B1" herein, comprising:
  g1) a heavy chain variable domain comprising (i) a FR1 of SEQ ID NO. 19, (ii) a CDR1 of SEQ ID NO. 1, (iii) a FR2 of SEQ ID NO. 5, (iv) a CDR2 of SEQ ID NO. 2, (v) a FR3 of SEQ ID NO. 21, (vi) a CDR3 of SEQ ID NO. 3 and (vii) a FR4 of SEQ ID NO. 7, and
  g2) a light chain variable domain comprising (i) a FR1 of SEQ ID NO. 12, (ii) a CDR1 of SEQ ID NO. 25, (iii) a FR2 of SEQ ID NO. 13, (iv) a CDR2 of SEQ ID NO. 10, (v) a FR3 of SEQ ID NO. 26, (vi) a CDR3 of SEQ ID NO. 27 and (vii) a FR4 of SEQ ID NO. 15,
h) an antibody, which may be termed "B2" herein, comprising:
  h1) a heavy chain variable domain comprising (i) a FR1 of SEQ ID NO. 19, (ii) a CDR1 of SEQ ID NO. 1, (iii) a FR2 of SEQ ID NO. 5, (iv) a CDR2 of SEQ ID NO. 2, (v) a FR3 of SEQ ID NO. 21, (vi) a CDR3 of SEQ ID NO. 3 and (vii) a FR4 of SEQ ID NO. 7, and
  h2) a light chain variable domain comprising (i) a FR1 of SEQ ID NO. 12, (ii) a CDR1 of SEQ ID NO. 24, (iii) a FR2 of SEQ ID NO. 13, (iv) a CDR2 of SEQ ID NO. 10, (v) a FR3 of SEQ ID NO. 26, (vi) a CDR3 of SEQ ID NO. 11 and (vii) a FR4 of SEQ ID NO. 15,
i) an antibody, which may be termed "C1" herein, comprising:
  i1) a heavy chain variable domain comprising (i) a FR1 of SEQ ID NO. 19, (ii) a CDR1 of SEQ ID NO. 1, (iii) a FR2 of SEQ ID NO. 5, (iv) a CDR2 of SEQ ID NO. 20, (v) a FR3 of SEQ ID NO. 22 (vi) a CDR3 of SEQ ID NO. 3 and (vii) a FR4 of SEQ ID NO. 7, and
  i2) a light chain variable domain comprising (i) a FR1 of SEQ ID NO. 12, (ii) a CDR1 of SEQ ID NO. 25, (iii) a FR2 of SEQ ID NO. 13, (iv) a CDR2 of SEQ ID NO. 10, (v) a FR3 of SEQ ID NO. 14, (vi) a CDR3 of SEQ ID NO. 27 and (vii) a FR4 of SEQ ID NO. 15,
j) an antibody, which may be termed "C2" herein, comprising:
  j1) a heavy chain variable domain comprising (i) a FR1 of SEQ ID NO. 19, (ii) a CDR1 of SEQ ID NO. 1, (iii) a FR2 of SEQ ID NO. 5, (iv) a CDR2 of SEQ ID NO. 20, (v) a FR3 of SEQ ID NO. 22, (vi) a CDR3 of SEQ ID NO. 3 and (vii) a FR4 of SEQ ID NO. 7, and j2) a light chain variable domain comprising (i) a FR1 of SEQ ID NO. 12, (ii) a CDR1 of SEQ ID NO. 24, (iii) a FR2 of SEQ ID NO. 13, (iv) a CDR2 of SEQ ID NO. 10, (v) a FR3 of SEQ ID NO. 14, (vi) a CDR3 of SEQ ID NO. 11 and (vii) a FR4 of SEQ ID NO. 15, k) an antibody, which may be termed "C3" herein, comprising:

k1) a heavy chain variable domain comprising (i) a FR1 of SEQ ID NO. 12, (ii) a CDR1 of SEQ ID NO. 1, (iii) a FR2 of SEQ ID NO. 5, (iv) a CDR2 of SEQ ID NO. 2, (v) a FR3 of SEQ ID NO. 22, (vi) a CDR3 of SEQ ID NO. 3 and (vii) a FR4 of SEQ ID NO. 7, and k2) a light chain variable domain comprising (i) a FR1 of SEQ ID NO. 12, (ii) a CDR1 of SEQ ID NO. 24, (iii) a FR2 of SEQ ID NO. 13, (iv) a CDR2 of SEQ ID NO. 10, (v) a FR3 of SEQ ID NO. 14, (vi) a CDR3 of SEQ ID NO. 11 and (vii) a FR4 of SEQ ID NO. 15.

In a particular embodiment of the disclosure, the variable regions of the antibody as described above may be associated with antibody constant regions, like IgA, IgM, IgE, IgD or IgG such as IgG1, IgG2, IgG3, IgG4. Said variable regions of the antibody is preferably associated with IgG or IgA constant region; preferably IgG1 or IgA (IgA1, IgA2) constant regions. These constant regions may be further mutated or modified, by methods known in the art, in particular for modifying their binding capability towards Fc receptor or enhancing antibody half-life. The antibody comprising IgA constant region may further comprise a J chain and/or a secretory component to generate a polymeric or secretory IgA.

In some embodiments, the said antibody comprises a constant heavy chain region. According to some of these embodiments, the constant heavy chain region is of SEQ ID NO. 49.

In some embodiments, the said antibody comprises a constant light chain region. According to some of these embodiments, the constant light chain region is of SEQ ID NO. 50.

As used herein, the term "IgG Fc region" is used to define the C-terminal region of an immunoglobulin heavy chain, including native sequence Fc region and variant Fc regions. The human IgG heavy chain Fc region is generally defined as comprising the amino acid residue from position C226 or from P230 to the carboxyl-terminus of the IgG antibody. The numbering of residues in the Fc region is that of the EU index of Kabat. The C-terminal lysine (residue K447) of the Fc region may be removed, for example, during production or purification of the antibody. Accordingly, a composition of antibodies of the disclosure may comprise antibody populations with all K447 residues removed, antibody populations with no K447 residues removed, and antibody populations having a mixture of antibodies with and without the K447 residue.

In a particular embodiment, the anti-SARS-CoV-2 antibody according to the present disclosure is a silent antibody. As used herein, the term "silent" antibody refers to an antibody that exhibits no or low ADCC activity. Silenced effector functions can be obtained by mutation in the Fc region of the antibodies and have been described in the Art: Strohl 2009 (LALA & N297A); Baudino 2008, D265A (Baudino et al., J. Immunol. 181 (2008): 6664-69, Strohl, CO Biotechnology 20 (2009): 685-91). Examples of silent Fc IgG1 antibodies comprise N297A or L234A and L235A mutations in the IgG1 Fc amino acid sequence.

In another particular embodiment of any of the antibodies or antigen-binding fragments described herein, the variant human Fc constant region comprises the M428L and N434S substitutions (LS) in EU index of Kabat to enhance antibody half-life. In some embodiments, the antibody of the present disclosure does not comprise an Fc domain capable of substantially binding to a FcgRIIIA (CD16) polypeptide. In some embodiments, the antibody of the present disclosure lacks an Fc domain (e.g. lacks a CH2 and/or CH3 domain).

Other mutations are G236A/A330L/I332E, herein termed "GAALIE which improves antiviral efficacy against pathogens (Bournazos et al., Nature, 2020, 588, 485-490). The M428L and N434S substitutions (LS) are advantageously combined with G236A/A330L/I332E.

Another modification of the antibodies herein that is contemplated by the present disclosure is pegylation or hesylation or related technologies. An antibody can be pegylated to, for example, increase the biological (e.g., serum) half-life of the antibody. To pegylate an antibody, the antibody, or fragment thereof, typically is reacting with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the disclosure. See for example, EP 0 154 316 by Nishimura et al. and EP 0 401 384 by Ishikawa et al.

Another modification of the antibodies that is herein contemplated is a conjugate or a fusion protein. The antibody or antigen-binding fragment thereof may be fused to another protein moiety of interest or conjugated to an agent of interest. The agent may be for example a therapeutic agent; a label for antibody detection or a protein which increases the half-life of the antibody. In some embodiments, at least the antigen-binding region of the antibody of the present disclosure is fused to a serum protein, such as human serum albumin or a fragment thereof to increase half-life of the resulting molecule. In other embodiments, the antibody or antigen binding fragment according to the present disclosure further comprises a detectable label. Preferred labels include fluorophores such as umbelliferone. fluorescein, fluorescein isothiocyanate (FITC), rhodamine, tetramethyl rhodamine. eosin, green fluorescent protein, erythrosin. coumarin, methyl coumarin, pyrene, malachite green, stilbene, lucifer yellow, Cascade Blue, Texas Red, dichlorotriazinylamine fluorescein, dansyl chloride, phycoerythrin, fluorescent lanthanide complexes such as those including Europium and Terbium, cyanine dye family members, such as Cy3 and Cy5, molecular beacons and fluorescent derivatives thereof, a chromophore label; a luminescent label such as luminol; a radioactive label such as $^{14}$C, $^{123}$I, $^{124}$I, $^{125}$I, $^{32}$P, $^{33}$P, $^{35}$S, or $^{3}$H and others; an affinity-ligand label, such as streptavidin/biotin, avidin/biotin or anti-isotype antibody; an enzyme label, such as alkaline phosphatase, horseradish peroxidase, luciferase, β galactosidase or acetylcholinesterase; an enzyme cofactor label; a hapten conjugate label, such as digoxigenin or dinitrophenyl; a Raman signal generating label; a magnetic label: a spin label; an epitope label, such as the FLAG or HA epitope; a heavy atom label; a nanoparticle label, an electrochemical label; a light scattering or plasmon resonant materials such as gold or silver particles or quantum dots; a spherical shell label; semiconductor nanocrystal label: as well as others known in the art, wherein the label can allow visualization with or without a secondary detection molecule.

In some embodiments, in an antibody according to the present disclosure, or antigen-binding fragment thereof, the constant region comprises mutation(s) and/or modification(s) that silence antibody effector functions and/or increase half-life in vivo.

In some embodiments, said antibody is polymeric. The polymeric antibody comprises or consists of Ig polymers. The polymeric antibody is preferably a polymeric monoclonal antibody derived from a monoclonal antibody as defined above. The Ig polymers comprise or consist of dimers. The polymeric antibody usually comprises immunoglobulin joining (J) chain(s) in addition to Ig molecules. The J chain is a 137 amino acid polypeptide expressed by plasma or myeloma cells which regulate Ig polymer formation by binding covalently to two Ig molecules through disulfide bonds between cysteine residues. In particular, dimeric antibodies are formed by two monomeric Ig molecules, which covalently bind to a J chain. In a preferred embodiment, said antibody is a polymeric IgA, preferably a polymeric IgA monoclonal antibody derived from a monoclonal antibody as defined above.

In some embodiments the antibody is a secretory antibody, preferably a secretory IgA. A secretory antibody can be transported across epithelial cells to the luminal surface of serosal tissues. The secretory antibody is usually a polymeric antibody, preferably a polymeric IgA, comprising a complex of J-chain-containing polymer of Ig and secretory component (SC). The secretory component is a proteolytic cleavage product of the extracellular part of the polymeric immunoglobulin receptor (pIgR) which binds to J-chain containing polymeric Ig. The secretory antibody is preferably a secretory IgA monoclonal antibody derived from a monoclonal antibody as defined above.

In some preferred embodiment, the neutralizing antibody is a recombinant human monoclonal antibody, preferably of IgG1 or IgA isotype. The IgA may be monomeric, polymeric or secretory IgA; it is preferably a polymeric or secretory IgA. In some more preferred embodiments, the recombinant antibody is a silent antibody that may further comprise mutations and/or or modifications to enhance antibody half-life, as described above.

The present invention also relates to an antigen binding fragment of an antibody that contain the variable domains comprising the CDRs domains as described above such as Fv, dsFv, scFv, Fab, Fab', F(ab')$_2$. In particular, said antigen binding fragment is a F(ab')$_2$ fragment. The F(ab')$_2$ fragment can be produced by pepsin digestion of an antibody below the hinge disulfide; it comprises two Fab' fragments, and additionally a portion of the hinge region of the immunoglobulin molecule. Fab fragments are monomeric fragments obtainable by papain digestion of an antibody; they comprise the entire L chain, and a VH-CH1 fragment of the H chain, bound together through a disulfide bond. The Fab' fragments are obtainable from F(ab')$_2$ fragments by cutting a disulfide bond in the hinge region. F(ab')$_2$ fragments are divalent, i.e. they comprise two antigen binding sites, like the native immunoglobulin molecule; on the other hand, Fv (a VHVL dimer constituting the variable part of Fab), dsFv, scFv, Fab, and Fab' fragments are monovalent, i.e. they comprise a single antigen-binding site. These basic antigen-binding fragments of the disclosure can be combined together to obtain multivalent antigen-binding fragments, such as diabodies, tribodies or tetrabodies. These multivalent antigen-binding fragments are also part of the present invention. Fv fragments consist of the VL and VH domains of an antibody associated together by hydrophobic interactions; in dsFv fragments, the VH: VL heterodimer is stabilized by a disulphide bond; in scFv fragments, the VL and VH domains are connected to one another via a flexible peptide linker thus forming a single-chain protein.

In some particular embodiments, the antibody is a whole antibody or an antigen-binding fragment.

The present disclosure further relates to an immunoconjugate comprising an antibody as disclosed herein, or antigen-binding fragment thereof.

Conjugated antibodies can be harnessed for therapeutic purposes. When conjugated with antiviral agents or toxins, these antibodies can deliver a double blow to the virus. The antibody component specifically targets and binds to the virus, while the conjugated payload exerts a therapeutic effect, either by neutralizing the virus directly or by triggering an immune response. This approach is recognized as consisting of a promising approach in the development of targeted antiviral therapies for SARS-Cov infections.

In some embodiments, the said antibody, or antigen-binding fragment thereof, is comprised in an immunoconjugate, such as an immunoconjugate wherein the said antibody is conjugated with another moiety, such as another moiety selected from another antibody, including another anti-SARS-CoV-2 antibody, a cytotoxic moiety (to form an ADC), a cell-penetrating compound or a tissue-penetrating compound.

In some embodiments, antibody described herein, or antigen-binding fragment thereof, may be conjugated to any therapeutic agent. As used herein, the term "immunoconjugate" is chemically or biologically linked to, notably, cytokine, interferon, targeting or reporter moiety, enzyme, peptide or protein, or therapeutic agent or cytotoxic agent, a cell-penetrating compound or a tissue-penetrating compound.

Cytotoxic agents may be selected from monomethyl auristatin E (MMAE), monomethyl auristatin F (MMAF), maytanisoid DM1 (DM1), maytanisoid DM4 (DM4), calicheamicin, duocarmycin, pyrrolobenzodiazepine (PBD), camptothecine, auristatin E, SN-38 or vinca alcaloids such as vinblastine and vincristine.

Cell-penetrating agents may be selected from TAT peptide, penetratin, arginin-riche peptides, transportan, lipophilic peptides, cell-penetrating peptide (CPP), octa-arginine (R8), cholesterol-based agents and antennapedia-homeodomain-derived peptide (antp).

Tissue-penetrating agents include nanoparticles to which an antibody described herein, or antigen-binding fragment thereof, is conjugated. For penetrating the blood brain barrier, the tissue-penetrating agent may be selected from the TAT peptide, the angiopep-2 peptide or cell penetrating peptides (CPP). For penetrating the blood brain barrier, the antibody described herein, or antigen-binding fragment thereof may be conjugated to another antibody, such as an antibody directed against the transferrin receptor or antibodies directed against beta-amyloid protein.

In some particular embodiments, an antibody according to the present disclosure, or antigen-binding fragment thereof, binds to recombinant SARS-CoV-2 RBD domain of the Spike protein from the (i) Wuhan variant of SEQ ID NO. 78, (ii) Delta variant of SEQ ID NO. 79, (iii) BA.2 variant of SEQ ID NO. 80, (iv) BA.2.75.2 variant of SEQ ID NO. 81, (v) BA 4/5 variant of SEQ ID NO. 82, (vi) BQ.1.1. variant of SEQ ID NO. 83, (vii) XBB.1.5. variant of SEQ ID NO. 84, (viii) XBB.1.16 variant of SEQ ID NO. 85, (ix) EG.5 variant of SEQ ID NO. 86, (x) BA.2.86 variant of SEQ ID NO. 87 and (xi) JN-1 variant of SEQ ID NO. 88.

In some particular embodiments, the antibody according to the present disclosure neutralizes at least one SARS-CoV-2 selected from the isolates D614G, XBB.1.5, XBB.1.16, EG.5.1.

In some particular embodiments, the antibody according to the present disclosure, or antigen-binding fragment thereof, is produced recombinantly and comprises a non-native human glycosylation pattern and/or a non-human glycosylation pattern.

Nucleic Acid, Host Cell, Antibody Production

Also disclosed herein are nucleic acid molecule(s) that encode(s) the anti-SARS-CoV-2 antibody of the present disclosure. Nucleic acids encoding an anti-SARS-CoV-2 antibody of the present disclosure are determinable by the skilled person from the amino acid sequence thereof.

The present disclosure relates to a nucleic acid encoding an antibody or antigen-binding fragment thereof, according to any one of the preceding claims; preferably comprising at least a nucleic acid sequence encoding the heavy and/or light chain of said antibody or antigen-binding fragment thereof.

Typically, said nucleic acid is recombinant, synthetic or semi-synthetic nucleic acid which is expressible in a host cell suitable for antibody expression or production, in particular human antibody production. The host cell may a cell for recombinant antibody production or a patient cell for antibody production in vivo. Typically, the nucleic acid may be DNA, RNA or mixed molecule, which may further be modified and/or included in any suitable expression vector. As used herein, the terms "vector" and "expression vector" mean the vehicle by which a DNA or RNA sequence (e.g. a foreign gene) can be introduced into a host cell, so as to transform the host and promote expression (e.g. transcription and translation) of the introduced sequence. The recombinant vector can be a vector for eukaryotic or prokaryotic expression, such as a plasmid, a phage for bacterium introduction, a YAC able to transform yeast, a viral vector and especially a retroviral vector, or any expression vector. An expression vector as defined herein is chosen to enable the production of an antibody. either in vitro or in vivo.

In some particular embodiments, the nucleic acid is mRNA, preferably modified mRNA.

A further object of the disclosure relates to a vector comprising a nucleic acid as described herein.

This disclosure further pertains to an expression vector for the recombinant production of an antibody as described herein, or antigen-binding fragment thereof, in a host cell, comprising at least one nucleic acid encoding said antibody.

Examples of nucleic acid molecules are those encoding the variable light and heavy chain amino acid sequences of the anti-SARS-CoV-2 antibody as disclosed in the previous section, and using the genetic code and, optionally taking into account the codon bias depending on the host cell species.

The nucleic acid molecule or construct sequence is advantageously codon-optimized for expression in a host cell suitable for antibody production in host cell, in particular mammalian cells. Codon optimization is used to improve protein expression level in living organism by increasing translational efficiency of target gene. Appropriate methods and softwares for codon optimization in the desired host are well-known in the art and publically available (see for example the GeneOptimizer software suite in Raab et al., Systems and Synthetic Biology, 2010, 4, (3), 215-225).

The present disclosure also relates to a host cell comprising an expression vector as described herein or a nucleic acid according as above described.

The host cell for antibody production may be eukaryote or prokaryote cell. Prokaryote cell is in particular bacteria. Eukaryote cell includes yeast, insect cell and mammalian cell.

Preferably, the host cell is an antibody producing cell-line stably transformed with the expression vector.

The present disclosure also pertains to nucleic acid molecules that derive from the latter sequences having been optimized for protein expression in host cells, in particular eukaryotic cells, preferably mammalian cells, for example, CHO or HEK cell lines or human cells.

In some embodiments, said nucleic acid molecule is a eukaryotic, preferably mammalian, expression cassette, wherein the antibody coding sequence(s) is operably linked to appropriate regulatory sequence(s) for their expression in an antibody producing cell or a patient cell. Such sequences which are well-known in the art include in particular a promoter, and further regulatory sequences capable of further controlling the expression of a transgene, such as without limitation, enhancer, terminator and intron. The promoter may be a tissue-specific, ubiquitous, constitutive or inducible promoter that is functional in the antibody producing cell. Such promoters are well-known in the art and their sequences are available in public sequence data bases.

In some particular embodiments, the antibody according to the present disclosure, or antigen-binding fragment thereof, is produced in a eukaryotic recombinant system.

In some other some particular embodiments, the antibody according to the present disclosure, or antigen-binding fragment thereof, is produced in a prokaryotic recombinant system.

In some particular embodiments, the nucleic acid is RNA, preferably mRNA, wherein the coding sequence of the antibody light and/or heavy chain is operably linked to appropriate regulatory sequence(s) for their expression in an individual's target cells or tissue(s). mRNA therapy is well-known in the art. mRNA is delivered into the host cell cytoplasm where expression generates the therapeutic protein of interest. mRNA construct comprises a cap structure, 5' and 3'untranslated regions (UTRs), and open reading frame (ORF), and a 3'poly (A) tail. mRNA construct may be non-replicating mRNA (MRM) or self-amplifying mRNA (SAM). SAM comprises the inclusion of genetic replication machinery derived from positive-strand mRNA viruses, most commonly alphaviruses such as Sindbis and Semliki-Forest viruses. In SAM constructs, the ORF encoding viral structural protein is replaced by the transcript encoding the therapeutic protein of interest, and the viral RNA-dependent RNA polymerase is retained to direct cytoplasmic amplification of the replicon construct. Trans-replicating RNA are disclosed for example in WO 2017/162461. RNA replicon from alphavirus suitable for gene expression are disclosed in WO 2017/162460. mRNA manufacturing process uses plasmid DNA (pDNA) containing a DNA-dependent RNA polymerase promoter, such as T7, and the corresponding sequence for the mRNA construct. The pDNA is linearized to serve as a template for the DNA-dependent RNA polymerase to transcribe the mRNA, and subsequently degraded by a DNase process step. The addition of the 5'cap and the 3'poly (A) tail can be achieved during the in vitro transcription step or enzymatically after transcription. Enzymatic addition of the cap can be accomplished by using guanylyl transferase and 2'-O-methyltransferase to yield a Cap0 ($^{N7Me}$GpppN) or Cap1 ($^{27Me}$GppN$^{2'-oMe}$) structure, respectively, while the poly-A tail can be achieved through enzymatic addition via poly-A polymerase. mRNA is then purified using standard methods suitable for mRNA purification such as high-pressure liquid chromatography (HPLC) and others. Methods for producing mRNA are disclosed for example in WO 2017/182524.

To improve translation efficiency in treated subject cells, the mRNA according to the invention comprises a sequence which is codon-optimized for expression in human. Further improvements of the mRNA construct according to the invention to improve its stability and translation efficiency in vivo include optimization the length and regulatory element sequences of 5'-UTR and 3'UTR; base and/or sugar modifications in the cap structure to increase ribosomal interaction and/or mRNA stability; and modified nucleosides. Modified nucleosides may be in the 5'-UTR, 3'-UTR or ORF. Examples of modified nucleosides include pseudouridine and N-1-methylpseudouridine that remove intracellular signalling triggers for protein kinase R activation. Examples of modified nucleosides that reduce RNA degradation into cells are disclosed in WO 2013/039857. Modified cap structures are disclosed in WO 2011/015347 and WO 2019/175356. Optimized 3'-UTR sequences are disclosed in WO 2017/059902. Modified polyA sequences which improve RNA stability and translation efficiency are disclosed in US 2020/0392518. Modified mRNA with improved stability and translation efficiency are also disclosed in WO 2007/036366.

The invention may use any vector suitable for the delivery and expression of nucleic acid into individual's cells, in particular suitable for nucleic acid therapy. Such vectors that are well-known in the art include viral and non-viral vectors. Non-viral vector includes the various (non-viral) agents which are commonly used to either introduce or maintain nucleic acid into individual's cells. Agents which are used to introduce nucleic acid into individual's cells by various means include in particular polymer-based, particle-based, lipid-based, peptide-based delivery vehicles or combinations thereof, such as with no limitations cationic polymer, dendrimer, micelle, liposome, lipopolyplex, exosome, microparticle and nanoparticle including lipid nanoparticle (LNP) and viral-like particles; and cell penetrating peptides (CPP). Agents which are used to maintain nucleic acid into individual's cells include in particular naked nucleic acid vectors such as plasmids, transposons and mini-circles. Viral vectors are by nature capable of penetrating into cells and delivering nucleic acid(s) of interest into cells, according to a process named as viral transduction. As used herein, the term "viral vector" refers to a non-replicating, non-pathogenic virus engineered for the delivery of genetic material into cells. In viral vectors, viral genes essential for replication and virulence are replaced with an expression cassette for the transgene of interest. Thus, the viral vector genome comprises the transgene expression cassette flanked by the viral sequences required for viral vector production. As used herein, the term "recombinant virus" refers to a virus, in particular a viral vector, produced by standard recombinant DNA technology techniques that are known in the art. As used herein, the term "virus particle" or "viral particle" is intended to mean the extracellular form of a non-pathogenic virus, in particular a viral vector, composed of genetic material made from either DNA or RNA surrounded by a protein coat, called the capsid, and in some cases an envelope derived from portions of host cell membranes and including viral glycoproteins. As used herein, a viral vector refers to a viral vector particle. These vectors have minimal eukaryotic sequences to minimize the possibility of chromosomal integration. In addition, these approaches can advantageously be combined to introduce and maintain the nucleic acid of the invention into individual's cells.

In some embodiments, a mRNA according to the present invention as disclosed above is combined with a nucleic-acid delivery agent suitable for delivery of mRNA into mammalian host cells that are well-known in the art. The mRNA delivery agent may be a polymeric carrier, polycationic protein or peptide, lipid nanoparticle or other. For example, the mRNA (non-replicating or self-amplifying) may be delivered into cells using polymers, in particular cationic polymers, such as polyethylenimine (PEI), poly-L-Lysin (PEL), polyvinylamine (PVA) or polyallylamine (PAA), wherein the mRNA is preferentially present in the form of monomers, dimers, trimers or oligomers as disclosed in WO 2021/001417. Alternatively, the mRNA may be combined with polyalkyleneimine in the form of polyplex particles, suitable for intramuscular administration as disclosed in WO 2019/137999 or WO 2018/011406. The mRNA may also be combined with a polycation, in particular protamine, as disclosed in WO 2016/000792. One or more mRNA molecules may be formulated within a cationic lipid nanoparticle (LNP); for example the formulation may comprise 20-60% cationic lipid; 5-25% non-cationic lipid, 25-55% sterol and 0.5-15% PEG-modified lipid as disclosed WO 2015/164674. The mRNA may also be formulated in RNA decorated particles such as RNA decorated lipid particles, preferably RNA decorated liposomes as disclosed in WO 2015/043613.

In particular embodiments, the vector is a particle or vesicle, in particular lipid-based micro- or nano-vesicle or particle such as liposome or lipid nanoparticle (LNP). In more particular embodiments, the nucleic acid is RNA, in particular mRNA and the vector is a particle or vesicle, in particular LNP as described above. The LNP: mRNA mass ratio can be around 10:1 to 30:1.

In other embodiments, the nucleic acid is DNA, preferably included in an expression vector such as plasmid or viral vector. The invention also relates to a vector comprising the nucleic acid according to the present disclosure. Preferably, the vector is a recombinant integrating or non-integrating viral vector. Examples of recombinant viral vectors include, but not limited to, vectors derived from retrovirus, adenovirus, adeno-associated virus (AAV), herpes virus, poxvirus, and other virus. Retrovirus includes in particular lentivirus vector such as human immunodeficiency virus, including HIV type 1 (HIV-1) and HIV type 2 (HIV-2) vectors.

The polynucleotide according to the disclosure is prepared by the conventional methods known in the art. For example, it is produced by amplification of a nucleic sequence by PCR or RT-PCR, by screening genomic DNA libraries by hybridization with a homologous probe, or else by total or partial chemical synthesis. The recombinant vectors are constructed and introduced into host cells by the conventional recombinant DNA and genetic engineering techniques, which are known in the art.

A further object of the present disclosure relates to a host cell which has been transfected, infected or transformed by a nucleic acid and/or a vector according to the invention. As used herein, the term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. The transformation may be transient or stable over time. Stable transformation may be by integration of the nucleic acid into the host cell genome. A host cell that receives and expresses introduced DNA or RNA has been "transformed".

Said host cells may be prokaryotic cells such as bacteria or eukaryotic cells such as yeasts, insect cells or mammalian cells. Mammalian cells may be simian, human, dog and rodent cells. Mammalian host cells for expressing the antibodies of the disclosure include in particular Chinese Hamster Ovary (CHO cells) including dhfr-CHO cells (described in Urlaub and Chasin, 1980) used with a DHFR selectable marker (as described in Kaufman and Sharp, 1982), CHOK1 dhfr+ cell lines, NSO myeloma cells, COS cells and SP2 cells, for example GS CHO cell lines together with GS Xceed™ gene expression system (Lonza), HEK-293 cells (ATCC CRL-1573). In a preferred embodiment, said host cells are CHO cells, or HEK-293.

The polynucleotide, vector or cell of the disclosure are useful for the production of the protein of the invention using well-known recombinant DNA techniques. The polynucleotide or vector are also useful for nucleic acid therapy as disclosed below.

Antibodies of the present disclosure can be produced in a host cell transfectoma using, for example, a combination of recombinant DNA techniques and gene transfection methods as is well known in the art (Morrison, 1985). For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. When recombinant expression vectors encoding antibody genes are introduced into host cells, in particular eukaryotic cells such as mammalian cells, the antibodies are produced by culturing the host cells for a period of time sufficient for expression of the antibody in the host cells and, optionally, secretion of the antibody into the culture medium in which the host cells are grown. Antibodies can be recovered and purified for example from the culture medium after their secretion using standard protein purification methods (Shukla et al., 2007).

Thus, another aspect relates to a method of production of the antibody according to the present disclosure, comprising: (i) culturing the host cell of the present disclosure for expression of said antibody by the host cell; and optionally (ii) recovering the antibody; and (iii) purifying said antibody, or antigen-binding fragment thereof.

Pharmaceutical Composition and Therapeutic Use

In another aspect, the present disclosure provides a composition, e.g., a pharmaceutical composition, containing an antibody, antigen-binding fragment, nucleic acid or vector disclosed herein, formulated together with at least one of a pharmaceutically acceptable carrier, an adjuvant, and a preservative. For example, the composition comprises an antibody selected from the group consisting of antibodies A1, A2, A3, A4, A5, A6, B1, B2, C1, C2 and C3, their antigen-binding fragments or nucleic acid or vector encoding said antibody or antigen-binding fragment as disclosed herein.

In some embodiments, the nucleic acid is mRNA, preferably modified mRNA as disclosed herein; the mRNA including modified mRNA is advantageously formulated in a particle or vesicle, in particular LNP, as disclosed herein.

As used herein, the term "pharmaceutically acceptable" means approved by a regulatory agency or recognized pharmacopeia such as European Pharmacopeia, for use in animals and/or humans. The term "excipient" refers to a diluent, adjuvant, carrier, or vehicle with which the therapeutic agent is administered.

Any suitable pharmaceutically acceptable carrier, diluent or excipient can be used in the preparation of a pharmaceutical composition (See e.g., Remington: The Science and Practice of Pharmacy, Alfonso R. Gennaro (Editor) Mack Publishing Company, April 1997). Pharmaceutical compositions are typically sterile and stable under the conditions of manufacture and storage. Pharmaceutical compositions may be formulated as solutions (e.g. saline, dextrose solution, or buffered solution, or other pharmaceutically acceptable sterile fluids), microemulsions, liposomes, or other ordered structure suitable to accommodate a high product concentration (e.g. microparticles or nanoparticles). The carrier may be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition.

In some embodiments, the pharmaceutical composition is for systemic, local or systemic combined with local administration. Parenteral pharmaceutical composition includes a composition suitable for intravenous, intraarterial, subcutaneous, intraperitoneal or intramuscular administration. Local administration is preferably respiratory such as by nasal administration, inhalation, insufflation. or bronchoalveolar lavage. The administration may be parenteral injection or infusion, local delivery, or inhalation or sustained delivery. Preferably, the administration is by injection, inhalation, or injection combined with inhalation. Preferably the injection is intravenous, subcutaneous or intramuscular. The inhalation is advantageously done by nebulisation.

In some embodiments the pharmaceutical composition comprises a preservative. Non-limiting examples of preservatives are anti-oxidation agents and anti-bacterial agents. In some embodiments the preservative is present at a known concentration. The presence of a preservative in the composition distinguishes the composition from any composition that occurs in nature. It also imbues the composition with unique functions that are not present in any naturally occurring composition, such as in certain embodiments the ability to be used therapeutically under certain conditions in which the preservative is useful.

In some embodiments the pharmaceutical composition comprises a defined concentration of a recombinant human antibody of this invention. Such compositions do not occur naturally and have a different structure than any naturally occurring composition. The known concentration of the recombinant antibody imbues the compositions with unique functions that are not present in any naturally occurring composition, such as in certain embodiments the ability to be used therapeutically under certain conditions in which the defined concentration of the recombinant antibody is useful.

Generally, a pharmaceutical composition according to the present disclosure is adapted for administration by any route, such as a route selected from intravenous route, intramuscular route, subcutaneous route, intranasal route, by aerosol and by infusion such as by rectal infusion, epidural infusion and intraperitoneal infusion.

In some embodiments, a pharmaceutical composition comprising IgA, in particular polymeric or secretory IgA as disclosed herein is used for mucosal application, in particular to the respiratory tract, preferably by nebulisation or inhalation. Pharmaceutical composition comprising IgA, in particular polymeric (e.g., J-chain dimerization of IgA) or secretory IgA are preferred as prophylactic treatment, to prevent SARS-CoV-2 infection.

In some embodiments, a pharmaceutical composition comprising IgG, preferably IgG1, is used for injection, in particular intravenous, subcutaneous or intramuscular.

These pharmaceutical compositions are exemplary only and do not limit the pharmaceutical compositions suitable for other parenteral and non-parenteral administration routes. The pharmaceutical compositions described herein can be packaged in single unit dosage or in multidosage forms.

Preferably, the pharmaceutical compositions contain vehicles, which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. Sustained release formulations, such as PLA or PLGA or other polymers, for inhalation or injection can be used.

In certain aspects, the disclosure relates to an antibody, antigen-binding fragment thereof, or pharmaceutical composition according to any one of the preceding embodiments, for use as a medicament.

In certain aspects, the disclosure provides the therapeutic use of an antibody, antigen-binding fragment thereof or a composition according to any one of the preceding embodiments, preferably for treating, preventing or alleviating the symptoms of a SARS-CoV-2-associated or -mediated disorder in a subject in need thereof.

The term "subject" or "patient" as used herein, refers to mammals. Mammalian species that can benefit from the disclosed methods of treatment include, but are not limited to, humans, non-human primates such as apes, chimpanzees, monkeys, and orangutans, domesticated animals, including dogs and cats, as well as livestock such as horses, cattle, pigs, sheep, and goats, or other mammalian species including, without limitation, mice, rats, guinea pigs, rabbits, hamsters, and the like.

As used herein, the term "treatment", "treat" or "treating" refers to any act intended to ameliorate the health status of patients such as therapy, prevention, prophylaxis and retardation of the disease. In certain embodiments, such term refers to the amelioration or eradication of a disease or symptoms associated with a disease, such as according to the present disclosure the reduction of the viral burden and/or levels of inflammation in the lungs. In other embodiments, this term refers to minimizing the spread or worsening of the disease resulting from the administration of one or more therapeutic agents to a subject with such a disease.

In a further aspect, the disclosure relates to the pharmaceutical composition described herein, for use as a medicament; in particular for use in a method for preventing and/or reducing the likelihood of occurrence and/or treating a SARS-CoV-2 infection and associated COVID-19 disease.

In a further aspect, the disclosure relates to a method of treating and/or reducing the risk of developing SARS-CoV-2-associated disorder, in a subject in need thereof that comprises administering to the subject a therapeutically effective amount of an antibody, an antigen-binding fragment thereof, a nucleic acid or vector, or a pharmaceutical composition as described above.

In some embodiments of the said method, the risk of hospitalization is reduced.

In some embodiments of the said method, the risk of death is reduced.

In a further aspect, the disclosure relates to the antibody as described herein, or antigen-binding fragment thereof, the nucleic acid or vector according as described herein, or the pharmaceutical composition as described herein, for use as a medicament; in particular for use in a method for preventing and/or reducing the likelihood of occurrence and/or treating a SARS-CoV-2 infection and associated COVID-19 disease.

In a further aspect, the disclosure relates to the antibody as described herein, or antigen-binding fragment thereof, the nucleic acid or vector according as described herein, or the pharmaceutical composition as described herein, for use as a medicament; in particular for use in a method for preventing and/or reducing the likelihood of occurrence and/or treating a SARS-CoV-2 infection and associated COVID-19 disease.

In a further aspect, the disclosure relates to the antibody as described herein, or antigen-binding fragment thereof, the nucleic acid or vector according as described herein, or the pharmaceutical composition as described herein, for use as a medicament for a human mammal.

In a further aspect, the disclosure relates to the antibody as described herein, or antigen-binding fragment thereof, the nucleic acid or vector according as described herein, or the pharmaceutical composition as described herein, for use as a medicament in combination with a vaccine against a Coronaviridae infection, in particular of a SARS-CoV-2 infection.

In a further aspect, the disclosure relates to the antibody as described herein, or antigen-binding fragment thereof, the nucleic acid or vector according as described herein, or the pharmaceutical composition as described herein, for use for use as a medicament in combination with a second antibody which specifically neutralizes the Severe Acute Respiratory Syndrome-related Coronavirus 2 (SARS-CoV-2), said second antibody being not a competitive inhibitor of binding to the RBD with the first antibody.

In a further aspect, the disclosure relates to the antibody as described herein, or antigen-binding fragment thereof, the nucleic acid or vector according as described herein, or the pharmaceutical composition as described herein, for use as a medicament in combination with a second antibody which specifically binds to a viral Spike protein receptor-binding domain (RBD) of a Severe Acute Respiratory Syndrome-related Coronavirus 2 (SARS-CoV-2), said second antibody being not a competitive inhibitor of binding to the RBD with the first antibody.

In a further aspect, the disclosure relates to the antibody as described herein, or antigen-binding fragment thereof, the nucleic acid or vector according as described herein, or the pharmaceutical composition as described herein, for use as a medicament in combination with a second antibody which specifically binds to a viral Spike protein receptor-binding domain (RBD) of a Severe Acute Respiratory Syndrome-related Coronavirus 2 (SARS-CoV-2), said second antibody being a class 2 or class 3 anti-SARS-CoV2 Spike protein antibody.

In a further aspect, the disclosure relates to the antibody as described herein, or antigen-binding fragment thereof, the nucleic acid or vector according as described herein, or the pharmaceutical composition as described herein, for use as a medicament in combination with a second antibody selected from the group of at least one of the following reference antibodies: (i) antibodies directed against RBD selected from Adintrevimab, VYD222 antibody, SA55 antibody, Cilgavimab, Imdevimab, and Sotrovimab, (ii) anti-S2 antibodies directed against the fusion peptide such as C77G12 antibody, 76E1 antibody or COV4462 antibody, (iii) antibodies directed against the HR2 region, such as Cv2.3132 and (iv) antibodies directed against the S2 stem helix.

The present disclosure also pertains to a pharmaceutical composition comprising:
(i) an antibody of the present disclosure, or antigen-binding fragment thereof, nucleic acid or vector as described herein, or pharmaceutical composition as described herein;
(ii) an antibody selected from the group of at least one of the following reference antibodies (i) antibodies directed against RBD selected from Adintrevimab, VYD222 antibody, SA55 antibody, Cilgavimab, Imdevimab, and Sotrovimab, (ii) anti-S2 antibodies directed against the fusion peptide such as C77G12 antibody, 76E1 antibody or COV4462 antibody, (iii) antibodies directed against the HR2 region, such as Cv2.3132 and (iv) antibodies directed against the S2 stem helix.

The present disclosure further concerns a method of treating a SARS-CoV-2-associated disease in a subject, comprising administering an effective amount of an antibody according the present description, or antigen-binding fragment thereof, in combination with an antibody selected from (i) antibodies directed against RBD selected from Adintrevimab, VYD222 antibody, SA55 antibody, Cilgavimab, Imdevimab, and Sotrovimab, (ii) anti-S2 antibodies directed against the fusion peptide such as C77G12 antibody, 76E1 antibody or COV4462 antibody, (iii) antibodies directed against the HR2 region, such as Cv2.3132 and (iv) antibodies directed against the S2 stem helix.

In a further aspect, the disclosure relates to the antibody as described herein, or antigen-binding fragment thereof, the nucleic acid or vector according as described herein, or the pharmaceutical composition as described herein, for use in a method for preventing and/or reducing the likelihood of occurrence of a Coronaviridae infection; in particular a SARS-CoV-2 infection.

In a further aspect, the disclosure relates to the antibody as described herein, or antigen-binding fragment thereof, the nucleic acid or vector according as described herein, or the pharmaceutical composition as described herein, for use in a method for preventing and/or reducing the likelihood of occurrence of a complication of a Coronaviridae infection, in particular of a respiratory, nervous, gastrointestinal or cardiovascular complication of a Coronaviridae infection; in particular of a SARS-CoV-2 infection.

In a further aspect, the disclosure relates to the antibody as described herein, or antigen-binding fragment thereof, the nucleic acid or vector according as described herein, or the pharmaceutical composition as described herein, for use in a method for preventing and/or reducing the likelihood of occurrence of a severe acute respiratory complication of a Coronaviridae infection; in particular of a SARS-CoV-2 infection.

In a further aspect, the disclosure relates to the antibody as described herein, or antigen-binding fragment thereof, the nucleic acid or vector according as described herein, or the pharmaceutical composition as described herein, for use in a method for preventing and/or reducing the likelihood of occurrence of a severe acute respiratory complication of a Coronaviridae infection; in particular of a SARS-CoV-2 infection.

In a further aspect, the disclosure relates to the antibody as described herein, or antigen-binding fragment thereof, the nucleic acid or vector according as described herein, or the pharmaceutical composition as described herein, for use for use in a method for preventing and/or reducing the likelihood of occurrence of a Coronaviridae infection in an individual, said individual being characterized in that
the individual has not been administered a vaccine against the said Coronaviridae infection; or
the individual is not responding to the said vaccine; or the individual's level of antibodies directed against the Coronaviridae infection is at or below a protecting threshold level.

In a further aspect, the disclosure relates to the antibody as described herein, or antigen-binding fragment thereof, the nucleic acid or vector according as described herein, or the pharmaceutical composition as described herein, for use in a method for improving an immune response against a Coronaviridae virus; in particular of a SARS-CoV-2 infection.

In a further aspect, the disclosure relates to the antibody as described herein, or antigen-binding fragment thereof, the nucleic acid or vector according as described herein, or the pharmaceutical composition as described herein, for use in a method for improving an immune response against a viral Spike protein receptor-binding domain (RBD) of a Coronaviridae virus; or a fragment thereof.

In a further aspect, the disclosure relates to the use of an antibody of the present description, or antigen-binding fragment thereof, or pharmaceutical composition as described herein, for the manufacture of a medicament for the prevention or treatment of SARS-CoV-2 infection and associated COVID-19 disease.

In some embodiments, the subject is not infected with SARS-CoV-2 and the treatment is a prophylactic treatment.

In some particular embodiments, the method is a method of reducing the risk of developing a SARS-CoV-2-associated COVID-19 disease, wherein the risk of hospitalization or the risk of death is reduced by the treatment. In some particular embodiments, the reduction of the risk of developing a SARS-CoV-2 associated COVID-19 disease lasts at least 3 or 4 months, preferably 5 or 6 months, more preferably 7 to 9 months, after administration to the subject of a therapeutically effective amount of an antibody, an antigen-binding fragment thereof, a nucleic acid or vector, or a pharmaceutical composition as described above.

In some embodiments, the subject is a COVID-19 patient and the treatment is a curative treatment.

The present disclosure further pertains to a method of treating a SARS-CoV-2-associated disease in a subject, comprising administering an effective amount of the antibody as described herein, or antigen-binding fragment thereof, the nucleic acid or vector according as described herein, or the pharmaceutical composition as described herein, In some embodiments of the said method, the risk of developing severe disease is reduced by the treatment.

In some embodiments of the said method, the subject is hospitalized.

In some embodiments of the methods for treating a SARS-CoV-2-associated disease of the present disclosure, the subject is at risk of developing a SARS-CoV-2-associated disease, more particularly a subject with concurrent underlying conditions such as obesity, diabetes, cancer, under immunosuppressive therapy, primary immune deficiency or unresponsive to vaccines.

In some particular embodiments, the method is a method of treating SARS-CoV-2-associated COVID-19 disease, wherein the likelihood of developing severe disease is reduced by the treatment; wherein the likelihood of hospitalization is reduced by the treatment; wherein the subject is hospitalized.

In some particular embodiments, the method is a method of treating SARS-CoV-2-associated COVID-19 disease, wherein the subject is at risk of developing a SARS, more particularly a subject with concurrent underlying conditions such as obesity, diabetes, cancer, under immunosuppressive therapy, primary immune deficiency or unresponsive to vaccines. Non-limiting examples of subjects with concurrent underlying conditions include a subject receiving anti-CD20 antibody therapy, a subject having a lymphoid homeopathy, a solid organ transplant recipient or an allogeneic hematopoietic stem cell transplant recipient.

In the context of the invention, an "effective amount" means a therapeutically effective amount. As used herein a "therapeutically effective amount" refers to an amount effective, at dosages and for periods of time necessary to achieve the desired therapeutic result, such as prophylaxis, or treatment of SARS-CoV-2-infection and in particular the reduction of the viral burden and/or levels of inflammation in the lungs. The therapeutically effective amount of the product of the invention, or pharmaceutical composition that comprises it may vary according to factors such as the disease state, age, sex, and weight of the individual, and the ability of the product or pharmaceutical composition to elicit a desired response in the individual. Dosage regimens may be adjusted to provide the optimum therapeutic response. A therapeutically effective amount is also typically one in which any toxic or detrimental effect of the product or pharmaceutical composition is outweighed by the therapeutically beneficial effects.

The product of the disclosure will be typically included in a pharmaceutical composition or medicament, optionally in combination with a pharmaceutical carrier, diluent and/or adjuvant. Such composition or medicinal product comprises the product of the disclosure in an effective amount, sufficient to provide a desired therapeutic effect, and a pharmaceutically acceptable carrier or excipient.

In one embodiment the antibody or antigen-binding fragment or the pharmaceutical composition for its therapeutic use is administered to the subject or patient by a parenteral route, in particularly by intravenous, intraarterial, subcutaneous, intraperitoneal, or intramuscular route. In another particular embodiment, the antibody or antigen-binding fragment or the pharmaceutical composition for its therapeutic use is administered to the subject or patient by inhalation.

The amount of product of the invention that is administered to the subject or patient may vary depending on the particular circumstances of the individual subject or patient including, age, sex, and weight of the individual; the nature and stage of the disease, the aggressiveness of the disease; the route of administration; and/or concomitant medication that has been prescribed to the subject or patient. Dosage regimens may be adjusted to provide the optimum therapeutic response.

For any particular subject, specific dosage regimens may be adjusted over time according to the individual needs and the professional judgment of the person administering or supervising the administration of the compositions. Dosage ranges set forth herein are exemplary only and do not limit the dosage ranges that may be selected by medical practitioners.

In one embodiment, the antibody or antigen-binding fragment according to the disclosure can be administered to the subject or patient for the treatment of SARS-CoV-2 associated disease in an amount or dose comprised within a range of 2.5 mg/kg to 40 mg/kg (kg: subject's or patient's body weight). In a more particular embodiment, the antibody or antigen-binding fragment is administered in an amount comprised within a range of 5 to 30 mg/kg. In a more particular embodiment, the antibody or antigen-binding fragment is administered in an amount comprised within a range of 8.5 to 28.5 mg/kg for a person weighing 70 kg. In a more particular embodiment, the antibody or antigen-binding fragment is administered at a dosage of at least 5 mg/kg, preferably 10 mg/kg, more preferably 15 mg/kg, and more preferably 30 mg/kg.

In some embodiments, the pharmaceutical composition is included in a kit that may further comprise instructions or packaging materials that describe how to administer the product contained within the kit to a patient. Containers of the kit can be of any suitable material, e.g., glass, plastic, metal, etc., and of any suitable size, shape, or configuration. In certain embodiments, the kits may include one or more ampoules or syringes that contain the products of the invention in a suitable liquid or solution form.

Another aspect of the invention relates to a kit comprising an antibody according to the present disclosure, or antigen-binding fragment thereof, nucleic acid or vector as described herein, or pharmaceutical composition as described herein.

In some embodiments, the kit further comprising an antibody selected from the group of at least one of the following reference antibodies: (i) antibodies directed against RBD selected from Adintrevimab, VYD222 antibody, SA55 antibody, Cilgavimab, Imdevimab, and Sotrovimab, (ii) anti-S2 antibodies directed against the fusion peptide such as C77G12 antibody, 76E1 antibody or COV4462 antibody, (iii) antibodies directed against the HR2 region, such as Cv2.3132 and (iv) antibodies directed against the S2 stem helix.

Another aspect of the invention relates to a medical device, comprising the pharmaceutical composition according to the present disclosure. The medical device is in a form suitable for the administration of the composition. In some embodiments, the medical device is suitable for the injection of the composition; said medical device is advantageously chosen from a syringe, infusion bag, injection port, and others that are well-known in the art. In other embodiments, the medical device is suitable for the respiratory tract administration of the composition; said medical device is advantageously chosen from an inhaler, a nebulizer, such as small-volume nebulizer, and others that are well-known in the art.

Another aspect of the invention relates to the use of a pharmaceutical composition according to the present disclosure for the manufacture of a medicament for the prevention or treatment of SARS-CoV-2 infection and associated COVID-19 disease.

Diagnostic Reagents, Kits and Methods

The antibodies or fragment thereof comprising the antigen-binding site according to the present disclosure are specific for SARS-CoV-2. Therefore, they are useful as reagent for the detection of SARS-CoV-2 infection or contamination in various samples, including in particular biological or environmental samples.

The sample is any sample suspected of containing SARS-CoV-2 such as in particular biological or environmental samples. A biological sample may be any tissue, body fluid or stool. Non-limiting examples of body fluids include whole-blood, serum, plasma, urine, cerebral spinal fluid (CSF), and mucosal secretions, such as with no limitations oral and respiratory tract secretions (sputa, saliva and the like). Samples include swabs such as oral or nasopharyngeal (NP) swabs, aspirate, wash or lavage. Samples for diagnostic tests for SARS-CoV-2 can be taken from the upper (nasopharyngeal/oropharyngeal swabs, nasal aspirate, nasal wash or saliva) or lower respiratory tract (sputum or tracheal aspirate or bronchoalveolar lavage (BAL). Preferred biological samples include nasopharyngeal swab and saliva sample. Samples also include environmental samples that may contain SARS-CoV-2 such as air, water, soil, food, beverages, feed, water (e.g., fresh water, salt water, waste water, and drinking water), sewage, sludge, environmental surfaces and others. The environmental surface sample is for example a surface swab or swipe.

The detection or diagnosis is performed by immunoassay technique which is well-known in the art and rely on the detection of antigen-antibody complexes using an appropriate label. The method of the invention may use any immunoassay such as with no limitations, immunoblotting, immunoprecipitation, ELISA, immunocytochemistry or immunohistochemistry, and immunofluorescence like flow cytometry assay, and FACS. Flow cytometry, also known as flow virometry, nanoscale flow cytometry or simply small-particle flow cytometry is a rapid, high-throughput, and effective method to quantify intact viral particles released by an infected cell.

The invention encompasses a method for the detection of a SARS-CoV-2 in a sample comprising: contacting said sample with an antibody according to the present disclosure and detecting the antigen-antibody complexes formed, thereby detecting the presence, absence or level of SARS-CoV-2 in the sample.

In some embodiments of the method above, the sample is a biological or environmental sample.

In some embodiments of the method above, the sample is from a human or non-human mammal.

In some embodiments of the method above, the sample is a biological sample from a subject suspected to be contaminated with SARS-CoV-2 and the method is for the diagnosis of SARS-CoV-2 infection and associated COVID-19 disease.

In some embodiments of the method above, the sample is a biological sample from a COVID-19 patient before or during treatment of COVID-19 disease and the method is for the monitoring of treatment of COVID-19 disease.

The method of the invention may use any appropriate label used in immunoassays such as enzymes, chemiluminescent, fluorescent dyes/proteins or radioactive agents, or others. The label may be on the antibody or fragment thereof which binds to the antigen or on a binding-partner such as secondary antibody or avidin/streptavidin conjugated to a label.

The antibody is preferably labelled, in the form of a conjugate or fusion protein, and the antigen-antibody complexes are detected by measuring the signal from the label by any appropriate means available for that purpose as disclosed above.

In some embodiments, antigen detection is performed by ELISA, lateral flow immunoassay, or bead-based immunoassay.

The detection step may be qualitative or semi-quantitative, and may comprise detecting the presence or level of viral antigen in the sample. In some embodiments, the detecting step comprises the determination of the amount of bound antigen in the mixture, and optionally, comparing the amount of bound antigen in the mixture with at least one predetermined value.

The detection of the presence or level of viral antigen in a biological sample from an individual using the methods of the invention is indicative of whether the individual is suffering from SARS-CoV-2 infection or associated COVID-19 disease.

Therefore, the above method of the invention is useful for the diagnosis of SARS-CoV-2 infection or associated COVID-19 disease in an individual, as well as monitoring of treatment in a COVID-19 patient.

The treatment may be an antiviral treatment or immunotherapeutic treatment using SARS-CoV-2 neutralizing antibodies.

In some embodiments, the above method is a method of diagnosis comprising the step of deducing therefrom whether the individual is suffering from SARS-CoV-2 infection or associated disease.

In some embodiments, the above method is a method of monitoring of treatment in a COVID-19 patient, comprising the step of deducing therefrom whether the treatment is efficient is not. Treatment efficacy is determined by a decrease of viral antigen level compared to previous viral antigen level determined in the patient, before treatment or during the treatment course.

In some embodiments in connection with this aspect of the invention, the above method of diagnosis comprises a further step of administering an appropriate treatment to the individual depending on whether or not the individual is diagnosed with SARS-CoV-2 virus infection and in particular COVID-19 associated disease.

In some embodiments in connection with this aspect of the invention, the above method of monitoring of treatment in a COVID-19 patient, comprises a further step of modifying the COVID-19 treatment when said treatment is determined as not being efficient in the patient.

In another aspect, the disclosure further relates to a kit for the detection or diagnosis of SARS-CoV-2 infection or contamination, comprising at least an antibody or antigen-binding fragment thereof, preferably further including a detectable label. The kit optionally comprises reagents for the detection of the antigen/antibody complex. Reagents available for this purpose are well-known in the art and include with no limitation buffers, secondary antibody conjugated to a label, avidin/streptavidin conjugated to a label. In some preferred embodiments of the kit of the invention, the antibody, and optional reagents are in lyophilised form to allow ambient storage. The components of the kits are packaged together into any of the various containers suitable for antigen/antibody complex detection such as plates, slides, wells, dishes, beads, particles, cups, strands, chips, strips and others. The kit optionally includes instructions for performing at least one specific embodiment of the method of the invention. In some advantageous embodiments, the kit comprises micro-well plates or microtubes, preferably in a dried format, i.e., wherein the wells of the plates or microtubes comprise a dried composition containing at least the antibody, and preferably further comprising all the reagents for the detection of antigen/antibody complex. In some other advantageous embodiments, the antibody and optional reagents are included into any of the devices available for immunoassay.

The practice of the present invention will employ, unless otherwise indicated, conventional techniques, which are within the skill of the art. Such techniques are explained fully in the literature.

The invention is further described by, without in any way being limited to, the following examples.

Examples

Material and Methods

Viruses

The D614G (hCoV-19/France/GE1973/2020), XBB.1.5 (GISAID EPI_ISL_16353849), XBB.1.16 (hCoV-19/France/GES-IPP7712/2023), BA.2.86 (hCoV-19/France/IDF-IPP17625/2023), EG.5.1 (hCoV-19/France/GES-IPP15954/2023) and JN.1 (hCoV-19/France/HDF-IPP21391/2023) strains were provided by the National Reference Centre for Respiratory Viruses (Institut Pasteur France). The SARS-CoV-2 viral stocks for the following strains used in the in vitro S-Fuse neutralization assay were prepared and titrated in the Viral and Immunity Unit (Institut Pasteur) as previously described (PMID: 36788246).

Expression and Purification of Viral Proteins

Trimeric SARS-CoV-2, human angiotensin-converting enzyme 2 (ACE2) ectodomain, and RBD proteins (Wuhan to BA.2) cloned into pcDNA3.1/Zeo(+) vector were previously described (Planchais et al., 2022, J Exp Med, Vol. 219 (7): e20220638). For the additional mutated SARS-CoV-2 RBD proteins (BA.4/5 to JN.1), mutations were introduced using the QuickChange Site-Directed Mutagenesis kit (Agilent Technologies) following the manufacturer's instructions or obtained with synthetic DNA fragments (GeneArt, Thermo Fisher Scientific). Recombinant proteins were produced by transient transfection of exponentially growing Freestyle 293-F suspension cells (Thermo Fisher Scientific) using polyethylenimine (PEI) precipitation method, purified from culture supernatants by high-performance chromatography using the Ni Sepharose® Excel Resin according to manufacturer's instructions (GE Healthcare), dialyzed against PBS using Slide-A-Lyzer® dialysis cassettes (Thermo Fisher Scientific), quantified using NanoDrop 2000 instrument (Thermo Fisher Scientific), and controlled for purity by SDS-PAGE using NuPAGE 3-8% Tris-acetate gels (Life Technologies) as previously described (Planchais et al., 2022, J Exp Med, Vol. 219 (7): e20220638). AviTagged tri-S and RBD proteins were biotinylated using the Enzymatic Protein Biotinylation Kit (Sigma-Aldrich).

ELISAs

ELISAs were performed as previously described (PMID: 35704748). Briefly, high-binding 96-well ELISA plates (Costar, Corning) were coated overnight with 250 ng/well of purified recombinant Coronavirus proteins. After washings with 0.05% Tween 20-PBS (washing buffer), plates were blocked 2 h with 2% BSA, 1 mM EDTA, 0.05% Tween 20-PBS (Blocking buffer), washed, and incubated with serially diluted purified IgG mAbs in PBS. Recombinant IgG1 antibodies were tested at 10 µg/ml, and 7 consecutive 1:4 dilutions in PBS. After washings, the plates were revealed by incubation for 1 h with goat HRP-conjugated anti-human IgG (Jackson ImmunoReseach, 0.8 µg/ml final) and by adding 100 µl of HRP chromogenic substrate (ABTS solution, Euromedex) after washing steps. Optical densities were measured at 405 nm ($OD_{405nm}$), and background values given by incubation of PBS alone in coated wells were subtracted. Experiments were performed using HydroSpeed™ microplate washer and Sunrise™ microplate absorbance reader (Tecan Männedorf, Switzerland). For the competition experiments of tri-S-binding to ACE2, ELISA plates (Costar, Corning) were coated overnight with 250 ng/well of purified ACE2 ectodomain. After washings, plates were blocked 2 h with Blocking buffer, PBST-washed, and incubated with recombinant IgG1 mAbs at 10 µg/ml and 7 consecutive 1:2 dilutions in presence of biotinylated tri-S protein at 1 µg/ml in PBS. After washings, the plates were revealed by incubation for 30 min with streptavidin HRP-conjugated (BD Biosciences) as described above.

HEp-2 IFA Assay

Recombinant SARS-CoV-2 S-specific and control IgG antibodies (mGO53 and ED38) at 100 µg/ml were analyzed by indirect immuno-fluorescence assay (IFA) on HEp-2 cells sections (ANA HEp-2 AeskuSlides®, Aesku.Diagnostics, Wendelsheim, Germany) using the kit's controls and FITC-conjugated anti-human IgG antibodies as the tracer according to the manufacturer' instructions. HEp-2 sections were examined using the fluorescence microscope Axio Imager 2 (Zeiss, Jena, Germany), and pictures were taken at magnification x 40 with 5000 ms-acquisition using ZEN imaging software (Zen 2.0 blue version, Zeiss) at the Imagopole platform (Institut Pasteur).

SARS-CoV-2 S-Fuse Neutralization Assay

S-Fuse cells (1:1 mix of U2OS-ACE2-GFP1-10 and U2OS-ACE2-GFP11) were prepared and plated at a density of $2 \times 10^4$ per well in a µClear 96-well plate (Greiner Bio-One) as previously described (PMID: 36788246). SARS-CoV-2 VOC viruses (MOI 0.1) were incubated with recombinant IgG1 mAbs at 100 µg/ml, and 17 consecutive 1:2 dilutions in culture medium for 30 min at room temperature and added to S-Fuse cells. The cells were fixed, 18 h later, in 4% paraformaldehyde, washed and stained with Hoechst stain (dilution 1:10,000; Invitrogen). Images were acquired with an Opera Phenix high-content confocal microscope (Perkin Elmer). The area displaying GFP expression, and the number of nuclei were quantified with Harmony software 4.8 (Perkin Elmer). The percentage neutralization was calculated from the number of syncytia as follows: 100×(1−(value with IgG-value in "non-infected")/(value in "no IgG"–value in "non-infected")). $IC_{50}$ values were calculated using Prism software (v.9.3.1, GraphPad Prism Inc.) by fitting replicate values using the four-parameters dose-response model (variable slope). $IC_{50}$ values (µg/ml) were calculated based on a reconstructed curve of the percentage neutralization at the various concentrations indicated.

Multiplex Bead-Based Binding Assay

Antibody cross-reactivity to self-antigens was evaluated by multiplex autoantigen-binding assay using the Milliplex® Human autoimmune autoantibody panel kit (Millipore) following the manufacturer's instructions. Briefly, IgG antibodies at a final concentration of 25 µg/ml were incubated with the beads overnight at 4° C. After washings, PE-IgG conjugate was added, and mixtures were incubated at room temperature for 1 h 30. After a final washing step, readings were made on a Bio-Plex 200 instrument (BioRad). In addition to the controls provided in the kit (negative, low, medium and high positive), mGO53 and ED38 antibodies were used as negative and positive controls for polyreactivity, respectively.

Results
1. Polyreactivity and Self-Reactivity Assessment of Potent SARS-CoV-2 Neutralizing Antibodies The polyreactivity and self-reactivity of the potent SARS-CoV-2 neutralizing antibodies SPK002, A1, A2, A3, A4, A5, A6, B1, B2, C1, C2, C3, was assessed by ELISA against dsDNA (DNA), flagellin (Fla), gp140 (HIV-1 YU2), insulin (INS), keyhole limpet hemocyanin (KLH), lipopolysaccharide (LPS), lysozyme (LZ), MAPK-14 (MAPK), peptidoglycan (PG), and thyroglobulin (Tg) (FIG. 1); Hep-2 reactivity by ELISA Bioplex® Bio-Rad (FIG. 2; Polyreactivity index was determined by comparison with non-reactive antibody.

No polyreactivity, self-reactivity and off-target binding to human proteins was detected, for any of the, A1, A2, A3, A4, A5, A6, B1, B2, C1, C2, C3, antibodies.

2. Binding of Human Anti-SARS-CoV-2 Spike Antibodies

The binding of the A1, A2, A3, A4, A5, A6, B1, B2, C1, C2, C3, antibodies to the Spike RBD domain from a variety of SARS-CoV-2 variants has been assayed. The results are shown in FIG. 3. The results of FIG. 3 show that all of the A1, A2, A3, A4, A5, A6, B1, B2, C1, C2, C3, antibodies possess a large spectrum of binding to the tested SRAS-CoV-2 variants RBD domain, which include Wuhan, Delta, BA.2, BA.2.75.2, BA.4/5, BQ.11, XBB.1.5, XBB.1.16, EG.5, BA.2.86 and JN-1. A rather low binding of the A6 antibody to the RBD domain from the JN-1 variant is observed (FIG. 3).

In contrast, the parent SPK002 antibody weakly recognize, or alternatively does not recognize, the RBD domain from the BA.2.75.2, BQ.1.1, XBB.1.5, XBB.1.16, EG.5, BA.2.86 and JN-1 (FIG. 3).

A competition ELISA assay has been performed for measuring the blockage of RBD binding to ACE2 ectodomain. The results are shown in FIG. 4.

The results of FIG. 4 show that all of the A1, A2, A3, A4, A5, A6, B1, B2, C1, C2, C3 antibodies possess a large spectrum of blocking the ACE2 ectodomain binding to the tested SRAS-CoV-2 variants RBD domain, which include Wuhan, Delta, BA.2, BA.2.75.2, BA.4/5, BQ.11, XBB.1.5, XBB.1.16, EG.5, BA.2.86 and JN-1. A rather low blocking of the ACE2 ectodomain to the RBD domain from the JN-1 variant is however observed for most of the tested antibodies (FIG. 4).

The results of FIG. 4 show that the antibodies having the largest antiviral spectrum are antibodies A1, B1 and C1, and especially antibodies A1 and C1.

In contrast, the parent SPK002 antibody weakly block, or alternatively does not block, the binding of the ACE2 ectodomain to the RBD domain from the BA.2.75.2, BQ.1.1, XBB.1.5, XBB.1.16, EG.5, BA.2.86 and JN-1 (FIG. 4).

3. Antiviral Properties

Antiviral properties of the A1, A2, A3, A4, A5, A6, B1, B2, C1, C2, C3 antibodies have been assessed by a neutralizing assay using live viruses called S-Fuse.

The results of the S-Fuse neutralization assay are summarized in FIG. 5.

The results which are summarized in FIG. 5 show that the A1, A2, A3, A4, A5, A6, B1, B2, C1, C2, C3 antibodies have significant antiviral properties against a plurality of the SARS-CoV-2 variants tested, which include D614G, XBB.1.5, XBB.1.16, BA.2.86 and EG.5.1.

The antibodies having the largest spectrum of antiviral properties are the A1, B1 and C1 antibodies, which further substantially neutralize the SARS-CoV-2 variant JN.1. (FIG. 5).

TABLE of sequences

| SED ID NO. SPK002 MA1 | Sequence | Description |
|---|---|---|
| 1 | SNYMS | SPK002M-A1 HCDR1 Also found in A2, A3, A4, A5, A6, B1, B2, C1, C2, C3 |
| 2 | VIYPGGSTFYADSVKG | SPK002M-A1 HCDR2 Also found in A2, A3, A4, A5, A6, B1, B2, C3 |
| 3 | DLVVYGMDV | SPK002M-A1 HCDR3 Also found in A2, A3, A4, A5, A6, B1, B2, C1, C2, C3 |
| 4 | EVQLVESGGGLIQPGGSLRLSCAASTITVT | SPK002M-A1 HFR1 Also found in A2, A3 |
| 5 | WVRQAPGKGLEWVS | SPK002M A1 HFR2 Also found in A2, A3, A4, A5, A6, B1, B2, C1, C2, C3 |
| 6 | RFTISADNSKNTLYLQMNSLRAEDTAVYYCAR | SPK002M A1 HFR3 Also found in A2, A3, A4, A5, A6 |

TABLE of sequences

| SED ID NO. SPK002 MA1 | Sequence | Description |
| --- | --- | --- |
| 7 | WGQGTTVTVSS | SPK002M A1 HFR4 Also found in A2, A3, A4, A5, A6, B1, B2, C1, C2, C3 |
| 8 | EVQLVESGGGLIQPGGSLRLSCAASTITVTSNYMSWVRQAPGK GLEWVSVIYPGGSTFYADSVKGRFTISADNSKNTLYLQMNSLR AEDTAVYYCARDLVVYGMDVWGQGTTVTVSS | SPK002M A1 heavy chain variable domain |
| 9 | RASQGESSSYLA | SPK002M-A1 LCDR1 |
| 10 | GASSRAT | SPK002M-A1 LCDR2 Also found in A2, A3, A4, A5, A6, B1, B2, C1, C2, C3 |
| 11 | QQGVT | SPK002M-A1 LCDR3 Also found in A2, A3, A4, A5, A6, B2, C2, C3 |
| 12 | EIVLTQSPGTLSLSPGERATLSC | SPK002M-A1 LFR1 Also found in A2, A3, A4, A5, A6, B1, B2, C1, C2, C3 |
| 13 | WYQQKPGQAPRLLIY | SPK002M-A1 LFR2 Also found in A2, A3, A4, A5, A6, B1, B2, C1, C2, C3 |
| 14 | GIPGRFSGSGSGTDFTLTISRLEPEDFAVYYC | SPK002M-A1 LFR3 Also found in A2, A3, A4, C1, C2, C3 |
| 15 | FGGGTKVEIK | SPK002M-A1 LFR4 Also found in A2, A3, A4, A5, A6, B1, B2, C1, C2, C3 |
| 16 | EIVLTQSPGTLSLSPGERATLSCRASQGFSSSYLAWYQQKPGQ APRLLIYGASSRATGIPGRFSGSGSGTDFTLTISRLEPEDFAV YYCQQGVTFGGGTKVEIK | SPK002M A1 light chain variable domain |
| 17 | EVQLVESGGGLIQPGGSLRLSCAASVITVT | SPK002M A4 HFR1 Also found in A5 |
| 18 | EVQLVESGGGLIQPGGSLRLSCAASGITVT | SPK002M A6 HFR1 |
| 19 | EVQLVESGGGLIQPGGSLRLSCAASIITVT | SPK002M B1 HFR1 Also found in B2, C1, C2, C3 |
| 20 | VAYPGGSTFYADSVKG | SPK002M C1 HCDR2 Also found in C2 |
| 21 | RFTISYDNSKNTLYLQMNSLRAEDTAVYYCAR | SPK002M B1 HFR3 = B2 |
| 22 | RFTISTDNSKNTLYLQMNSLRAEDTAVYYCAR | SPK002M C1 HFR3 Also found in C2, C3 |
| 23 | RASQGVSSSYLA | SPK002M A2 LCDR1 |

-continued

TABLE of sequences

| SED ID NO. SPK002 MA1 | Sequence | Description |
|---|---|---|
| 24 | RASQSVSSSYLA | SPK002M A3 LCDR1 Also found in A4, A5, A6, B2, C2, C3 |
| 25 | RASQSVSDSYLA | SPK002M B1 LCDR1 Also found in C1 |
| 26 | GIPGRFSGSGSGTDFTLTISRLEPEDFAIYYC | SPK002M A5 LFR3 Also found in A6, B1, B2 |
| 27 | QYGVTF | SPK002M B1 LCDR3 Also found in C1 |
| 28 | RFTISXDNSKNTLYLQMNSLRAEDTAVYYCAR | SPK002M HFR3 with X being a variable amino acid at position 71 of the heavy chain variable domain |
| 29 | EVQLVESGGGLIQPGGSLRLSCAASTITVTSNYMSWVRQAPGKGLEWVSVIYPGGSTFYADSVKGRFTISADNSKNTLYLQMNSLRAEDTAVYYCARDLVVYGMDVWGQGTTVTVSS | SPK002M A2 Heavy chain variable domain |
| 30 | EIVLTQSPGTLSLSPGERATLSCRASQGVSSSYLAWYQQKPGQAPRLLIYGASSRATGIPGRFSGSGSGTDFTLTISRLEPEDFAVYYCQQGVTFGGGTKVEIK | SPK002M A2 Light chain variable domain |
| 31 | EVQLVESGGGLIQPGGSLRLSCAASTITVTSNYMSWVRQAPGKGLEWVSVIYPGGSTFYADSVKGRFTISADNSKNTLYLQMNSLRAEDTAVYYCARDLVVYGMDVWGQGTTVTVSS | SPK002M A3 Heavy chain variable domain |
| 32 | EIVLTQSPGTLSLSPGERATLSCRASQSVSSSYLAWYQQKPGQAPRLLIYGASSRATGIPGRFSGSGSGTDFTLTISRLEPEDFAVYYCQQGVTFGGGTKVEIK | SPK002M A3 Light chain variable domain |
| 33 | EVQLVESGGGLIQPGGSLRLSCAASVITVTSNYMSWVRQAPGKGLEWVSVIYPGGSTFYADSVKGRFTISADNSKNTLYLQMNSLRAEDTAVYYCARDLVVYGMDVWGQGTTVTVSS | SPK002M A4 Heavy chain variable domain |
| 34 | EIVLTQSPGTLSLSPGERATLSCRASQSVSSSYLAWYQQKPGQAPRLLIYGASSRATGIPGRFSGSGSGTDFTLTISRLEPEDFAVYYCQQGVTFGGGTKVEIK | SPK002M A4 Light chain variable domain |
| 35 | EVQLVESGGGLIQPGGSLRLSCAASVITVTSNYMSWVRQAPGKGLEWVSVIYPGGSTFYADSVKGRFTISADNSKNTLYLQMNSLRAEDTAVYYCARDLVVYGMDVWGQGTTVTVSS | SPK002M A5 Heavy chain variable domain |
| 36 | EIVLTQSPGTLSLSPGERATLSCRASQSVSSSYLAWYQQKPGQAPRLLIYGASSRATGIPGRFSGSGSGTDFTLTISRLEPEDFAIYYCQQGVTFGGGTKVEIK | SPK002M A5 Light chain variable domain |
| 37 | EVQLVESGGGLIQPGGSLRLSCAASGITVTSNYMSWVRQAPGKGLEWVSVIYPGGSTFYADSVKGRFTISADNSKNTLYLQMNSLRAEDTAVYYCARDLVVYGMDVWGQGTTVTVSS | SPK002M A6 Heavy chain variable domain |
| 38 | EIVLTQSPGTLSLSPGERATLSCRASQSVSSSYLAWYQQKPGQAPRLLIYGASSRATGIPGRFSGSGSGTDFTLTISRLEPEDFAIYYCQQGVTFGGGTKVEIK | SPK002M A6 Light chain variable domain |
| 39 | EVQLVESGGGLIQPGGSLRLSCAASIITVTSNYMSWVRQAPGKGLEWVSVIYPGGSTFYADSVKGRFTISYDNSKNTLYLQMNSLRAEDTAVYYCARDLVVYGMDVWGQGTTVTVSS | SPK002M B1 Heavy chain variable domain |
| 40 | EIVLTQSPGTLSLSPGERATLSCRASQSVSDSYLAWYQQKPGQAPRLLIYGASSRATGIPGRFSGSGSGTDFTLTISRLEPEDFAIYYCQYGVTFGGGTKVEIK | SPK002M B1 Light chain variable domain |

-continued

TABLE of sequences

| SED ID NO. SPK002 MA1 | Sequence | Description |
|---|---|---|
| 41 | EVQLVESGGGLIQPGGSLRLSCAASIITVTSNYMSWVRQAPGK GLEWVSVIYPGGSTFYADSVKGRFTISYDNSKNTLYLQMNSLR AEDTAVYYCARDLVVYGMDVWGQGTTVTVSS | SPK002M B2 Heavy chain variable domain |
| 42 | EIVLTQSPGTLSLSPGERATLSCRASQSVSSSYLAWYQQKPGQ APRLLIYGASSRATGIPGRFSGSGSGTDFTLTISRLEPEDFAI YYCQQGVTFGGGTKVEIK | SPK002M B2 Light chain variable domain |
| 43 | EVQLVESGGGLIQPGGSLRLSCAASIITVTSNYMSWV RQAPGKGLEWVSVAYPGGSTFYADSVKGRFTISTDNS KNTLYLQMNSLRAEDTAVYYCARDLVVYGMDVWGQGT TVTVSS | SPK002M C1 Heavy chain variable domain |
| 44 | EIVLTQSPGTLSLSPGERATLSCRASQSVSDSYLAWY QQKPGQAPRLLIYGASSRATGIPGRFSGSGSGTDFTL TISRLEPEDFAVYYCQYGVTFGGGTKVEIK | SPK002M C1 Light chain variable domain |
| 45 | EVQLVESGGGLIQPGGSLRLSCAASIITVTSNYMSWV RQAPGKGLEWVSVAYPGGSTFYADSVKGRFTISTDNS KNTLYLQMNSLRAEDTAVYYCARDLVVYGMDVWGQGT TVTVSS | SPK002M C2 Heavy chain variable domain |
| 46 | EIVLTQSPGTLSLSPGERATLSCRASQSVSSSYLAWYQQKPGQ APRLLIYGASSRATGIPGRFSGSGSGTDFTLTISRLEPEDFAV YYCQQGVTFGGGTKVEIK | SPK002M C2 Light chain variable domain |
| 47 | EVQLVESGGGLIQPGGSLRLSCAASIITVTSNYMSWV RQAPGKGLEWVSVIYPGGSTFYADSVKGRFTISTDNS KNTLYLQMNSLRAEDTAVYYCARDLVVYGMDVWGQGT TVTVSS | SPK002M C3 Heavy chain variable domain |
| 48 | EIVLTQSPGTLSLSPGERATLSCRASQSVSSSYLAWY QQKPGQAPRLLIYGASSRATGIPGRFSGSGSGTDFTL TISRLEPEDFAVYYCQQGVTFGGGTKVEIK | SPK002M C3 Light chain variable domain |
| 49 | ASTKGPSVFPLAPSSKSTSGGTAALGCLVKDYFPEPVTVSWNSGA LTSGVHTFPAVLQSSGLYSLSSVVTVPSSSLGTQTYICNVNHKPS NTKVDKRVEPKSCDKTHTCPPCPAPELLGGPSVFLFPPKPKDTLM ISRTPEVTCVVVDVSHEDPEVKFNWYVDGVEVHNAKTKPREEQYN STYRVVSVLTVLHQDWLNGKEYKCKVSNKALPAPIEKTISKAKGQ PREPQVYTLPPSREEMTKNQVSLTCLVKGFYPSDIAVEWESNGQP ENNYKTTPPVLDSDGSFFLYSKLTVDKSRWQQGNVFSCSVMHEAL HNHYTQKSLSLSPGK | Constant Heavy chain region |
| 50 | RTVAAPSVFIFPPSDEQLKSGTASVVCLLNNFYPREAKVQWKVDN ALQSGNSQESVTEQDSKDSTYSLSSTLTLSKADYEKHKVYACEVT HQGLSSPVTKSENRGEC | Constant Light chain region |
| 51 | EVQLVESGGGLIQPGGSLRLSCAASTITVTSNYMSWVRQAPGKGL EWVSVIYPGGSTFYADSVKGRFTISADNSKNTLYLQMNSLRAEDT AVYYCARDLVVYGMDVWGQGTTVTVSSASTKGPSVFPLAPSSKST SGGTAALGCLVKDYFPEPVTVSWNSGALTSGVHTFPAVLQSSGLY SLSSVVTVPSSSLGTQTYICNVNHKPSNTKVDKRVEPKSCDKTHT CPPCPAPELLGGPSVFLFPPKPKDTLMISRTPEVTCVVVDVSHED PEVKFNWYVDGVEVHNAKTKPREEQYNSTYRVVSVLTVLHQDWLN GKEYKCKVSNKALPAPIEKTISKAKGQPREPQVYTLPPSREEMTK NQVSLTCLVKGFYPSDIAVEWESNGQPENNYKTTPPVLDSDGSFF LYSKLTVDKSRWQQGNVFSCSVMHEALHNHYTQKSLSLSPGK | SPK002M A1 full length heavy chain |
| 52 | EIVLTQSPGTLSLSPGERATLSCRASQGFSSSYLAWYQQKPGQAP RLLIYGASSRATGIPGRFSGSGSGTDFTLTISRLEPEDFAVYYCQ QGVTFGGGTKVEIKRTVAAPSVFIFPPSDEQLKSGTASVVCLLNN FYPREAKVQWKVDNALQSGNSQESVTEQDSKDSTYSLSSTLTLSK ADYEKHKVYACEVTHQGLSSPVTKSENRGEC | SPK002M A1 full length light chain |
| 53 | EVQLVESGGGLIQPGGSLRLSCAASTITVTSNYMSWVRQAPGKGL EWVSVIYPGGSTFYADSVKGRFTISADNSKNTLYLQMNSLRAEDT AVYYCARDLVVYGMDVWGQGTTVTVSSASTKGPSVFPLAPSSKST SGGTAALGCLVKDYFPEPVTVSWNSGALTSGVHTFPAVLQSSGLY SLSSVVTVPSSSLGTQTYICNVNHKPSNTKVDKRVEPKSCDKTHT CPPCPAPELLGGPSVFLFPPKPKDTLMISRTPEVTCVVVDVSHED | SPK002M A2 full length heavy chain |

| SEQ ID NO. SPK002 MA1 | Sequence | Description |
|---|---|---|
| | PEVKFNWYVDGVEVHNAKTKPREEQYNSTYRVVSVLTVLHQDWLN GKEYKCKVSNKALPAPIEKTISKAKGQPREPQVYTLPPSREEMTK NQVSLTCLVKGFYPSDIAVEWESNGQPENNYKTTPPVLDSDGSFF LYSKLTVDKSRWQQGNVFSCSVMHEALHNHYTQKSLSLSPGK | |
| 54 | EIVLTQSPGTLSLSPGERATLSCRASQGVSSSYLAWYQQKPGQAP RLLIYGASSRATGIPGRFSGSGSGTDFTLTISRLEPEDFAVYYCQ QGVTFGGGTKVEIKRTVAAPSVFIFPPSDEQLKSGTASVVCLLNN FYPREAKVQWKVDNALQSGNSQESVTEQDSKDSTYSLSSTLTLSK ADYEKHKVYACEVTHQGLSSPVTKSENRGEC | SPK002M A2 full length light chain |
| 55 | EVQLVESGGGLIQPGGSLRLSCAASTITVTSNYMSWVRQAPGKGL EWVSVIYPGGSTFYADSVKGRFTISADNSKNTLYLQMNSLRAEDT AVYYCARDLVVYGMDVWGQGTTVTVSSASTKGPSVFPLAPSSKST SGGTAALGCLVKDYFPEPVTVSWNSGALTSGVHTFPAVLQSSGLY SLSSVVTVPSSSLGTQTYICNVNHKPSNTKVDKRVEPKSCDKTHT CPPCPAPELLGGPSVFLFPPKPKDTLMISRTPEVTCVVVDVSHED PEVKFNWYVDGVEVHNAKTKPREEQYNSTYRVVSVLTVLHQDWLN GKEYKCKVSNKALPAPIEKTISKAKGQPREPQVYTLPPSREEMTK NQVSLTCLVKGFYPSDIAVEWESNGQPENNYKTTPPVLDSDGSFF LYSKLTVDKSRWQQGNVFSCSVMHEALHNHYTQKSLSLSPGK | SPK002M A3 full length heavy chain |
| 56 | EIVLTQSPGTLSLSPGERATLSCRASQSVSSSYLAWYQQKPGQAP RLLIYGASSRATGIPGRFSGSGSGTDFTLTISRLEPEDFAVYYCQ QGVTFGGGTKVEIKRTVAAPSVFIFPPSDEQLKSGTASVVCLLNN FYPREAKVQWKVDNALQSGNSQESVTEQDSKDSTYSLSSTLTLSK ADYEKHKVYACEVTHQGLSSPVTKSENRGEC | SPK002M A3 full length light chain |
| 57 | EVQLVESGGGLIQPGGSLRLSCAASVITVTSNYMSWVRQAPGKGL EWVSVIYPGGSTFYADSVKGRFTISADNSKNTLYLQMNSLRAEDT AVYYCARDLVVYGMDVWGQGTTVTVSSASTKGPSVFPLAPSSKST SGGTAALGCLVKDYFPEPVTVSWNSGALTSGVHTFPAVLQSSGLY SLSSVVTVPSSSLGTQTYICNVNHKPSNTKVDKRVEPKSCDKTHT CPPCPAPELLGGPSVFLFPPKPKDTLMISRTPEVTCVVVDVSHED PEVKFNWYVDGVEVHNAKTKPREEQYNSTYRVVSVLTVLHQDWLN GKEYKCKVSNKALPAPIEKTISKAKGQPREPQVYTLPPSREEMTK NQVSLTCLVKGFYPSDIAVEWESNGQPENNYKTTPPVLDSDGSFF LYSKLTVDKSRWQQGNVFSCSVMHEALHNHYTQKSLSLSPGK | SPK002M A4 full length heavy chain |
| 58 | EIVLTQSPGTLSLSPGERATLSCRASQSVSSSYLAWYQQKPGQAP RLLIYGASSRATGIPGRFSGSGSGTDFTLTISRLEPEDFAVYYCQ QGVTFGGGTKVEIKRTVAAPSVFIFPPSDEQLKSGTASVVCLLNN FYPREAKVQWKVDNALQSGNSQESVTEQDSKDSTYSLSSTLTLSK ADYEKHKVYACEVTHQGLSSPVTKSENRGEC | SPK002M A4 full length light chain |
| 59 | EVQLVESGGGLIQPGGSLRLSCAASVITVTSNYMSWVRQAPGKGL EWVSVIYPGGSTFYADSVKGRFTISADNSKNTLYLQMNSLRAEDT AVYYCARDLVVYGMDVWGQGTTVTVSSASTKGPSVFPLAPSSKST SGGTAALGCLVKDYFPEPVTVSWNSGALTSGVHTFPAVLQSSGLY SLSSVVTVPSSSLGTQTYICNVNHKPSNTKVDKRVEPKSCDKTHT CPPCPAPELLGGPSVFLFPPKPKDTLMISRTPEVTCVVVDVSHED PEVKFNWYVDGVEVHNAKTKPREEQYNSTYRVVSVLTVLHQDWLN GKEYKCKVSNKALPAPIEKTISKAKGQPREPQVYTLPPSREEMTK NQVSLTCLVKGFYPSDIAVEWESNGQPENNYKTTPPVLDSDGSFF LYSKLTVDKSRWQQGNVFSCSVMHEALHNHYTQKSLSLSPGK | SPK002M A5 full length heavy chain |
| 60 | EIVLTQSPGTLSLSPGERATLSCRASQSVSSSYLAWYQQKPGQAP RLLIYGASSRATGIPGRFSGSGSGTDFTLTISRLEPEDFAIYYCQ QGVTFGGGTKVEIKRTVAAPSVFIFPPSDEQLKSGTASVVCLLNN FYPREAKVQWKVDNALQSGNSQESVTEQDSKDSTYSLSSTLTLSK ADYEKHKVYACEVTHQGLSSPVTKSENRGEC | SPK002M A5 full length light chain |
| 61 | EVQLVESGGGLIQPGGSLRLSCAASGITVTSNYMSWVRQAPGKGL EWVSVIYPGGSTFYADSVKGRFTISADNSKNTLYLQMNSLRAEDT AVYYCARDLVVYGMDVWGQGTTVTVSSASTKGPSVFPLAPSSKST SGGTAALGCLVKDYFPEPVTVSWNSGALTSGVHTFPAVLQSSGLY SLSSVVTVPSSSLGTQTYICNVNHKPSNTKVDKRVEPKSCDKTHT CPPCPAPELLGGPSVFLFPPKPKDTLMISRTPEVTCVVVDVSHED PEVKFNWYVDGVEVHNAKTKPREEQYNSTYRVVSVLTVLHQDWLN GKEYKCKVSNKALPAPIEKTISKAKGQPREPQVYTLPPSREEMTK NQVSLTCLVKGFYPSDIAVEWESNGQPENNYKTTPPVLDSDGSFF LYSKLTVDKSRWQQGNVFSCSVMHEALHNHYTQKSLSLSPGK | SPK002M A6 full length heavy chain |

TABLE of sequences

| SED ID NO. SPK002 MA1 | Sequence | Description |
|---|---|---|
| 62 | EIVLTQSPGTLSLSPGERATLSCRASQSVSSSYLAWYQQKPGQAP RLLIYGASSRATGIPGRFSGSGSGTDFTLTISRLEPEDFAIYYCQ QGVTFGGGTKVEIKRTVAAPSVFIFPPSDEQLKSGTASVVCLLNN FYPREAKVQWKVDNALQSGNSQESVTEQDSKDSTYSLSSTLTLSK ADYEKHKVYACEVTHQGLSSPVTKSENRGEC | SPK002M A6 full length light chain |
| 63 | EVQLVESGGGLIQPGGSLRLSCAASIITVTSNYMSWVRQAPGKGL EWVSVIYPGGSTFYADSVKGRFTISYDNSKNTLYLQMNSLRAEDT AVYYCARDLVVYGMDVWGQGTTVTVSSASTKGPSVFPLAPSSKST SGGTAALGCLVKDYFPEPVTVSWNSGALTSGVHTFPAVLQSSGLY SLSSVVTVPSSSLGTQTYICNVNHKPSNTKVDKRVEPKSCDKTHT CPPCPAPELLGGPSVFLFPPKPKDTLMISRTPEVTCVVVDVSHED PEVKFNWYVDGVEVHNAKTKPREEQYNSTYRVVSVLTVLHQDWLN GKEYKCKVSNKALPAPIEKTISKAKGQPREPQVYTLPPSREEMTK NQVSLTCLVKGFYPSDIAVEWESNGQPENNYKTTPPVLDSDGSFF LYSKLTVDKSRWQQGNVFSCSVMHEALHNHYTQKSLSLSPGK | SPK002M B1 full length heavy chain |
| 64 | EIVLTQSPGTLSLSPGERATLSCRASQSVSDSYLAWYQQKPGQAP RLLIYGASSRATGIPGRFSGSGSGTDFTLTISRLEPEDFAIYYCQ YGVTFGGGTKVEIKRTVAAPSVFIFPPSDEQLKSGTASVVCLLNN FYPREAKVQWKVDNALQSGNSQESVTEQDSKDSTYSLSSTLTLSK ADYEKHKVYACEVTHQGLSSPVTKSENRGEC | SPK002M B1 full length light chain |
| 65 | EVQLVESGGGLIQPGGSLRLSCAASIITVTSNYMSWVRQAPGKGL EWVSVIYPGGSTFYADSVKGRFTISYDNSKNTLYLQMNSLRAEDT AVYYCARDLVVYGMDVWGQGTTVTVSSASTKGPSVFPLAPSSKST SGGTAALGCLVKDYFPEPVTVSWNSGALTSGVHTFPAVLQSSGLY SLSSVVTVPSSSLGTQTYICNVNHKPSNTKVDKRVEPKSCDKTHT CPPCPAPELLGGPSVFLFPPKPKDTLMISRTPEVTCVVVDVSHED PEVKFNWYVDGVEVHNAKTKPREEQYNSTYRVVSVLTVLHQDWLN GKEYKCKVSNKALPAPIEKTISKAKGQPREPQVYTLPPSREEMTK NQVSLTCLVKGFYPSDIAVEWESNGQPENNYKTTPPVLDSDGSFF LYSKLTVDKSRWQQGNVFSCSVMHEALHNHYTQKSLSLSPGK | SPK002M B2 full length heavy chain |
| 66 | EIVLTQSPGTLSLSPGERATLSCRASQSVSSSYLAWYQQKPGQAP RLLIYGASSRATGIPGRFSGSGSGTDFTLTISRLEPEDFAIYYCQ QGVTFGGGTKVEIKRTVAAPSVFIFPPSDEQLKSGTASVVCLLNN FYPREAKVQWKVDNALQSGNSQESVTEQDSKDSTYSLSSTLTLSK ADYEKHKVYACEVTHQGLSSPVTKSENRGEC | SPK002M B2 full length light chain |
| 67 | EVQLVESGGGLIQPGGSLRLSCAASIITVTSNYMSWVRQAPGKGL EWVSVAYPGGSTFYADSVKGRFTISTDNSKNTLYLQMNSLRAEDT AVYYCARDLVVYGMDVWGQGTTVTVSSASTKGPSVFPLAPSSKST SGGTAALGCLVKDYFPEPVTVSWNSGALTSGVHTFPAVLQSSGLY SLSSVVTVPSSSLGTQTYICNVNHKPSNTKVDKRVEPKSCDKTHT CPPCPAPELLGGPSVFLFPPKPKDTLMISRTPEVTCVVVDVSHED PEVKFNWYVDGVEVHNAKTKPREEQYNSTYRVVSVLTVLHQDWLN GKEYKCKVSNKALPAPIEKTISKAKGQPREPQVYTLPPSREEMTK NQVSLTCLVKGFYPSDIAVEWESNGQPENNYKTTPPVLDSDGSFF LYSKLTVDKSRWQQGNVFSCSVMHEALHNHYTQKSLSLSPGK | SPK002M C1 full length heavy chain |
| 68 | EIVLTQSPGTLSLSPGERATLSCRASQSVSDSYLAWYQQKPGQAP RLLIYGASSRATGIPGRESGSGSGTDFTLTISRLEPEDFAVYYCQ YGVTFGGGTKVEIKRTVAAPSVFIFPPSDEQLKSGTASVVCLLNN FYPREAKVQWKVDNALQSGNSQESVTEQDSKDSTYSLSSTLTLSK ADYEKHKVYACEVTHQGLSSPVTKSENRGEC | SPK002M C1 full length light chain |
| 69 | EVQLVESGGGLIQPGGSLRLSCAASIITVTSNYMSWVRQAPGKGL EWVSVAYPGGSTFYADSVKGRFTISTDNSKNTLYLQMNSLRAEDT AVYYCARDLVVYGMDVWGQGTTVTVSSASTKGPSVFPLAPSSKST SGGTAALGCLVKDYFPEPVTVSWNSGALTSGVHTFPAVLQSSGLY SLSSVVTVPSSSLGTQTYICNVNHKPSNTKVDKRVEPKSCDKTHT CPPCPAPELLGGPSVFLFPPKPKDTLMISRTPEVTCVVVDVSHED PEVKFNWYVDGVEVHNAKTKPREEQYNSTYRVVSVLTVLHQDWLN GKEYKCKVSNKALPAPIEKTISKAKGQPREPQVYTLPPSREEMTK NQVSLTCLVKGFYPSDIAVEWESNGQPENNYKTTPPVLDSDGSFF LYSKLTVDKSRWQQGNVFSCSVMHEALHNHYTQKSLSLSPGK | SPK002M C2 full length heavy chain |
| 70 | EIVLTQSPGTLSLSPGERATLSCRASQSVSSSYLAWYQQKPGQAP RLLIYGASSRATGIPGRFSGSGSGTDFTLTISRLEPEDFAVYYCQ QGVTFGGGTKVEIKRTVAAPSVFIFPPSDEQLKSGTASVVCLLNN | SPK002M C2 full length light chain |

| TABLE of sequences | | |
|---|---|---|
| SEQ ID NO. SPK002 MA1 | Sequence | Description |
| | FYPREAKVQWKVDNALQSGNSQESVTEQDSKDSTYSLSSTLTLSK ADYEKHKVYACEVTHQGLSSPVTKSENRGEC | |
| 71 | EVQLVESGGGLIQPGGSLRLSCAASIITVTSNYMSWVRQAPGKGL EWVSVIYPGGSTFYADSVKGRFTISTDNSKNTLYLQMNSLRAEDT AVYYCARDLVVYGMDVWGQGTTVTVSSASTKGPSVFPLAPSSKST SGGTAALGCLVKDYFPEPVTVSWNSGALTSGVHTFPAVLQSSGLY SLSSVVTVPSSSLGTQTYICNVNHKPSNTKVDKRVEPKSCDKTHT CPPCPAPELLGGPSVFLFPPKPKDTLMISRTPEVTCVVVDVSHED PEVKFNWYVDGVEVHNAKTKPREEQYNSTYRVVSVLTVLHQDWLN GKEYKCKVSNKALPAPIEKTISKAKGQPREPQVYTLPPSREEMTK NQVSLTCLVKGFYPSDIAVEWESNGQPENNYKTTPPVLDSDGSFF LYSKLTVDKSRWQQGNVFSCSVMHEALHNHYTQKSLSLSPGK | SPK002M C3 full length heavy chain |
| 72 | EIVLTQSPGTLSLSPGERATLSCRASQSVSSSYLAWYQQKPGQAP RLLIYGASSRATGIPGRFSGSGSGTDFTLTISRLEPEDFAVYYCQ QGVTFGGGTKVEIKRTVAAPSVFIFPPSDEQLKSGTASVVCLLNN FYPREAKVQWKVDNALQSGNSQESVTEQDSKDSTYSLSSTLTLSK ADYEKHKVYACEVTHQGLSSPVTKSENRGEC | SPK002M C3 full length light chain |
| 73 | EVQLVESGGGLIQPGGSLRLSCAASGITVTSNYMSWVRQAPGK GLEWVSVIYPGGSTFYADSVKGRFTISRDNSKNTLYLQMNSLR AEDTAVYYCARDLVVYGMDVWGQGTTVTVSS | SPK002 - Cv2.3194 Heavy chain variable domain |
| 74 | EIVLTQSPGTLSLSPGERATLSCRASQSVSSSYLAWY QQKPGQAPRLLIYGASSRATGIPGRFSGSGSGTDFTL TISRLEPEDFAIYYCQQGVTFGGGTKVEIK | SPK002 - Cv2.3194 Light chain variable domain |
| 75 | MFVFLVLLPLVSSQCVNLTTRTQLPPAYTNSFTRGVYYPDKVERS SVLHSTQDLFLPFFSNVTWFHAIHVSGTNGTKRFDNPVLPENDGV YFASTEKSNIIRGWIFGTTLDSKTQSLLIVNNATNVVIKVCEFQF CNDPFLGVYYHKNNKSWMESEFRVYSSANNCTFEYVSQPFLMDLE GKQGNFKNLREFVFKNIDGYFKIYSKHTPINLVRDLPQGFSALEP LVDLPIGINITRFQTLLALHRSYLTPGDSSSGWTAGAAAYYVGYL QPRTFLLKYNENGTITDAVDCALDPLSETKCTLKSFTVEKGIYQT SNFRVQPTESIVRFPNITNLCPFGEVFNATRFASVYAWNRKRISN CVADYSFLYNSASFSTFKCYGVSPTKLNDLCFTNVYADSFVIRGD EVRQIAPGQTGKIADYNYKLPDDFTGCVIAWNSNNLDSKVGGNYN YLYRLFRKSNLKPFERDISTEIYQAGSTPCNGVEGENCYFPLQSY GFQPTNGVGYQPYRVVVLSFELLHAPATVCGPKKSTNLVKNKCVN FNFNGLTGTGVLTESNKKFLPFQQFGRDIADTTDAVRDPQTLEIL DITPCSFGGVSVITPGTNTSNQVAVLYQDVNCTEVPVAIHADQLT PTWRVYSTGSNVFQTRAGCLIGAEHVNNSYECDIPIGAGICASYQ TQTNSPRRARSVASQSIIAYTMSLGAENSVAYSNNSIAIPTNFTI SVTTEILPVSMTKTSVDCTMYICGDSTECSNLLLQYGSFCTQLNR ALTGIAVEQDKNTQEVFAQVKQIYKTPPIKDFGGFNFSQILPDPS KPSKRSFIEDLLFNKVTLADAGFIKQYGDCLGDIAARDLICAQKF NGLTVLPPLLTDEMIAQYTSALLAGTITSGWTFGAGAALQIPFAM QMAYRENGIGVTQNVLYENQKLIANQFNSAIGKIQDSLSSTASAL GKLQDVVNQNAQALNTLVKQLSSNFGAISSVLNDILSRLDPPEAE VQIDRLITGRLQSLQTYVTQQLIRAAEIRASANLAATKMSECVLG QSKRVDFCGKGYHLMSFPQSAPHGVVFLHVTYVPAQEKNFTTAPA ICHDGKAHFPREGVFVSNGTHWFVTQRNFYEPQIITTDNTFVSGN CDVVIGIVNNTVYDPLQPELDSFKEELDKYFKNHTSPDVDLGDIS GINASVVNIQKEIDRLNEVAKNLNESLIDLQELGKYEQGSGYIPE APRDGQAYVRKDGEWVLLSTFLGGSHHHHHHHSAWSHPQFEKGT GGLNDIFEAQKIEWHE | SARS-CoV-2 Spike ectodomain (tri-S) |
| 76 | MGWSCIILFLVATATGVHSVNLTTRTQLPPAYTNSFTRGVYYPDK VFRSSVLHSTQDLFLPFFSNVTWFHAIHVSGTNGTKRFDNPVLPF NDGVYFASTEKSNIIRGWIFGTTLDSKTQSLLIVNNATNVVIKVC EFQFCNDPFLGVYYHKNNKSWMESEFRVYSSANNCTFEYVSQPFL MDLEGKQGNFKNLREFVFKNIDGYFKIYSKHTPINLVRDLPQGFS ALEPLVDLPIGINITRFQTLLALHRSYLTPGDSSSGWTAGAAAYY VGYLQPRTFLLKYNENGTITDAVDCALDPLSETKCTLKSFTVEKG IYQTSNFRVQPTESIVRFPNITNLCPFGEVFNATRFASVYAWNRK RISNCVADYSFLYNSASFSTFKCYGVSPTKLNDLCFTNVYADSFV IRGDEVRQIAPGQTGKIADYNYKLPDDFTGCVIAWNSNNLDSKVG GNYNYLYRLFRKSNLKPFERDISTEIYQAGSTPCNGVEGENCYFP LQSYGFQPTNGVGYQPYRVVVLSFELLHAPATVCGPKKSTNLVKN KCVNFNFNGLTGTGVLTESNKKFLPFQQFGRDIADTTDAVRDPQT LEILDITPCSFGGVSVITPGTNTSNQVAVLYQDVNCTEVPVAIHA | SARS-CoV-2 S1 domain |

-continued

TABLE of sequences

| SED ID NO. SPK002 MA1 | Sequence | Description |
|---|---|---|
| | DQLTPTWRVYSTGSNVFQTRAGCLIGAEHVNNSYECDIPIGAGIC ASYQTQTNSPGGSHHHHHHHH | |
| 77 | METDTLLLWVLLLWVPGSTGNITNLCPFGEVENATRFASVYAWNR KRISNCVADYSFLYNSASFSTFKCYGVSPTKLNDLCFTNVYADSF VIRGDEVRQIAPGQTGKIADYNYKLPDDFTGCVIAWNSNNLDSKV GGNYNYLYRLFRKSNLKPFERDISTEIYQAGSTPCNGVEGENCYF PLQSYGFQPTNGVGYQPYRVVVLSFELLHAPATVCGPKGSGLVPR GSHHHHHHHHSAWSHPQFEKGTGGLNDIFEAQKIEWHE | SARS-CoV-2 RBD domain |
| 78 | METDTLLLWVLLLWVPGSTGNITNLCPFGEVENATRFASVYAWNR KRISNCVADYSFLYNSASFSTFKCYGVSPTKLNDLCFTNVYADSF VIRGDEVRQIAPGQTGKIADYNYKLPDDFTGCVIAWNSNNLDSKV GGNYNYLYRLFRKSNLKPFERDISTEIYQAGSTPCNGVEGENCYF PLQSYGFQPTNGVGYQPYRVVVLSFELLHAPATVCGPKGSGLVPR GSHHHHHHHHSAWSHPQFEKGTGGLNDIFEAQKIEWHE | RBD Wuhan |
| 79 | METDTLLLWVLLLWVPGSTGNITNLCPFGEVENATRFASVYAWNR KRISNCVADYSFLYNSASFSTFKCYGVSPTKLNDLCFTNVYADSF VIRGDEVRQIAPGQTGKIADYNYKLPDDFTGCVIAWNSNNLDSKV GGNYNYRYRLFRKSNLKPFERDISTEIYQAGSKPCNGVEGENCYF PLQSYGFQPTNGVGYQPYRVVVLSFELLHAPATVCGPKGSGLVPR GSHHHHHHHHSAWSHPQFEKGTGGLNDIFEAQKIEWHE | RBD Delta variant |
| 80 | METDTLLLWVLLLWVPGSTGNITNLCPFDEVENATRFASVYAWNR KRISNCVADYSVLYNFAPFFAFKCYGVSPTKLNDLCFTNVYADSF VIRGNEVSQIAPGQTGNIADYNYKLPDDFTGCVIAWNSNKLDSKV GGNYNYLYRLFRKSNLKPFERDISTEIYQAGNKPCNGVAGENCYF PLRSYGFRPTYGVGHQPYRVVVLSFELLHAPATVCGPKGSGLVPR GSHHHHHHHHSAWSHPQFEKGTGGLNDIFEAQKIEWHE | RBD BA.2. variant |
| 81 | METDTLLLWVLLLWVPGSTGNITNLCPFHEVENATTFASVYAWNR KRISNCVADYSVLYNFAPFFAFKCYGVSPTKLNDLCFTNVYADSF VIRGNEVSQIAPGQTGNIADYNYKLPDDFTGCVIAWNSNKLDSKV SGNYNYLYRLFRKSKLKPFERDISTEIYQAGNKPCNGVAGSNCYF PLQSYGFRPTYGVGHQPYRVVVLSFELLHAPATVCGPKGSGLVPR GSHHHHHHHHSAWSHPQFEKGTGGLNDIFEAQKIEWHE | RBD BA.2.75.2 variant |
| 82 | METDTLLLWVLLLWVPGSTGNITNLCPFDEVENATRFASVYAWNR KRISNCVADYSFLYNFAPFFAFKCYGVSPTKLNDLCFTNVYADSF VIRGNEVSQIAPGQTGNIADYNYKLPDDFTGCVIAWNSNKLDSKV GGNYNYRYRLFRKSNLKPFERDISTEIYQAGNKPCNGVAGVNCYF PLQSYGFRPTYGVGHQPYRVVVLSFELLHAPATVCGPKGSGLVPR GSHHHHHHHHSAWSHPQFEKGTGGLNDIFEAQKIEWHE | RBD BA.4/5 variant |
| 83 | METDTLLLWVLLLWVPGSTGNITNLCPFDEVENATTFASVYAWNR KRISNCVADYSFLYNFAPFFAFKCYGVSPTKLNDLCFTNVYADSF VIRGNEVSQIAPGQTGNIADYNYKLPDDFTGCVIAWNSNKLDSTV GGNYNYRYRLFRKSKLKPFERDISTEIYQAGNKPCNGVAGVNCYF PLQSYGFRPTYGVGHQPYRVVVLSFELLHAPATVCGPKGSGLVPR GSHHHHHHHHSAWSHPQFEKGTGGLNDIFEAQKIEWHE | RBD BQ.1.1. variant |
| 84 | METDTLLLWVLLLWVPGSTGNITNLCPFHEVENATTFASVYAWNR KRISNCVADYSVIYNFAPFFAFKCYGVSPTKLNDLCFTNVYADSF VIRGNEVSQIAPGQTGNIADYNYKLPDDFTGCVIAWNSNKLDSKP SGNYNYLYRLFRKSKLKPFERDISTEIYQAGNKPCNGVAGPNCYS PLQSYGFRPTYGVGHQPYRVVVLSFELLHAPATVCGPKGSGLVPR GSHHHHHHHHSAWSHPQFEKGTGGLNDIFEAQKIEWHE | RBD XBB.1.5 variant |
| 85 | METDTLLLWVLLLWVPGSTGNITNLCPFHEVENATTFASVYAWNR KRISNCVADYSVIYNFAPFFAFKCYGVSPTKLNDLCFTNVYADSF VIRGNEVSQIAPGQTGNIADYNYKLPDDFTGCVIAWNSNKLDSKP SGNYNYLYRLFRKSKLKPFERDISTEIYQAGNRPCNGVAGPNCYS PLQSYGFRPTYGVGHQPYRVVVLSFELLHAPATVCGPKGSGLVPR GSHHHHHHHHSAWSHPQFEKGTGGLNDIFEAQKIEWHE | RBD XBB.1.16 variant |
| 86 | METDTLLLWVLLLWVPGSTGNITNLCPFHEVENATTFASVYAWNR KRISNCVADYSVIYNFAPFFAFKCYGVSPTKLNDLCFTNVYADSF VIRGNEVSQIAPGQTGNIADYNYKLPDDFTGCVIAWNSNKLDSKP SGNYNYLYRLLRKSKLKPFERDISTEIYQAGNKPCNGVAGPNCYS PLQSYGFRPTYGVGHQPYRVVVLSFELLHAPATVCGPKGSGLVPR GSHHHHHHHHSAWSHPQFEKGTGGLNDIFEAQKIEWHE | RBD EG.5.1 variant |

TABLE of sequences

| SEQ ID NO. SPK002 MA1 | Sequence | Description |
|---|---|---|
| 87 | METDTLLLWVLLLWVPGSTGNVTNLCPFHEVENATRFASVYAWNR TRISNCVADYSVLYNFAPFFAFKCYGVSPTKLNDLCFTNVYADSF VIKGNEVSQIAPGQTGNIADYNYKLPDDFTGCVIAWNSNKLDSKH SGNYDYWYRLFRKSKLKPFERDISTEIYQAGNKPCKGKGPNCYFP LQSYGFRPTYGVGHQPYRVVVLSFELLHAPATVCGPKGSGLVPRG SHHHHHHHHSAWSHPQFEKGTGGLNDIFEAQKIEWHE | RBD BA.2.86 variant |
| 88 | METDTLLLWVLLLWVPGSTGNVTNLCPFHEVENATRFASVYAWNR TRISNCVADYSVLYNFAPFFAFKCYGVSPTKLNDLCFTNVYADSF VIKGNEVSQIAPGQTGNIADYNYKLPDDFTGCVIAWNSNKLDSKH SGNYDYWYRSFRKSKLKPFERDISTEIYQAGNKPCKGKGPNCYFP LQSYGFRPTYGVGHQPYRVVVLSFELLHAPATVCGPKGSGLVPRG SHHHHHHHHSAWSHPQFEKGTGGLNDIFEAQKIEWHE | RBD JN-1 variant |
| 89 | METDTLLLWVLLLWVPGSTGSTIEEQAKTFLDKFNHEAEDLFYQS SLASWNYNTNITEENVQNMNNAGDKWSAFLKEQSTLAQMYPLQEI QNLTVKLQLQALQQNGSSVLSEDKSKRLNTILNTMSTIYSTGKVC NPDNPQECLLLEPGLNEIMANSLDYNERLWAWESWRSEVGKQLRP LYEEYVVLKNEMARANHYEDYGDYWRGDYEVNGVDGYDYSRGQLI EDVEHTFEEIKPLYEHLHAYVRAKLMNAYPSYISPIGCLPAHLLG DMWGRFWTNLYSLTVPFGQKPNIDVTDAMVDQAWDAQRIFKEAEK FFVSVGLPNMTQGFWENSMLTDPGNVQKAVCHPTAWDLGKGDFRI LMCTKVTMDDFLTAHHEMGHIQYDMAYAAQPFLLRNGANEGFHEA VGEIMSLSAATPKHLKSIGLLSPDFQEDNETEINFLLKQALTIVG TLPFTYMLEKWRWMVFKGEIPKDQWMKKWWEMKREIVGVVEPVPH DETYCDPASLFHVSNDYSFIRYYTRTLYQFQFQEALCQAAKHEGP LHKCDISNSTEAGQKLENMLRLGKSEPWTLALENVVGAKNMNVRP LLNYFEPLFTWLKDQNKNSFVGWSTDWSPYADGSGLVPRGSHHHH HHHHSAWSHPQFEK | ACE2 ectodomain |
| 90 | EVQLVESGGGLVKPGGSLRLSCAASGFTFSSYYMNWVRQAPGKGL EWVSSISEDGSYTYYPDSLKGRFTISRDSAKNSLYLQMNSLRADD TAVYYCARDFSGHTAWAGTGFEYWGQGTLVTVSS | Adintrevimab VH |
| 91 | QSVLTQPPSVSGAPGQRITISCTGSSSNIGAGYDVHWYQQLPGTA PKLLIYGSSSRNSGVPDRESGSKSGTSASLAITGLQAEDEADYYC QSYDSSLSVLYTFGTGTKVTVL | Adinvetrimab VL |
| 92 | EVQLVESGGGLVKPGGSLRLSCAASGFTFRDVWMSWVRQAPGKGL EWVGRIKSKIDGGTTDYAAPVKGRFTISRDDSKNTLYLQMNSLKT EDTAVYYCTTAGSYYYDTVGPGLPEGKFDYWGQGTLVTVSS | Cilgavimab VH |
| 93 | DIVMTQSPDSLAVSLGERATINCKSSQSVLYSSNNKNYLAWYQQK PGQPPKLLMYWASTRESGVPDRFSGSGSGAEFTLTISSLQAEDVA IYYCQQYYSTLTFGGGTKVEIK | Cilgavimab VL |
| 94 | QVQLVESGGGVVQPGRSLRLSCAASGFTFSNYAMYWVRQAPGKGL EWVAVISYDGSNKYYADSVKGRFTISRDNSKNTLYLQMNSLRTED TAVYYCASGSDYGDYLLVYWGQGTLVTVSS | Imdevimab VH |
| 95 | QSALTQPASVSGSPGQSITISCTGTSSDVGGYNYVSWYQQHPGKA PKLMIYDVSKRPSGVSNRFSGSKSGNTASLTISGLQSEDEADYYC NSLTSISTWVFGGGTKLTVL | Indevimab VL |
| 96 | QVQLVQSGAEVKKPGASVKVSCKASGYPFTSYGISWVRQAPGQGL EWMGWISTYQGNTNYAQKFQGRVTMTTDTSTTTGYMELRRLRSDD TAVYYCARDYTRGAWFGESLIGGFDNWGQGTLVTVSS | Sotrovimab VH |

-continued

| TABLE of sequences | | |
|---|---|---|
| SED ID NO. SPK002 MA1 | Sequence | Description |
| 97 | EIVLTQSPGTLSLSPGERATLSCRASQTVSSTSLAWYQQKPGQAP RLLIYGASSRATGIPDRESGSGSGTDFTLTISRLEPEDFAVYYCQ QHDTSLTFGGGTKVEIK | Sotrovimab VL |

In case of any discrepancy between the above list of sequences and sequences disclosed in an appended sequence listing (e.g. according to the WIPO Standard ST.26), the correct sequences are those disclosed in the above table included in the present disclosure.

We claim:

1. An antibody of any isotype or species that binds to the viral Spike protein receptor binding-domain (RBD) of Severe Acute Respiratory Syndrome-related Coronavirus 2 (SARS-CoV-2), or antigen-binding fragment thereof, comprising:
   (i) a heavy chain variable domain, or fragment thereof, comprising:
  - a HCDR1 of SEQ ID NO. 1,
  - a HCDR2 selected from SEQ ID NO. 2 and SEQ ID NO. 20, and
  - a HCDR3 of SEQ ID NO. 3, and
- (ii) a light chain variable domain, or fragment thereof, comprising:
  - a LCDR1 selected from SEQ ID NO. 9, SEQ ID NO. 23, SEQ ID NO. 24 and SEQ ID NO. 25,
  - a LCDR2 of SEQ ID NO. 10, and
  - a LCDR3 selected from SEQ ID NO. 11 and SEQ ID NO. 27, and
- (iii) a HFR3 of the amino acid sequence RFTISXDNSKNTLYLQMNSLRAEDTAVYYCAR (SEQ ID NO. 28) wherein X means an amino acid selected from Alanine, Tyrosine and Threonine.

2. The antibody or antigen-binding fragment thereof according to claim 1, wherein HFR3 is selected from SEQ ID NO. 6, SEQ ID NO. 21, and SEQ ID NO. 22.

3. The antibody or antigen-binding fragment thereof according to claim 1, which is selected from:

an antibody comprising:
- (i) a heavy chain variable domain, or fragment thereof, comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 6, and
- (ii) a light chain variable domain, or fragment thereof, comprising (a) a LCDR1 of SEQ ID NO. 9, (b) a LCDR2 of SEQ ID NO. 10 and (c) a LCDR3 of SEQ ID NO. 11, an antibody comprising:
- (i) a heavy chain variable domain, or fragment thereof, comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 6, and
- (ii) a light chain variable domain, or fragment thereof, comprising (a) a LCDR1 of SEQ ID NO. 23, (b) a LCDR2 of SEQ ID NO. 10 and (c) a LCDR3 of SEQ ID NO. 11, an antibody comprising:
- (i) a heavy chain variable domain, or fragment thereof, comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 6, and
- (ii) a light chain variable domain, or fragment thereof, comprising (a) a LCDR1 of SEQ ID NO. 24, (b) a LCDR2 of SEQ ID NO. 10 and (c) a LCDR3 of SEQ ID NO. 11, an antibody comprising:
- (i) a heavy chain variable domain, or fragment thereof, comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 21, and
- (ii) a light chain variable domain, or fragment thereof, comprising (a) a LCDR1 of SEQ ID NO. 25, (b) a LCDR2 of SEQ ID NO. 10 and (c) a LCDR3 of SEQ ID NO. 27, an antibody comprising:
- (i) a heavy chain variable domain, or fragment thereof, comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 21, and
- (ii) a light chain variable domain, or fragment thereof, comprising (a) a LCDR1 of SEQ ID NO. 24, (b) a LCDR2 of SEQ ID NO. 10 and (c) a LCDR3 of SEQ ID NO. 11, an antibody comprising:
- (i) a heavy chain variable domain, or fragment thereof, comprising (a) a HCDR1 of SEQ ID NO. 1, (b) a HCDR2 of SEQ ID NO. 20, (c) a HCDR3 of SEQ ID NO. 3 and (d) a HFR3 of SEQ ID NO. 22, and
- (ii) a light chain variable domain, or fragment thereof, comprising (a) a LCDR1 of SEQ ID NO. 25, (b) a LCDR2 of SEQ ID NO. 10 and (c) a LCDR3 of SEQ ID NO. 27, an antibody comprising:
- (i) a heavy chain variable domain, or fragment thereof, comprising (a) a HCDR1 of SEQ ID NO. 1, (b) a HCDR2 of SEQ ID NO. 20, (c) a HCDR3 of SEQ ID NO. 3 and (d) a HFR3 of SEQ ID NO. 22, and
- (ii) a light chain variable domain, or fragment thereof, comprising (a) a LCDR1 of SEQ ID NO. 24, (b) a LCDR2 of SEQ ID NO. 10 and (c) a LCDR3 of SEQ ID NO. 11, and an antibody comprising:
- (i) a heavy chain variable domain, or fragment thereof, comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 22, and
- (ii) a light chain variable domain, or fragment thereof, comprising (a) a LCDR1 of SEQ ID NO. 24, (b) a LCDR2 of SEQ ID NO. 10 and (c) a LCDR3 of SEQ ID NO. 11, or antigen-binding fragment of the selected antibody.

4. The antibody or antigen-binding fragment thereof according to claim 1, which is selected from:
- an antibody comprising (i) a heavy chain variable domain of SEQ ID NO. 8 and comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 6 and a light chain variable domain of SEQ ID NO. 16 and comprising (a) a LCDR1 of SEQ ID NO. 9, (b) a LCDR2 of SEQ ID NO. 10 and (c) a LCDR3 of SEQ ID NO. 11,
- an antibody comprising (i) a heavy chain variable domain of SEQ ID NO. 29 and comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 6, and (ii) a light chain variable domain of SEQ ID NO. 30 and comprising (a) a LCDR1 of SEQ ID NO. 23, (b) a LCDR2 of SEQ ID NO. 10 and (c) a LCDR3 of SEQ ID NO. 11,
- an antibody comprising (i) a heavy chain variable domain of SEQ ID NO. 31 and comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 6 and (ii) a light chain variable domain of SEQ ID NO. 32 and comprising (a) a LCDR1 of SEQ ID NO. 24, (b) a LCDR2 of SEQ ID NO. 10 and (c) a LCDR3 of SEQ ID NO. 11,
- an antibody comprising (i) a heavy chain variable domain of SEQ ID NO. 33 and comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 6, and (ii) a light chain variable domain of SEQ ID NO. 34 and comprising (a) a LCDR1 of SEQ ID NO. 24, (b) a LCDR2 of SEQ ID NO. 10 and (c) a LCDR3 of SEQ ID NO. 11,
- an antibody comprising (i) a heavy chain variable domain of SEQ ID NO. 35 and comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 6, and (ii) a light chain variable domain of SEQ ID NO. 36 and comprising (a) a LCDR1 of SEQ ID NO. 24, (b) a LCDR2 of SEQ ID NO. 10 and (c) a LCDR3 of SEQ ID NO. 11,
- an antibody comprising (i) a heavy chain variable domain of SEQ ID NO. 37 and comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 6, and (ii) a light chain variable domain of SEQ ID NO. 38 and comprising (a) a LCDR1 of SEQ ID NO. 24, (b) a LCDR2 of SEQ ID NO. 10 and (c) a LCDR3 of SEQ ID NO. 11,
- an antibody comprising (i) a heavy chain variable domain of SEQ ID NO 39 and comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 21, and (ii) a light chain variable domain of SEQ ID NO. 40 and comprising (a) a LCDR1 of SEQ ID NO. 25, (b) a LCDR2 of SEQ ID NO. 10 and (c) a LCDR3 of SEQ ID NO. 27,
- an antibody comprising (i) a heavy chain variable domain of SEQ ID NO 41 and comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 21, and (ii) a light chain variable domain of SEQ ID NO. 42 and comprising (a) a LCDR1 of SEQ ID NO. 24, (b) a LCDR2 of SEQ ID NO. 10 and (c) a LCDR3 of SEQ ID NO. 11,
- an antibody comprising (i) a heavy chain variable domain of SEQ ID NO 43 and comprising (a) a HCDR1 of SEQ ID NO. 1, (b) a HCDR2 of SEQ ID NO. 20, (c) a HCDR3 of SEQ ID NO. 3 and (d) a HFR3 of SEQ ID NO. 22, and (ii) a light chain variable domain of SEQ ID NO. 44 and comprising (a) a LCDR1 of SEQ ID NO. 25, (b) a LCDR2 of SEQ ID NO. 10 and (c) a LCDR3 of SEQ ID NO. 27,
- an antibody comprising (i) a heavy chain variable domain of SEQ ID NO 45 and comprising (a) a HCDR1 of SEQ ID NO. 1, (b) a HCDR2 of SEQ ID NO. 20, (c) a HCDR3 of SEQ ID NO. 3 and (d) a HFR3 of SEQ ID NO. 22, and (ii) a light chain variable domain of SEQ ID NO. 46 and comprising (a) a LCDR1 of SEQ ID NO. 24, (b) a LCDR2 of SEQ ID NO. 10 and (c) a LCDR3 of SEQ ID NO. 11, and
- an antibody comprising (i) a heavy chain variable domain of SEQ ID NO 47 and comprising (a) a HCDR1 of SEQ ID NO. 1, (b) a HCDR2 of SEQ ID NO. 2, (c) a HCDR3 of SEQ ID NO. 3 and (d) a HFR3 of SEQ ID NO. 22, and (ii) a light chain variable domain of SEQ ID NO. 48 and comprising (a) a LCDR1 of SEQ ID NO. 24, (b) a LCDR2 of SEQ ID NO. 10 and (c) a LCDR3 of SEQ ID NO. 11, or antigen-binding fragment of the selected antibody.

5. The antibody or antigen-binding fragment thereof according to claim 1, which is selected from:
- an antibody comprising (i) a heavy chain variable domain of SEQ ID NO. 8 and (ii) a light chain variable domain of SEQ ID NO. 16,
- an antibody comprising (i) a heavy chain variable domain of SEQ ID NO. 29 and (ii) a light chain variable domain of SEQ ID NO. 30,
- an antibody comprising (i) a heavy chain variable domain of SEQ ID NO. 31 and (ii) a light chain variable domain of SEQ ID NO. 32,
- an antibody comprising (i) a heavy chain variable domain of SEQ ID NO. 33 and (ii) a light chain variable domain of SEQ ID NO. 34,
- an antibody comprising (i) a heavy chain variable domain of SEQ ID NO. 35 and (ii) a light chain variable domain of SEQ ID NO. 36,
- an antibody comprising (i) a heavy chain variable domain of SEQ ID NO. 37 and (ii) a light chain variable domain of SEQ ID NO. 38,
- an antibody comprising (i) a heavy chain variable domain of SEQ ID NO. 39 and (ii) a light chain variable domain of SEQ ID NO. 40,
- an antibody comprising (i) a heavy chain variable domain of SEQ ID NO. 41 and (ii) a light chain variable domain of SEQ ID NO. 42,
- an antibody comprising (i) a heavy chain variable domain of SEQ ID NO. 43 and (ii) a light chain variable domain of SEQ ID NO. 44
- an antibody comprising (i) a heavy chain variable domain of SEQ ID NO. 45 and (ii) a light chain variable domain of SEQ ID NO. 46,
- an antibody comprising (i) a heavy chain variable domain of SEQ ID NO. 47 and (ii) a light chain variable domain of SEQ ID NO. 48, or antigen-binding fragment of the selected antibody.

6. The antibody or antigen-binding fragment thereof according to claim 1, wherein said heavy chain variable domain is associated with IgG.

7. The antibody according to claim 1, which is a recombinant human monoclonal antibody of IgG1 or IgA isotype.

8. The antibody or antigen-binding fragment thereof according to claim 1, which binds to recombinant SARS-CoV-2 RBD domain of the Spike protein from the (i) Wuhan variant of SEQ ID NO. 78, (ii) Delta variant of SEQ ID NO. 79, (iii) BA.2 variant of SEQ ID NO. 80, (iv) BA.2.75.2 variant of SEQ ID NO. 81, (v) BA 4/5 variant of SEQ ID NO. 82, (vi) BQ.1.1. variant of SEQ ID NO. 83, (vii) XBB.1.5. variant of SEQ ID NO. 84, (viii) XBB.1.16 variant of SEQ ID NO. 85, (ix) EG.5 variant of SEQ ID NO. 86, (x) BA.2.86 variant of SEQ ID NO. 87 and (xi) JN-1 variant of SEQ ID NO. 88.

9. The antibody or antigen-binding fragment thereof according to claim 1, which neutralizes at least one SARS-CoV-2 selected from the isolates D614G, XBB.1.5, XBB.1.16, EG.5.1 and JN-1.

10. The antibody or antigen-binding fragment thereof according to claim 1, which is produced recombinantly and comprises a non-native human glycosylation pattern and/or a non-human glycosylation pattern.

11. The antibody or antigen-binding fragment thereof according to claim 1, which further comprises a detectable label.

12. A nucleic acid encoding the antibody or antigen-binding fragment thereof of claim 1.

13. An expression vector for the recombinant production of an antibody or antigen-binding fragment comprising at least one nucleic acid according to claim 12.

14. A host cell comprising the expression vector according to claim 13.

15. A method of production of an antibody or antigen-binding fragment comprising: (i) culturing the host cell of claim 14 for expression of said antibody or antigen-binding fragment by the host cell; (ii) recovering said antibody or antigen-binding fragment; and (iii) purifying said antibody or antigen-binding fragment.

16. A pharmaceutical composition, comprising the antibody or antigen-binding fragment thereof according to claim 1 and at least one of a pharmaceutically acceptable carrier, an adjuvant, and a preservative.

17. A pharmaceutical composition comprising: (a) an antibody or antigen-binding fragment thereof according to claim 1; and (b) an antibody selected from the group of the following reference antibodies: (i) antibodies directed against RBD selected from Adintrevimab, VYD222 antibody, SA55 antibody, Cilgavimab, Imdevimab, and Sotrovimab, (ii) anti-S2 antibodies directed against the fusion peptide selected from C77G12 antibody, 76E1 antibody and COV4462 antibody, (iii) antibodies directed against the HR2 region and (iv) antibodies directed against the S2 stem helix.

18. A method for the detection of a SARS-CoV-2 in a sample comprising: contacting said sample with an antibody or antigen-binding fragment thereof according to claim 1, and detecting the antigen-antibody complexes formed, thereby detecting the presence, absence or level of SARS-CoV-2 in the sample.

19. A method comprising administering the antibody or antigen-binding fragment thereof according to claim 1 to a subject.

20. A medical device, comprising an antibody or antigen-binding fragment thereof according to claim 1 for administration by injection or inhalation.

21. The pharmaceutical composition according to claim 17, wherein the antibody directed against the HR2 region is Cv2.3132.

* * * * *

SEQUENCE LISTING

```
Sequence total quantity: 97
SEQ ID NO: 1              moltype = AA  length = 5
FEATURE                   Location/Qualifiers
source                    1..5
                          mol_type = protein
                          organism = synthetic construct
SEQUENCE: 1
SNYMS                                                                   5

SEQ ID NO: 2              moltype = AA  length = 16
FEATURE                   Location/Qualifiers
source                    1..16
                          mol_type = protein
                          organism = synthetic construct
SEQUENCE: 2
VIYPGGSTFY ADSVKG                                                       16

SEQ ID NO: 3              moltype = AA  length = 9
FEATURE                   Location/Qualifiers
source                    1..9
                          mol_type = protein
                          organism = synthetic construct
SEQUENCE: 3
DLVVYGMDV                                                               9

SEQ ID NO: 4              moltype = AA  length = 30
FEATURE                   Location/Qualifiers
source                    1..30
                          mol_type = protein
                          organism = synthetic construct
SEQUENCE: 4
EVQLVESGGG LIQPGGSLRL SCAASTITVT                                        30

SEQ ID NO: 5              moltype = AA  length = 14
FEATURE                   Location/Qualifiers
source                    1..14
                          mol_type = protein
                          organism = synthetic construct
SEQUENCE: 5
WVRQAPGKGL EWVS                                                         14

SEQ ID NO: 6              moltype = AA  length = 32
FEATURE                   Location/Qualifiers
source                    1..32
                          mol_type = protein
                          organism = synthetic construct
SEQUENCE: 6
RFTISADNSK NTLYLQMNSL RAEDTAVYYC AR                                     32

SEQ ID NO: 7              moltype = AA  length = 11
FEATURE                   Location/Qualifiers
source                    1..11
                          mol_type = protein
                          organism = synthetic construct
SEQUENCE: 7
WGQGTTVTVS S                                                            11
```

```
SEQ ID NO: 8              moltype = AA   length = 117
FEATURE                   Location/Qualifiers
source                    1..117
                          mol_type = protein
                          organism = synthetic construct
SEQUENCE: 8
EVQLVESGGG LIQPGGSLRL SCAASTITVT SNYMSWVRQA PGKGLEWVSV IYPGGSTFYA   60
DSVKGRFTIS ADNSKNTLYL QMNSLRAEDT AVYYCARDLV VYGMDVWGQG TTVTVSS    117

SEQ ID NO: 9              moltype = AA   length = 12
FEATURE                   Location/Qualifiers
source                    1..12
                          mol_type = protein
                          organism = synthetic construct
SEQUENCE: 9
RASQGFSSSY LA                                                      12

SEQ ID NO: 10             moltype = AA   length = 7
FEATURE                   Location/Qualifiers
source                    1..7
                          mol_type = protein
                          organism = synthetic construct
SEQUENCE: 10
GASSRAT                                                             7

SEQ ID NO: 11             moltype = AA   length = 5
FEATURE                   Location/Qualifiers
source                    1..5
                          mol_type = protein
                          organism = synthetic construct
SEQUENCE: 11
QQGVT                                                               5

SEQ ID NO: 12             moltype = AA   length = 23
FEATURE                   Location/Qualifiers
source                    1..23
                          mol_type = protein
                          organism = synthetic construct
SEQUENCE: 12
EIVLTQSPGT LSLSPGERAT LSC                                          23

SEQ ID NO: 13             moltype = AA   length = 15
FEATURE                   Location/Qualifiers
source                    1..15
                          mol_type = protein
                          organism = synthetic construct
SEQUENCE: 13
WYQQKPGQAP RLLIY                                                   15

SEQ ID NO: 14             moltype = AA   length = 32
FEATURE                   Location/Qualifiers
source                    1..32
                          mol_type = protein
                          organism = synthetic construct
SEQUENCE: 14
GIPGRFSGSG SGTDFTLTIS RLEPEDFAVY YC                                32

SEQ ID NO: 15             moltype = AA   length = 10
FEATURE                   Location/Qualifiers
source                    1..10
                          mol_type = protein
                          organism = synthetic construct
SEQUENCE: 15
FGGGTKVEIK                                                         10

SEQ ID NO: 16             moltype = AA   length = 104
FEATURE                   Location/Qualifiers
source                    1..104
                          mol_type = protein
                          organism = synthetic construct
SEQUENCE: 16
EIVLTQSPGT LSLSPGERAT LSCRASQGFS SSYLAWYQQK PGQAPRLLIY GASSRATGIP   60
GRFSGSGSGT DFTLTISRLE PEDFAVYYCQ QGVTFGGGTK VEIK                  104

SEQ ID NO: 17             moltype = AA   length = 30
FEATURE                   Location/Qualifiers
source                    1..30
                          mol_type = protein
```

```
                        organism = synthetic construct
SEQUENCE: 17
EVQLVESGGG LIQPGGSLRL SCAASVITVT                                        30

SEQ ID NO: 18           moltype = AA   length = 30
FEATURE                 Location/Qualifiers
source                  1..30
                        mol_type = protein
                        organism = synthetic construct
SEQUENCE: 18
EVQLVESGGG LIQPGGSLRL SCAASGITVT                                        30

SEQ ID NO: 19           moltype = AA   length = 30
FEATURE                 Location/Qualifiers
source                  1..30
                        mol_type = protein
                        organism = synthetic construct
SEQUENCE: 19
EVQLVESGGG LIQPGGSLRL SCAASIITVT                                        30

SEQ ID NO: 20           moltype = AA   length = 16
FEATURE                 Location/Qualifiers
source                  1..16
                        mol_type = protein
                        organism = synthetic construct
SEQUENCE: 20
VAYPGGSTFY ADSVKG                                                       16

SEQ ID NO: 21           moltype = AA   length = 32
FEATURE                 Location/Qualifiers
source                  1..32
                        mol_type = protein
                        organism = synthetic construct
SEQUENCE: 21
RFTISYDNSK NTLYLQMNSL RAEDTAVYYC AR                                     32

SEQ ID NO: 22           moltype = AA   length = 32
FEATURE                 Location/Qualifiers
source                  1..32
                        mol_type = protein
                        organism = synthetic construct
SEQUENCE: 22
RFTISTDNSK NTLYLQMNSL RAEDTAVYYC AR                                     32

SEQ ID NO: 23           moltype = AA   length = 12
FEATURE                 Location/Qualifiers
source                  1..12
                        mol_type = protein
                        organism = synthetic construct
SEQUENCE: 23
RASQGVSSSY LA                                                           12

SEQ ID NO: 24           moltype = AA   length = 12
FEATURE                 Location/Qualifiers
source                  1..12
                        mol_type = protein
                        organism = synthetic construct
SEQUENCE: 24
RASQSVSSSY LA                                                           12

SEQ ID NO: 25           moltype = AA   length = 12
FEATURE                 Location/Qualifiers
source                  1..12
                        mol_type = protein
                        organism = synthetic construct
SEQUENCE: 25
RASQSVSDSY LA                                                           12

SEQ ID NO: 26           moltype = AA   length = 32
FEATURE                 Location/Qualifiers
source                  1..32
                        mol_type = protein
                        organism = synthetic construct
SEQUENCE: 26
GIPGRFSGSG SGTDFTLTIS RLEPEDFAIY YC                                     32

SEQ ID NO: 27           moltype = AA   length = 6
FEATURE                 Location/Qualifiers
source                  1..6
```

```
                              mol_type = protein
                              organism = synthetic construct
SEQUENCE: 27
QYGVTF                                                                       6

SEQ ID NO: 28            moltype = AA   length = 32
FEATURE                  Location/Qualifiers
source                   1..32
                         mol_type = protein
                         organism = synthetic construct
VARIANT                  6
                         note = X in position 6 means an amino acid selected from
                          Alanine, Tyrosine and Threonine
SEQUENCE: 28
RFTISXDNSK NTLYLQMNSL RAEDTAVYYC AR                                          32

SEQ ID NO: 29            moltype = AA   length = 117
FEATURE                  Location/Qualifiers
source                   1..117
                         mol_type = protein
                         organism = synthetic construct
SEQUENCE: 29
EVQLVESGGG LIQPGGSLRL SCAASTITVT SNYMSWVRQA PGKGLEWVSV IYPGGSTFYA            60
DSVKGRFTIS ADNSKNTLYL QMNSLRAEDT AVYYCARDLV VYGMDVWGQG TTVTVSS              117

SEQ ID NO: 30            moltype = AA   length = 104
FEATURE                  Location/Qualifiers
source                   1..104
                         mol_type = protein
                         organism = synthetic construct
SEQUENCE: 30
EIVLTQSPGT LSLSPGERAT LSCRASQGVS SSYLAWYQQK PGQAPRLLIY GASSRATGIP            60
GRFSGSGSGT DFTLTISRLE PEDFAVYYCQ QGVTFGGGTK VEIK                            104

SEQ ID NO: 31            moltype = AA   length = 117
FEATURE                  Location/Qualifiers
source                   1..117
                         mol_type = protein
                         organism = synthetic construct
SEQUENCE: 31
EVQLVESGGG LIQPGGSLRL SCAASTITVT SNYMSWVRQA PGKGLEWVSV IYPGGSTFYA            60
DSVKGRFTIS ADNSKNTLYL QMNSLRAEDT AVYYCARDLV VYGMDVWGQG TTVTVSS              117

SEQ ID NO: 32            moltype = AA   length = 104
FEATURE                  Location/Qualifiers
source                   1..104
                         mol_type = protein
                         organism = synthetic construct
SEQUENCE: 32
EIVLTQSPGT LSLSPGERAT LSCRASQSVS SSYLAWYQQK PGQAPRLLIY GASSRATGIP            60
GRFSGSGSGT DFTLTISRLE PEDFAVYYCQ QGVTFGGGTK VEIK                            104

SEQ ID NO: 33            moltype = AA   length = 117
FEATURE                  Location/Qualifiers
source                   1..117
                         mol_type = protein
                         organism = synthetic construct
SEQUENCE: 33
EVQLVESGGG LIQPGGSLRL SCAASVITVT SNYMSWVRQA PGKGLEWVSV IYPGGSTFYA            60
DSVKGRFTIS ADNSKNTLYL QMNSLRAEDT AVYYCARDLV VYGMDVWGQG TTVTVSS              117

SEQ ID NO: 34            moltype = AA   length = 104
FEATURE                  Location/Qualifiers
source                   1..104
                         mol_type = protein
                         organism = synthetic construct
SEQUENCE: 34
EIVLTQSPGT LSLSPGERAT LSCRASQSVS SSYLAWYQQK PGQAPRLLIY GASSRATGIP            60
GRFSGSGSGT DFTLTISRLE PEDFAVYYCQ QGVTFGGGTK VEIK                            104

SEQ ID NO: 35            moltype = AA   length = 117
FEATURE                  Location/Qualifiers
source                   1..117
                         mol_type = protein
                         organism = synthetic construct
SEQUENCE: 35
EVQLVESGGG LIQPGGSLRL SCAASVITVT SNYMSWVRQA PGKGLEWVSV IYPGGSTFYA            60
DSVKGRFTIS ADNSKNTLYL QMNSLRAEDT AVYYCARDLV VYGMDVWGQG TTVTVSS              117
```

```
SEQ ID NO: 36              moltype = AA   length = 104
FEATURE                    Location/Qualifiers
source                     1..104
                           mol_type = protein
                           organism = synthetic construct
SEQUENCE: 36
EIVLTQSPGT LSLSPGERAT LSCRASQSVS SSYLAWYQQK PGQAPRLLIY GASSRATGIP   60
GRFSGSGSGT DFTLTISRLE PEDFAIYYCQ QGVTFGGGTK VEIK                   104

SEQ ID NO: 37              moltype = AA   length = 117
FEATURE                    Location/Qualifiers
source                     1..117
                           mol_type = protein
                           organism = synthetic construct
SEQUENCE: 37
EVQLVESGGG LIQPGGSLRL SCAASGITVT SNYMSWVRQA PGKGLEWVSV IYPGGSTFYA   60
DSVKGRFTIS ADNSKNTLYL QMNSLRAEDT AVYYCARDLV VYGMDVWGQG TTVTVSS     117

SEQ ID NO: 38              moltype = AA   length = 104
FEATURE                    Location/Qualifiers
source                     1..104
                           mol_type = protein
                           organism = synthetic construct
SEQUENCE: 38
EIVLTQSPGT LSLSPGERAT LSCRASQSVS SSYLAWYQQK PGQAPRLLIY GASSRATGIP   60
GRFSGSGSGT DFTLTISRLE PEDFAIYYCQ QGVTFGGGTK VEIK                   104

SEQ ID NO: 39              moltype = AA   length = 117
FEATURE                    Location/Qualifiers
source                     1..117
                           mol_type = protein
                           organism = synthetic construct
SEQUENCE: 39
EVQLVESGGG LIQPGGSLRL SCAASIITVT SNYMSWVRQA PGKGLEWVSV IYPGGSTFYA   60
DSVKGRFTIS YDNSKNTLYL QMNSLRAEDT AVYYCARDLV VYGMDVWGQG TTVTVSS     117

SEQ ID NO: 40              moltype = AA   length = 104
FEATURE                    Location/Qualifiers
source                     1..104
                           mol_type = protein
                           organism = synthetic construct
SEQUENCE: 40
EIVLTQSPGT LSLSPGERAT LSCRASQSVS DSYLAWYQQK PGQAPRLLIY GASSRATGIP   60
GRFSGSGSGT DFTLTISRLE PEDFAIYYCQ YGVTFGGGTK VEIK                   104

SEQ ID NO: 41              moltype = AA   length = 117
FEATURE                    Location/Qualifiers
source                     1..117
                           mol_type = protein
                           organism = synthetic construct
SEQUENCE: 41
EVQLVESGGG LIQPGGSLRL SCAASIITVT SNYMSWVRQA PGKGLEWVSV IYPGGSTFYA   60
DSVKGRFTIS YDNSKNTLYL QMNSLRAEDT AVYYCARDLV VYGMDVWGQG TTVTVSS     117

SEQ ID NO: 42              moltype = AA   length = 104
FEATURE                    Location/Qualifiers
source                     1..104
                           mol_type = protein
                           organism = synthetic construct
SEQUENCE: 42
EIVLTQSPGT LSLSPGERAT LSCRASQSVS SSYLAWYQQK PGQAPRLLIY GASSRATGIP   60
GRFSGSGSGT DFTLTISRLE PEDFAIYYCQ QGVTFGGGTK VEIK                   104

SEQ ID NO: 43              moltype = AA   length = 117
FEATURE                    Location/Qualifiers
source                     1..117
                           mol_type = protein
                           organism = synthetic construct
SEQUENCE: 43
EVQLVESGGG LIQPGGSLRL SCAASIITVT SNYMSWVRQA PGKGLEWVSV AYPGGSTFYA   60
DSVKGRFTIS TDNSKNTLYL QMNSLRAEDT AVYYCARDLV VYGMDVWGQG TTVTVSS     117

SEQ ID NO: 44              moltype = AA   length = 104
FEATURE                    Location/Qualifiers
source                     1..104
                           mol_type = protein
                           organism = synthetic construct
SEQUENCE: 44
EIVLTQSPGT LSLSPGERAT LSCRASQSVS DSYLAWYQQK PGQAPRLLIY GASSRATGIP   60
```

```
GRFSGSGSGT DFTLTISRLE PEDFAVYYCQ YGVTFGGGTK VEIK            104

SEQ ID NO: 45              moltype = AA   length = 117
FEATURE                    Location/Qualifiers
source                     1..117
                           mol_type = protein
                           organism = synthetic construct
SEQUENCE: 45
EVQLVESGGG LIQPGGSLRL SCAASIITVT SNYMSWVRQA PGKGLEWVSV AYPGGSTFYA  60
DSVKGRFTIS TDNSKNTLYL QMNSLRAEDT AVYYCARDLV VYGMDVWGQG TTVTVSS    117

SEQ ID NO: 46              moltype = AA   length = 104
FEATURE                    Location/Qualifiers
source                     1..104
                           mol_type = protein
                           organism = synthetic construct
SEQUENCE: 46
EIVLTQSPGT LSLSPGERAT LSCRASQSVS SSYLAWYQQK PGQAPRLLIY GASSRATGIP  60
GRFSGSGSGT DFTLTISRLE PEDFAVYYCQ QGVTFGGGTK VEIK                 104

SEQ ID NO: 47              moltype = AA   length = 117
FEATURE                    Location/Qualifiers
source                     1..117
                           mol_type = protein
                           organism = synthetic construct
SEQUENCE: 47
EVQLVESGGG LIQPGGSLRL SCAASIITVT SNYMSWVRQA PGKGLEWVSV IYPGGSTFYA  60
DSVKGRFTIS TDNSKNTLYL QMNSLRAEDT AVYYCARDLV VYGMDVWGQG TTVTVSS    117

SEQ ID NO: 48              moltype = AA   length = 104
FEATURE                    Location/Qualifiers
source                     1..104
                           mol_type = protein
                           organism = synthetic construct
SEQUENCE: 48
EIVLTQSPGT LSLSPGERAT LSCRASQSVS SSYLAWYQQK PGQAPRLLIY GASSRATGIP  60
GRFSGSGSGT DFTLTISRLE PEDFAVYYCQ QGVTFGGGTK VEIK                 104

SEQ ID NO: 49              moltype = AA   length = 330
FEATURE                    Location/Qualifiers
source                     1..330
                           mol_type = protein
                           organism = synthetic construct
SEQUENCE: 49
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG 120
PSVFLFPPKP KDTLMISRTP EVTCVVVDVS HEDPEVKFNW YVDGVEVHNA KTKPREEQYN 180
STYRVVSVLT VLHQDWLNGK EYKCKVSNKA LPAPIEKTIS KAKGQPREPQ VYTLPPSREE 240
MTKNQVSLTC LVKGFYPSDI AVEWESNGQP ENNYKTTPPV LDSDGSFFLY SKLTVDKSRW 300
QQGNVFSCSV MHEALHNHYT QKSLSLSPGK                                 330

SEQ ID NO: 50              moltype = AA   length = 107
FEATURE                    Location/Qualifiers
source                     1..107
                           mol_type = protein
                           organism = synthetic construct
SEQUENCE: 50
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC              107

SEQ ID NO: 51              moltype = AA   length = 447
FEATURE                    Location/Qualifiers
source                     1..447
                           mol_type = protein
                           organism = synthetic construct
SEQUENCE: 51
EVQLVESGGG LIQPGGSLRL SCAASTITVT SNYMSWVRQA PGKGLEWVSV IYPGGSTFYA  60
DSVKGRFTIS ADNSKNTLYL QMNSLRAEDT AVYYCARDLV VYGMDVWGQG TTVTVSSAST 120
KGPSVFPLAP SSKSTSGGTA ALGCLVKDYF PEPVTVSWNS GALTSGVHTF PAVLQSSGLY 180
SLSSVVTVPS SSLGTQTYIC NVNHKPSNTK VDKRVEPKSC DKTHTCPPCP APELLGGPSV 240
FLFPPKPKDT LMISRTPEVT CVVVDVSHED PEVKFNWYVD GVEVHNAKTK PREEQYNSTY 300
RVVSVLTVLH QDWLNGKEYK CKVSNKALPA PIEKTISKAK GQPREPQVYT LPPSREEMTK 360
NQVSLTCLVK GFYPSDIAVE WESNGQPENN YKTTPPVLDS DGSFFLYSKL TVDKSRWQQG 420
NVFSCSVMHE ALHNHYTQKS LSLSPGK                                    447

SEQ ID NO: 52              moltype = AA   length = 211
FEATURE                    Location/Qualifiers
source                     1..211
                           mol_type = protein
```

```
                         organism = synthetic construct
SEQUENCE: 52
EIVLTQSPGT LSLSPGERAT LSCRASQGFS SSYLAWYQQK PGQAPRLLIY GASSRATGIP    60
GRFSGSGSGT DFTLTISRLE PEDFAVYYCQ QGVTFGGGTK VEIKRTVAAP SVFIFPPSDE   120
QLKSGTASVV CLLNNFYPRE AKVQWKVDNA LQSGNSQESV TEQDSKDSTY SLSSTLTLSK   180
ADYEKHKVYA CEVTHQGLSS PVTKSFNRGE C                                  211

SEQ ID NO: 53            moltype = AA  length = 447
FEATURE                  Location/Qualifiers
source                   1..447
                         mol_type = protein
                         organism = synthetic construct
SEQUENCE: 53
EVQLVESGGG LIQPGGSLRL SCAASTITVT SNYMSWVRQA PGKGLEWVSV IYPGGSTFYA    60
DSVKGRFTIS ADNSKNTLYL QMNSLRAEDT AVYYCARDLV VYGMDVWGQG TTVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKRVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGK                                       447

SEQ ID NO: 54            moltype = AA  length = 211
FEATURE                  Location/Qualifiers
source                   1..211
                         mol_type = protein
                         organism = synthetic construct
SEQUENCE: 54
EIVLTQSPGT LSLSPGERAT LSCRASQGVS SSYLAWYQQK PGQAPRLLIY GASSRATGIP    60
GRFSGSGSGT DFTLTISRLE PEDFAVYYCQ QGVTFGGGTK VEIKRTVAAP SVFIFPPSDE   120
QLKSGTASVV CLLNNFYPRE AKVQWKVDNA LQSGNSQESV TEQDSKDSTY SLSSTLTLSK   180
ADYEKHKVYA CEVTHQGLSS PVTKSFNRGE C                                  211

SEQ ID NO: 55            moltype = AA  length = 447
FEATURE                  Location/Qualifiers
source                   1..447
                         mol_type = protein
                         organism = synthetic construct
SEQUENCE: 55
EVQLVESGGG LIQPGGSLRL SCAASTITVT SNYMSWVRQA PGKGLEWVSV IYPGGSTFYA    60
DSVKGRFTIS ADNSKNTLYL QMNSLRAEDT AVYYCARDLV VYGMDVWGQG TTVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKRVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGK                                       447

SEQ ID NO: 56            moltype = AA  length = 211
FEATURE                  Location/Qualifiers
source                   1..211
                         mol_type = protein
                         organism = synthetic construct
SEQUENCE: 56
EIVLTQSPGT LSLSPGERAT LSCRASQSVS SSYLAWYQQK PGQAPRLLIY GASSRATGIP    60
GRFSGSGSGT DFTLTISRLE PEDFAVYYCQ QGVTFGGGTK VEIKRTVAAP SVFIFPPSDE   120
QLKSGTASVV CLLNNFYPRE AKVQWKVDNA LQSGNSQESV TEQDSKDSTY SLSSTLTLSK   180
ADYEKHKVYA CEVTHQGLSS PVTKSFNRGE C                                  211

SEQ ID NO: 57            moltype = AA  length = 447
FEATURE                  Location/Qualifiers
source                   1..447
                         mol_type = protein
                         organism = synthetic construct
SEQUENCE: 57
EVQLVESGGG LIQPGGSLRL SCAASVITVT SNYMSWVRQA PGKGLEWVSV IYPGGSTFYA    60
DSVKGRFTIS ADNSKNTLYL QMNSLRAEDT AVYYCARDLV VYGMDVWGQG TTVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKRVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGK                                       447

SEQ ID NO: 58            moltype = AA  length = 211
FEATURE                  Location/Qualifiers
source                   1..211
                         mol_type = protein
                         organism = synthetic construct
```

```
SEQUENCE: 58
EIVLTQSPGT LSLSPGERAT LSCRASQSVS SSYLAWYQQK PGQAPRLLIY GASSRATGIP    60
GRFSGSGSGT DFTLTISRLE PEDFAVYYCQ QGVTFGGGTK VEIKRTVAAP SVFIFPPSDE   120
QLKSGTASVV CLLNNFYPRE AKVQWKVDNA LQSGNSQESV TEQDSKDSTY SLSSTLTLSK   180
ADYEKHKVYA CEVTHQGLSS PVTKSFNRGE C                                  211

SEQ ID NO: 59           moltype = AA    length = 447
FEATURE                 Location/Qualifiers
source                  1..447
                        mol_type = protein
                        organism = synthetic construct
SEQUENCE: 59
EVQLVESGGG LIQPGGSLRL SCAASVITVT SNYMSWVRQA PGKGLEWVSV IYPGGSTFYA    60
DSVKGRFTIS ADNSKNTLYL QMNSLRAEDT AVYYCARDLV VYGMDVWGQG TTVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKRVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGK                                       447

SEQ ID NO: 60           moltype = AA    length = 211
FEATURE                 Location/Qualifiers
source                  1..211
                        mol_type = protein
                        organism = synthetic construct
SEQUENCE: 60
EIVLTQSPGT LSLSPGERAT LSCRASQSVS SSYLAWYQQK PGQAPRLLIY GASSRATGIP    60
GRFSGSGSGT DFTLTISRLE PEDFAIYYCQ QGVTFGGGTK VEIKRTVAAP SVFIFPPSDE   120
QLKSGTASVV CLLNNFYPRE AKVQWKVDNA LQSGNSQESV TEQDSKDSTY SLSSTLTLSK   180
ADYEKHKVYA CEVTHQGLSS PVTKSFNRGE C                                  211

SEQ ID NO: 61           moltype = AA    length = 447
FEATURE                 Location/Qualifiers
source                  1..447
                        mol_type = protein
                        organism = synthetic construct
SEQUENCE: 61
EVQLVESGGG LIQPGGSLRL SCAASGITVT SNYMSWVRQA PGKGLEWVSV IYPGGSTFYA    60
DSVKGRFTIS ADNSKNTLYL QMNSLRAEDT AVYYCARDLV VYGMDVWGQG TTVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKRVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGK                                       447

SEQ ID NO: 62           moltype = AA    length = 211
FEATURE                 Location/Qualifiers
source                  1..211
                        mol_type = protein
                        organism = synthetic construct
SEQUENCE: 62
EIVLTQSPGT LSLSPGERAT LSCRASQSVS SSYLAWYQQK PGQAPRLLIY GASSRATGIP    60
GRFSGSGSGT DFTLTISRLE PEDFAIYYCQ QGVTFGGGTK VEIKRTVAAP SVFIFPPSDE   120
QLKSGTASVV CLLNNFYPRE AKVQWKVDNA LQSGNSQESV TEQDSKDSTY SLSSTLTLSK   180
ADYEKHKVYA CEVTHQGLSS PVTKSFNRGE C                                  211

SEQ ID NO: 63           moltype = AA    length = 447
FEATURE                 Location/Qualifiers
source                  1..447
                        mol_type = protein
                        organism = synthetic construct
SEQUENCE: 63
EVQLVESGGG LIQPGGSLRL SCAASIITVT SNYMSWVRQA PGKGLEWVSV IYPGGSTFYA    60
DSVKGRFTIS YDNSKNTLYL QMNSLRAEDT AVYYCARDLV VYGMDVWGQG TTVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKRVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGK                                       447

SEQ ID NO: 64           moltype = AA    length = 211
FEATURE                 Location/Qualifiers
source                  1..211
                        mol_type = protein
                        organism = synthetic construct
SEQUENCE: 64
```

```
EIVLTQSPGT LSLSPGERAT LSCRASQSVS DSYLAWYQQK PGQAPRLLIY GASSRATGIP    60
GRFSGSGSGT DFTLTISRLE PEDFAIYYCQ YGVTFGGGTK VEIKRTVAAP SVFIFPPSDE   120
QLKSGTASVV CLLNNFYPRE AKVQWKVDNA LQSGNSQESV TEQDSKDSTY SLSSTLTLSK   180
ADYEKHKVYA CEVTHQGLSS PVTKSFNRGE C                                  211

SEQ ID NO: 65             moltype = AA  length = 447
FEATURE                   Location/Qualifiers
source                    1..447
                          mol_type = protein
                          organism = synthetic construct
SEQUENCE: 65
EVQLVESGGG LIQPGGSLRL SCAASIITVT SNYMSWVRQA PGKGLEWVSV IYPGGSTFYA    60
DSVKGRFTIS YDNSKNTLYL QMNSLRAEDT AVYYCARDLV VYGMDVWGQG TTVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKRVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGK                                       447

SEQ ID NO: 66             moltype = AA  length = 211
FEATURE                   Location/Qualifiers
source                    1..211
                          mol_type = protein
                          organism = synthetic construct
SEQUENCE: 66
EIVLTQSPGT LSLSPGERAT LSCRASQSVS SSYLAWYQQK PGQAPRLLIY GASSRATGIP    60
GRFSGSGSGT DFTLTISRLE PEDFAIYYCQ QGVTFGGGTK VEIKRTVAAP SVFIFPPSDE   120
QLKSGTASVV CLLNNFYPRE AKVQWKVDNA LQSGNSQESV TEQDSKDSTY SLSSTLTLSK   180
ADYEKHKVYA CEVTHQGLSS PVTKSFNRGE C                                  211

SEQ ID NO: 67             moltype = AA  length = 447
FEATURE                   Location/Qualifiers
source                    1..447
                          mol_type = protein
                          organism = synthetic construct
SEQUENCE: 67
EVQLVESGGG LIQPGGSLRL SCAASIITVT SNYMSWVRQA PGKGLEWVSV AYPGGSTFYA    60
DSVKGRFTIS TDNSKNTLYL QMNSLRAEDT AVYYCARDLV VYGMDVWGQG TTVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKRVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGK                                       447

SEQ ID NO: 68             moltype = AA  length = 211
FEATURE                   Location/Qualifiers
source                    1..211
                          mol_type = protein
                          organism = synthetic construct
SEQUENCE: 68
EIVLTQSPGT LSLSPGERAT LSCRASQSVS DSYLAWYQQK PGQAPRLLIY GASSRATGIP    60
GRFSGSGSGT DFTLTISRLE PEDFAVYYCQ YGVTFGGGTK VEIKRTVAAP SVFIFPPSDE   120
QLKSGTASVV CLLNNFYPRE AKVQWKVDNA LQSGNSQESV TEQDSKDSTY SLSSTLTLSK   180
ADYEKHKVYA CEVTHQGLSS PVTKSFNRGE C                                  211

SEQ ID NO: 69             moltype = AA  length = 447
FEATURE                   Location/Qualifiers
source                    1..447
                          mol_type = protein
                          organism = synthetic construct
SEQUENCE: 69
EVQLVESGGG LIQPGGSLRL SCAASIITVT SNYMSWVRQA PGKGLEWVSV AYPGGSTFYA    60
DSVKGRFTIS TDNSKNTLYL QMNSLRAEDT AVYYCARDLV VYGMDVWGQG TTVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKRVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGK                                       447

SEQ ID NO: 70             moltype = AA  length = 211
FEATURE                   Location/Qualifiers
source                    1..211
                          mol_type = protein
                          organism = synthetic construct
SEQUENCE: 70
EIVLTQSPGT LSLSPGERAT LSCRASQSVS SSYLAWYQQK PGQAPRLLIY GASSRATGIP    60
```

```
GRFSGSGSGT DFTLTISRLE PEDFAVYYCQ QGVTFGGGTK VEIKRTVAAP SVFIFPPSDE   120
QLKSGTASVV CLLNNFYPRE AKVQWKVDNA LQSGNSQESV TEQDSKDSTY SLSSTLTLSK   180
ADYEKHKVYA CEVTHQGLSS PVTKSFNRGE C                                  211

SEQ ID NO: 71           moltype = AA   length = 447
FEATURE                 Location/Qualifiers
source                  1..447
                        mol_type = protein
                        organism = synthetic construct
SEQUENCE: 71
EVQLVESGGG LIQPGGSLRL SCAASIITVT SNYMSWVRQA PGKGLEWVSV IYPGGSTFYA    60
DSVKGRFTIS TDNSKNTLYL QMNSLRAEDT AVYYCARDLV VYGMDVWGQG TTVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKRVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGK                                       447

SEQ ID NO: 72           moltype = AA   length = 211
FEATURE                 Location/Qualifiers
source                  1..211
                        mol_type = protein
                        organism = synthetic construct
SEQUENCE: 72
EIVLTQSPGT LSLSPGERAT LSCRASQSVS SSYLAWYQQK PGQAPRLLIY GASSRATGIP    60
GRFSGSGSGT DFTLTISRLE PEDFAVYYCQ QGVTFGGGTK VEIKRTVAAP SVFIFPPSDE   120
QLKSGTASVV CLLNNFYPRE AKVQWKVDNA LQSGNSQESV TEQDSKDSTY SLSSTLTLSK   180
ADYEKHKVYA CEVTHQGLSS PVTKSFNRGE C                                  211

SEQ ID NO: 73           moltype = AA   length = 116
FEATURE                 Location/Qualifiers
source                  1..116
                        mol_type = protein
                        organism = synthetic construct
SEQUENCE: 73
EVQLVESGGG LIQPGGSLRL SCAASGITVT SNYMSWVRQA PGKGLEWVSV IYPGGSTFYA    60
DSVKGRFTIS RDNSKNTLYL QMNSLRAEDT AVYYCARDLV VYGMDVWGQG TTVTVS       116

SEQ ID NO: 74           moltype = AA   length = 104
FEATURE                 Location/Qualifiers
source                  1..104
                        mol_type = protein
                        organism = synthetic construct
SEQUENCE: 74
EIVLTQSPGT LSLSPGERAT LSCRASQSVS SSYLAWYQQK PGQAPRLLIY GASSRATGIP    60
GRFSGSGSGT DFTLTISRLE PEDFAIYYCQ QGVTFGGGTK VEIK                    104

SEQ ID NO: 75           moltype = AA   length = 1276
FEATURE                 Location/Qualifiers
source                  1..1276
                        mol_type = protein
                        organism = synthetic construct
SEQUENCE: 75
MFVFLVLLPL VSSQCVNLTT RTQLPPAYTN SFTRGVYYPD KVFRSSVLHS TQDLFLPFFS    60
NVTWFHAIHV SGTNGTKRFD NPVLPFNDGV YFASTEKSNI IRGWIFGTTL DSKTQSLLIV   120
NNATNVVIKV CEFQFCNDPF LGVYYHKNNK SWMESEFRVY SSANNCTFEY VSQPFLMDLE   180
GKQGNFKNLR EFVFKNIDGY FKIYSKHTPI NLVRDLPQGF SALEPLVDLP IGINITRFQT   240
LLALHRSYLT PGDSSSGWTA GAAAYYVGYL QPRTFLLKYN ENGTITDAVD CALDPLSETK   300
CTLKSFTVEK GIYQTSNFRV QPTESIVRFP NITNLCPFGE VFNATRFASV YAWNRKRISN   360
CVADYSFLYN SASFSTFKCY GVSPTKLNDL CFTNVYADSF VIRGDEVRQI APGQTGKIAD   420
YNYKLPDDFT GCVIAWNSNN LDSKVGGNYN YLYRLFRKSN LKPFERDIST EIYQAGSTPC   480
NGVEGFNCYF PLQSYGFQPT NGVGYQPYRV VVLSFELLHA PATVCGPKKS TNLVKNKCVN   540
FNFNGLTGTG VLTESNKKFL PFQQFGRDIA DTTDAVRDPQ TLEILDITPC SFGGVSVITP   600
GTNTSNQVAV LYQDVNCTEV PVAIHADQLT PTWRVYSTGS NVFQTRAGCL IGAEHVNNSY   660
ECDIPIGAGI CASYQTQTNS PRRARSVASQ SIIAYTMSLG AENSVAYSNN SIAIPTNFTI   720
SVTTEILPVS MTKTSVDCTM YICGDSTECS NLLLQYGSFC TQLNRALTGI AVEQDKNTQE   780
VFAQVKQIYK TPPIKDFGGF NFSQILPDPS KPSKRSFIED LLFNKVTLAD AGFIKQYGDC   840
LGDIAARDLI CAQKFNGLTV LPPLLTDEMI AQYTSALLAG TITSGWTFGA GAALQIPFAM   900
QMAYRFNGIG VTQNVLYENQ KLIANQFNSA IGKIQDSLSS TASALGKLQD VVNQNAQALN   960
TLVKQLSSNF GAISSVLNDI LSRLDPPEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQGS GYIPEAPRDG QAYVRKDGEW VLLSTFLGGS HHHHHHHHSA WSHPQFEKGT  1260
GGLNDIFEAQ KIEWHE                                                  1276

SEQ ID NO: 76           moltype = AA   length = 696
FEATURE                 Location/Qualifiers
```

```
source                  1..696
                        mol_type = protein
                        organism = synthetic construct
SEQUENCE: 76
MGWSCIILFL VATATGVHSV NLTTRTQLPP AYTNSFTRGV YYPDKVFRSS VLHSTQDLFL   60
PFFSNVTWFH AIHVSGTNGT KRFDNPVLPF NDGVYFASTE KSNIIRGWIF GTTLDSKTQS  120
LLIVNNATNV VIKVCEFQFC NDPFLGVYYH KNNKSWMESE FRVYSSANNC TFEYVSQPFL  180
MDLEGKQGNF KNLREFVFKN IDGYFKIYSK HTPINLVRDL PQGFSALEPL VDLPIGINIT  240
RFQTLLALHR SYLTPGDSSS GWTAGAAAYY VGYLQPRTFL LKYNENGTIT DAVDCALDPL  300
SETKCTLKSF TVEKGIYQTS NFRVQPTESI VRFPNITNLC PFGEVFNATR FASVYAWNRK  360
RISNCVADYS FLYNSASFST FKCYGVSPTK LNDLCFTNVY ADSFVIRGDE VRQIAPGQTG  420
KIADYNYKLP DDFTGCVIAW NSNNLDSKVG GNYNYLRLF RKSNLKPFER DISTEIYQAG  480
STPCNGVEGF NCYFPLQSYG FQPTNGVGYQ PYRVVVLSFE LLHAPATVCG PKKSTNLVKN  540
KCVNFNFNGL TGTGVLTESN KKFLPFQQFG RDIADTTDAV RDPQTLEILD ITPCSFGGVS  600
VITPGTNTSN QVALYQDVN CTEVPVAIHA DQLTPTWRVY STGSNVFQTR AGCLIGAEHV  660
NNSYECDIPI GAGICASYQT QTNSPGGSHH HHHHHH                          696

SEQ ID NO: 77           moltype = AA  length = 263
FEATURE                 Location/Qualifiers
source                  1..263
                        mol_type = protein
                        organism = synthetic construct
SEQUENCE: 77
METDTLLLWV LLLWVPGSTG NITNLCPFGE VFNATRFASV YAWNRKRISN CVADYSFLYN   60
SASFSTFKCY GVSPTKLNDL CFTNVYADSF VIRGDEVRQI APGQTGKIAD YNYKLPDDFT  120
GCVIAWNSNN LDSKVGGNYN YLYRLFRKSN LKPFERDIST EIYQAGSTPC NGVEGFNCYF  180
PLQSYGFQPT NGVGYQPYRV VVLSFELLHA PATVCGPKGS GLVPRGSHHH HHHHHSAWSH  240
PQFEKGTGGL NDIFEAQKIE WHE                                        263

SEQ ID NO: 78           moltype = AA  length = 263
FEATURE                 Location/Qualifiers
source                  1..263
                        mol_type = protein
                        organism = synthetic construct
SEQUENCE: 78
METDTLLLWV LLLWVPGSTG NITNLCPFGE VFNATRFASV YAWNRKRISN CVADYSFLYN   60
SASFSTFKCY GVSPTKLNDL CFTNVYADSF VIRGDEVRQI APGQTGKIAD YNYKLPDDFT  120
GCVIAWNSNN LDSKVGGNYN YLYRLFRKSN LKPFERDIST EIYQAGSTPC NGVEGFNCYF  180
PLQSYGFQPT NGVGYQPYRV VVLSFELLHA PATVCGPKGS GLVPRGSHHH HHHHHSAWSH  240
PQFEKGTGGL NDIFEAQKIE WHE                                        263

SEQ ID NO: 79           moltype = AA  length = 263
FEATURE                 Location/Qualifiers
source                  1..263
                        mol_type = protein
                        organism = synthetic construct
SEQUENCE: 79
METDTLLLWV LLLWVPGSTG NITNLCPFGE VFNATRFASV YAWNRKRISN CVADYSFLYN   60
SASFSTFKCY GVSPTKLNDL CFTNVYADSF VIRGDEVRQI APGQTGKIAD YNYKLPDDFT  120
GCVIAWNSNN LDSKVGGNYN YRYRLFRKSN LKPFERDIST EIYQAGSKPC NGVEGFNCYF  180
PLQSYGFQPT NGVGYQPYRV VVLSFELLHA PATVCGPKGS GLVPRGSHHH HHHHHSAWSH  240
PQFEKGTGGL NDIFEAQKIE WHE                                        263

SEQ ID NO: 80           moltype = AA  length = 263
FEATURE                 Location/Qualifiers
source                  1..263
                        mol_type = protein
                        organism = synthetic construct
SEQUENCE: 80
METDTLLLWV LLLWVPGSTG NITNLCPFDE VFNATRFASV YAWNRKRISN CVADYSVLYN   60
FAPFFAFKCY GVSPTKLNDL CFTNVYADSF VIRGNEVSQI APGQTGNIAD YNYKLPDDFT  120
GCVIAWNSNK LDSKVGGNYN YLYRLFRKSN LKPFERDIST EIYQAGNKPC NGVAGFNCYF  180
PLRSYGFRPT YGVGHQPYRV VVLSFELLHA PATVCGPKGS GLVPRGSHHH HHHHHSAWSH  240
PQFEKGTGGL NDIFEAQKIE WHE                                        263

SEQ ID NO: 81           moltype = AA  length = 263
FEATURE                 Location/Qualifiers
source                  1..263
                        mol_type = protein
                        organism = synthetic construct
SEQUENCE: 81
METDTLLLWV LLLWVPGSTG NITNLCPFHE VFNATTFASV YAWNRKRISN CVADYSVLYN   60
FAPFFAFKCY GVSPTKLNDL CFTNVYADSF VIRGNEVSQI APGQTGNIAD YNYKLPDDFT  120
GCVIAWNSNK LDSKVSGNYN YLYRLFRKSK LKPFERDIST EIYQAGNKPC NGVAGSNCYF  180
PLQSYGFRPT YGVGHQPYRV VVLSFELLHA PATVCGPKGS GLVPRGSHHH HHHHHSAWSH  240
PQFEKGTGGL NDIFEAQKIE WHE                                        263

SEQ ID NO: 82           moltype = AA  length = 263
FEATURE                 Location/Qualifiers
```

```
source                  1..263
                        mol_type = protein
                        organism = synthetic construct
SEQUENCE: 82
METDTLLLWV LLLWVPGSTG NITNLCPFDE VFNATRFASV YAWNRKRISN CVADYSFLYN    60
FAPFFAFKCY GVSPTKLNDL CFTNVYADSF VIRGNEVSQI APGQTGNIAD YNYKLPDDFT   120
GCVIAWNSNK LDSKVGGNYN YRYRLFRKSN LKPFERDIST EIYQAGNKPC NGVAGVNCYF   180
PLQSYGFRPT YGVGHQPYRV VVLSFELLHA PATVCGPKGS GLVPRGSHHH HHHHHSAWSH   240
PQFEKGTGGL NDIFEAQKIE WHE                                          263

SEQ ID NO: 83           moltype = AA  length = 263
FEATURE                 Location/Qualifiers
source                  1..263
                        mol_type = protein
                        organism = synthetic construct
SEQUENCE: 83
METDTLLLWV LLLWVPGSTG NITNLCPFDE VFNATTFASV YAWNRKRISN CVADYSFLYN    60
FAPFFAFKCY GVSPTKLNDL CFTNVYADSF VIRGNEVSQI APGQTGNIAD YNYKLPDDFT   120
GCVIAWNSNK LDSTVGGNYN YRYRLFRKSK LKPFERDIST EIYQAGNKPC NGVAGVNCYF   180
PLQSYGFRPT YGVGHQPYRV VVLSFELLHA PATVCGPKGS GLVPRGSHHH HHHHHSAWSH   240
PQFEKGTGGL NDIFEAQKIE WHE                                          263

SEQ ID NO: 84           moltype = AA  length = 263
FEATURE                 Location/Qualifiers
source                  1..263
                        mol_type = protein
                        organism = synthetic construct
SEQUENCE: 84
METDTLLLWV LLLWVPGSTG NITNLCPFHE VFNATTFASV YAWNRKRISN CVADYSVIYN    60
FAPFFAFKCY GVSPTKLNDL CFTNVYADSF VIRGNEVSQI APGQTGNIAD YNYKLPDDFT   120
GCVIAWNSNK LDSKPSGNYN YLYRLFRKSK LKPFERDIST EIYQAGNKPC NGVAGPNCYS   180
PLQSYGFRPT YGVGHQPYRV VVLSFELLHA PATVCGPKGS GLVPRGSHHH HHHHHSAWSH   240
PQFEKGTGGL NDIFEAQKIE WHE                                          263

SEQ ID NO: 85           moltype = AA  length = 263
FEATURE                 Location/Qualifiers
source                  1..263
                        mol_type = protein
                        organism = synthetic construct
SEQUENCE: 85
METDTLLLWV LLLWVPGSTG NITNLCPFHE VFNATTFASV YAWNRKRISN CVADYSVIYN    60
FAPFFAFKCY GVSPTKLNDL CFTNVYADSF VIRGNEVSQI APGQTGNIAD YNYKLPDDFT   120
GCVIAWNSNK LDSKPSGNYN YLYRLFRKSK LKPFERDIST EIYQAGNRPC NGVAGPNCYS   180
PLQSYGFRPT YGVGHQPYRV VVLSFELLHA PATVCGPKGS GLVPRGSHHH HHHHHSAWSH   240
PQFEKGTGGL NDIFEAQKIE WHE                                          263

SEQ ID NO: 86           moltype = AA  length = 263
FEATURE                 Location/Qualifiers
source                  1..263
                        mol_type = protein
                        organism = synthetic construct
SEQUENCE: 86
METDTLLLWV LLLWVPGSTG NITNLCPFHE VFNATTFASV YAWNRKRISN CVADYSVIYN    60
FAPFFAFKCY GVSPTKLNDL CFTNVYADSF VIRGNEVSQI APGQTGNIAD YNYKLPDDFT   120
GCVIAWNSNK LDSKPSGNYN YLYRLLRKSK LKPFERDIST EIYQAGNKPC NGVAGPNCYS   180
PLQSYGFRPT YGVGHQPYRV VVLSFELLHA PATVCGPKGS GLVPRGSHHH HHHHHSAWSH   240
PQFEKGTGGL NDIFEAQKIE WHE                                          263

SEQ ID NO: 87           moltype = AA  length = 262
FEATURE                 Location/Qualifiers
source                  1..262
                        mol_type = protein
                        organism = synthetic construct
SEQUENCE: 87
METDTLLLWV LLLWVPGSTG NVTNLCPFHE VFNATRFASV YAWNRTRISN CVADYSVLYN    60
FAPFFAFKCY GVSPTKLNDL CFTNVYADSF VIKGNEVSQI APGQTGNIAD YNYKLPDDFT   120
GCVIAWNSNK LDSKHSGNYD YWYRLFRKSK LKPFERDIST EIYQAGNKPC KGKGPNCYFP   180
LQSYGFRPTY GVGHQPYRVV VLSFELLHAP ATVCGPKGSG LVPRGSHHHH HHHHSAWSHP   240
QFEKGTGGLN DIFEAQKIEW HE                                           262

SEQ ID NO: 88           moltype = AA  length = 262
FEATURE                 Location/Qualifiers
source                  1..262
                        mol_type = protein
                        organism = synthetic construct
SEQUENCE: 88
METDTLLLWV LLLWVPGSTG NVTNLCPFHE VFNATRFASV YAWNRTRISN CVADYSVLYN    60
FAPFFAFKCY GVSPTKLNDL CFTNVYADSF VIKGNEVSQI APGQTGNIAD YNYKLPDDFT   120
GCVIAWNSNK LDSKHSGNYD YWYRSFRKSK LKPFERDIST EIYQAGNKPC KGKGPNCYFP   180
```

```
LQSYGFRPTY GVGHQPYRVV VLSFELLHAP ATVCGPKGSG LVPRGSHHHH HHHHSAWSHP   240
QFEKGTGGLN DIFEAQKIEW HE                                           262

SEQ ID NO: 89           moltype = AA   length = 644
FEATURE                 Location/Qualifiers
source                  1..644
                        mol_type = protein
                        organism = synthetic construct
SEQUENCE: 89
METDTLLLWV LLLWVPGSTG STIEEQAKTF LDKFNHEAED LFYQSSLASW NYNTNITEEN    60
VQNMNNAGDK WSAFLKEQST LAQMYPLQEI QNLTVKLQLQ ALQQNGSSVL SEDKSKRLNT   120
ILNTMSTIYS TGKVCNPDNP QECLLLEPGL NEIMANSLDY NERLWAWESW RSEVGKQLRP   180
LYEEYVVLKN EMARANHYED YGDYWRGDYE VNGVDGYDYS RGQLIEDVEH TFEEIKPLYE   240
HLHAYVRAKL MNAYPSYISP IGCLPAHLLG DMWGRFWTNL YSLTVPFGQK PNIDVTDAMV   300
DQAWDAQRIF KEAEKFFVSV GLPNMTQGFW ENSMLTDPGN VQKAVCHPTA WDLGKGDFRI   360
LMCTKVTMDD FLTAHHEMGH IQYDMAYAAQ PFLLRNGANE GFHEAVGEIM SLSAATPKHL   420
KSIGLLSPDF QEDNETEINF LLKQALTIVG TLPFTYMLEK WRWMVFKGEI PKDQWMKKWW   480
EMKREIVGVV EPVPHDETYC DPASLFHVSN DYSFIRYYTR TLYQFQFQEA LCQAAKHEGP   540
LHKCDISNST EAGQKLFNML RLGKSEPWTL ALENVVGAKN MNVRPLLNYF EPLFTWLKDQ   600
NKNSFVGWST DWSPYADGSG LVPRGSHHHH HHHHSAWSHP QFEK                   644

SEQ ID NO: 90           moltype = AA   length = 124
FEATURE                 Location/Qualifiers
source                  1..124
                        mol_type = protein
                        organism = synthetic construct
SEQUENCE: 90
EVQLVESGGG LVKPGGSLRL SCAASGFTFS SYYMNWVRQA PGKGLEWVSS ISEDGYSTYY    60
PDSLKGRFTI SRDSAKNSLY LQMNSLRADD TAVYYCARDF SGHTAWAGTG FEYWGQGTLV   120
TVSS                                                                124

SEQ ID NO: 91           moltype = AA   length = 112
FEATURE                 Location/Qualifiers
source                  1..112
                        mol_type = protein
                        organism = synthetic construct
SEQUENCE: 91
QSVLTQPPSV SGAPGQRITI SCTGSSSNIG AGYDVHWYQQ LPGTAPKLLI YGSSSRNSGV    60
PDRFSGSKSG TSASLAITGL QAEDEADYYC QSYDSSLSVL YTFGTGTKVT VL           112

SEQ ID NO: 92           moltype = AA   length = 131
FEATURE                 Location/Qualifiers
source                  1..131
                        mol_type = protein
                        organism = synthetic construct
SEQUENCE: 92
EVQLVESGGG LVKPGGSLRL SCAASGFTFR DVWMSWVRQA PGKGLEWVGR IKSKIDGGTT    60
DYAAPVKGRF TISRDDSKNT LYLQMNSLKT EDTAVYYCTT AGSYYYDTVG PGLPEGKFDY   120
WGQGTLVTVS S                                                        131

SEQ ID NO: 93           moltype = AA   length = 112
FEATURE                 Location/Qualifiers
source                  1..112
                        mol_type = protein
                        organism = synthetic construct
SEQUENCE: 93
DIVMTQSPDS LAVSLGERAT INCKSSQSVL YSSNNKNYLA WYQQKPGQPP KLLMYWASTR    60
ESGVPDRFSG SGSGAEFTLT ISSLQAEDVA IYYCQQYYST LTFGGGTKVE IK           112

SEQ ID NO: 94           moltype = AA   length = 120
FEATURE                 Location/Qualifiers
source                  1..120
                        mol_type = protein
                        organism = synthetic construct
SEQUENCE: 94
QVQLVESGGG VVQPGRSLRL SCAASGFTFS NYAMYWVRQA PGKGLEWVAV ISYDGSNKYY    60
ADSVKGRFTI SRDNSKNTLY LQMNSLRTED TAVYYCASGS DYGDYLLVYW GQGTLVTVSS   120

SEQ ID NO: 95           moltype = AA   length = 110
FEATURE                 Location/Qualifiers
source                  1..110
                        mol_type = protein
                        organism = synthetic construct
SEQUENCE: 95
QSALTQPASV SGSPGQSITI SCTGTSSDVG GYNYVSWYQQ HPGKAPKLMI YDVSKRPSGV    60
SNRFSGSKSG NTASLTISGL QSEDEADYYC NSLTSISTWV FGGGTKLTVL              110

SEQ ID NO: 96           moltype = AA   length = 127
FEATURE                 Location/Qualifiers
```

```
source               1..127
                     mol_type = protein
                     organism = synthetic construct
SEQUENCE: 96
QVQLVQSGAE VKKPGASVKV SCKASGYPFT SYGISWVRQA PGQGLEWMGW ISTYQGNTNY    60
AQKFQGRVTM TTDTSTTTGY MELRRLRSDD TAVYYCARDY TRGAWFGESL IGGFDNWGQG   120
TLVTVSS                                                             127

SEQ ID NO: 97        moltype = AA   length = 107
FEATURE              Location/Qualifiers
source               1..107
                     mol_type = protein
                     organism = synthetic construct
SEQUENCE: 97
EIVLTQSPGT LSLSPGERAT LSCRASQTVS STSLAWYQQK PGQAPRLLIY GASSRATGIP    60
DRFSGSGSGT DFTLTISRLE PEDFAVYYCQ QHDTSLTFGG GTKVEIK                 107
```